(12) United States Patent
Sanicola-Nadel et al.

(10) Patent No.: US 6,677,135 B1
(45) Date of Patent: Jan. 13, 2004

(54) RET LIGAND (RETL) FOR STIMULATING NEUTRAL AND RENAL GROWTH

(75) Inventors: Michele Sanicola-Nadel, Winchester, MA (US); Catherine Hession, Hingham, MA (US); Richard L. Cate, Cohasset, MA (US); Dane S. Worley, Somerville, MA (US)

(73) Assignee: Biogen, Inc., Cambridge, MA (US)

(*) Notice: Subject to any disclaimer, the term of this patent is extended or adjusted under 35 U.S.C. 154(b) by 0 days.

(21) Appl. No.: 09/187,906

(22) Filed: Nov. 6, 1998

Related U.S. Application Data

(63) Continuation-in-part of application No. PCT/US97/07726, filed on May 7, 1997.
(60) Provisional application No. 60/043,533, filed on Apr. 11, 1997, provisional application No. 60/023,444, filed on Aug. 23, 1996, provisional application No. 60/021,859, filed on Jul. 16, 1996, provisional application No. 60/019,300, filed on Jun. 7, 1996, and provisional application No. 60/017,427, filed on May 8, 1996.

(51) Int. Cl.[7] .................. C12P 21/06; A61K 38/00; C07K 2/00; C07K 4/00; C07K 5/00

(52) U.S. Cl. .................. 435/69.1; 435/325; 530/300; 530/350; 536/1; 536/18.7; 536/22.1; 536/23.1

(58) Field of Search .................. 536/23.1, 22.1, 536/18.7, 1; 435/69.1, 325; 530/300, 350

(56) References Cited

U.S. PATENT DOCUMENTS

| | | | | |
|---|---|---|---|---|
| 5,514,544 | A | * | 5/1996 | Rao et al. |
| 5,607,918 | A | * | 3/1997 | Eriksson et al. |
| 5,693,495 | A | * | 12/1997 | Breiteneder et al. |
| 5,770,696 | A | * | 6/1998 | Warren et al. |
| 6,455,277 | B1 | * | 9/2002 | Fox et al. |

FOREIGN PATENT DOCUMENTS

| | | |
|---|---|---|
| EP | 0 846 764 A2 | 6/1998 |
| EP | 1 010 432 A1 | 6/2000 |
| WO | WO95/16709 A | 6/1995 |
| WO | WO 96 14861 | 5/1996 |
| WO | WO 97 11964 | 4/1997 |
| WO | WO 97 11965 | 4/1997 |
| WO | WO97/18240 A | 5/1997 |
| WO | WO 97 19693 | 6/1997 |
| WO | WO 97 19694 | 6/1997 |
| WO | WO 97 19695 | 6/1997 |
| WO | WO 97 30722 | 8/1997 |
| WO | WO97/33912 A | 9/1997 |
| WO | WO 97 34567 | 9/1997 |
| WO | WO 97/40152 | 10/1997 |
| WO | WO 98/54213 | 3/1998 |
| WO | WO 98 32458 | 7/1998 |
| WO | WO 98 36072 | 8/1998 |
| WO | WO 98 45708 | 10/1998 |
| WO | WO 98 46737 | 10/1998 |

OTHER PUBLICATIONS

Nucleic acid and amino acid database, Accession #AA049894, 1996.*
Critical Synergy: The Biotechnology Industry and Intellectual Property Protection. Biotechnology Industry Organization, 1994.*
Lin et a. Structure–Function Relationships in Glucagon: Properties of Highly Purified Des–His–, Monoiodo–, [Des–Asn(28), Thr(29)] (homoserine lactone 27)– glucagon. Biochemistry 14(8): 1559–1563, 1975.*
Schwartz et al. A superactive insulin: [B10–Aspartic acid] insulin (human). Proc. Natl. Acad. Sci. USA 84:6408–6411, 1987.*
GenCore databases. Amino acid and nucleic acid sequence search comparisons between Applicants' SEQ ID No: 1, 2, 10 and 11 and U.S. patent No. 6,455,277 (issued Sep. 24, 2002).*
Nucleic acid database, Accession #W73681, 1995.*
Nucleic acid database, Accession #Q62997, 1997.*
Jing et al. GDNF–Induced Activation of the Ret Protein Tyrosine Kinase Is Mediated by GDNFR–Alpha, a Novel Receptor for GDNF, Cell 85:1113–1124, 1996.*
Nucleic acid database, Accession #P56159, 1997.*
Nucleic acid database, Accession #O15316, 1997.*
Nucleic acid database, Accession #AA049894, 1996.*
Nucleic acid database, Accession #Q62997, 1995.*
Nucleic acid database Accession #O35977, 1997.*
Nucleic acid database, Accession #AA518362, 1996.*
Ausebel et al. Purification of Proteins by Precipitation. Current Protocols in Molecular Biology, pp. 10.61.1–10.16.11, 1991.*
Treanor, J.J.S. et al., "Characterization of a multicomponent receptor for GDNF," Nature 382:80–83 (1996).
Hillier, L. et al., "The WashU–Merck EST Project—y170a10.s1 Homo Sapiens cDNA Clone 43207 3'," EMBL Database Entry HS619153, Accession No. H05619, Jun. 23, 1995.
Hillier, L. et al., "The WashU–Merck EST Project—ye83h05.s1 Homo Sapiens cDNA Clone 124377 3'," EMBL Database Entry HS13571, Accession No. R02135, Apr. 17, 1995.

(List continued on next page.)

Primary Examiner—Alana M. Harris
(74) Attorney, Agent, or Firm—Biogen, Inc.

(57) ABSTRACT

Nucleotide and amino acid sequences are provided for compounds which promote tissue growth, as well as methods for modulating tissue growth, for imaging tissues and organs, and for treating patients. Isolated nucleic acid and amino acid sequences for Ret ligands are disclosed. Ret ligands encoded by the isolated nucleic acid sequences of the invention have a hydrophobic N-terminal signal sequence, a hydrophobic C-terminal sequence and a phosphatidylinositol glycan linkage motif. Vectors and host cells that include Ret ligands encoded by the isolated nucleic acid sequences of the invention are also disclosed.

10 Claims, 20 Drawing Sheets

OTHER PUBLICATIONS

Pandey, A. et al., "The Ret receptor protein tyrosine kinase associates with the SH2–containing adapter protein Grb10," Journal of Biological Chemistry, 270:21461–21463 (1995).

Cao, T., "c–ret and signal transduction," Cancer Bulletin, 47/2:119–124 (1995).

Pasini, B., et al., "RET mutations in human disease," Trends In Genetics, 12(4):138–144 (1996).

Hillier, et al., "The WashU–Merck EST Project—mj11d08.r1 Sores mouse embryo MbME13.5 14.5 Mus musculus cDNA clone 475791 5'," EMBL Database Entry MMAA49894, Accession No. AA049894, Dec. 31, 1996.

Mason, I., "The GDNF receptor: Recent progress and unanswered question," Mol. Cell. Neurosci., 8(2–3):112–119 (1996).

Hillier, L., et al., "The WashU–Merck EST Project—y170a10.r1 Soares infant brain 1NIB Homo Sapiens cDNA clone Image: 43207 5', mRNA sequence," GenBank Accession No. H12981.

Hillier, L., et al., "The WashU–Merck EST Project—ye83h05.r1 Soares fetal liver spleen 1NFLS Homo sapiens cDNA clone Image: 124377 5', mRNA sequence," GenBank Accession No. R02249.

Takahashi, M., et al., GenBank Accession No. X67812.

Takahashi, M., et al., GenBank Accession No. X15262.

Marra, M., et al., "The WashU–HHMI Mouse EST Project mj08d05.r1 Soares mouse embryo NbME13.5 14.5 Mus musculus cDNA clone IMAGE: 475497 5', mRNA sequence,"GenBank Accession No. AA050083.

Hillier, L., et al., "Generation and Analysis of 280,000 Human Expressed Sequence Tags," Genome Research, 6:807–828 (1996).

Lindsay, R.M. and Yancopoulos, G.D., "GDNF in a Bind with Known Orphan Accessory Implicated in New Twist," Neuron, 17:571–574 (1996).

Vega, Q.C., "Glial cell line–derived neurotrophic factor activates the receptor tyrosine kinase RET and promotes kidney morphogenesis," *Proc. Natl. Acad.* 93:10657–10661 (Oct. 1996).

Baloh et al., 1997, Neuron 18:793–802, "TrnR2, a Novel Receptor That Mediates Neurturin and GDNF Signaling through RET".

Beck et al., 1995, Nature 373:339–341, "Mesencephalic Dopaminergic Neurons Protected by GDNF from Axotomy–Induced Degeneration in the Adult Brain".

Buj–Bello et al.,1997, Nature 387:721–724, "Neurturin Responsiveness Requires a GPI–Linked Receptor and the Ret Receptor Tyrosine Kinase".

Creedon et al., 1997, Proc. Nat. Acad. Sci. USA 94, "Neurturin Shares Receptors and Signal Transduction Pathways with Glial Cell Line–Derived neurotropic Factor in Sympathetic Neurons".

Durbec et al., 1996, Development 122:349–358, "Common Origin and Developmental Dependence on C–Ret of Subsets of Enteric and Sympathetic Neuroblasts".

Durbec et al., 1996, Nature 381:789–793, "GDNF Signalling Through the Ret Receptor Tyrosine Kinase".

Edery et al., 1994, Nature 367:378–380, "Mutations of the RET Proto–Oncogene in Hirschsprung's Disease".

Eng et al., 1996, Seminars in Medicine of the Beth Israel Hospital,Boston:335:943–951, "The RET Proto–Oncogene in Multiple Endocrine Neoplasia Type 2 and Hirschsprung's Disease".

Gash et al., 1996, Nature 380:252–255, "Functional Recovery in Parkinsonian Monkeys Treated with GDNF".

Gattei et al., 1997, Blood 89:2925–2937, "Expression of the RET Receptor Tyrosine Kinase and GDNFR–alpha in Normal and Leukemic Human Hematopoietic Cells and Stromal Cells of the Bone MArrow Microenvironment".

Henderson et al., 1994, Science 266:1062–1064, "GDNF: A Potent Survival Factor for Motoneurons Present in Peripheral Nerve and Muscle".

Hofstra et al., 1994, Nature 367:375–376, "A Mutation in the RET Proto–oncogene Associated with Multiple Endocrine Neoplasia Type 2B and Sporadic Medullary Thyroid Carcinoma".

Jing et al., 1996, Cell 85:1113–1124, "GDNF–Induced Activation of the Ret Protein Tyrosine Kinase is Mediated by GDNFR–alpha, a Novel Receptor for GDNF".

Klein et al., 1997, Nature 387:717–721, "A GPI–Linked Protein that Interacts with Ret to Form a Candidate Neurturin Receptor".

Kotzbauer et al., 1996, Nature 384:467–470, "Neurturin, a Relative of Glial–Cell–Line–Derived Neurotrophic Factor".

Lin et al., 1993, Science 260:1130–1132, "GDNF: A Glial Cell Line Derived Neurotrophic Factor for Midbrain Dopaminergic Neurons".

Lindsay, Ronald M., 1995, Nature 373:289–290, "Neuron Saving Schemes".

Lindsay, Ronald M. and George D. Yancopoulos, 1996, Neuron 17:571–574, "GDNF in a Bind with Known Orphan Accessory Implicated in New Twist".

Lo, Liching and David J. Anderson, 1995, Neuron 15:527–539, "Postmigratory Neural Crest Cells Expressing c–RET Display Restricted Developmental and Proliferative Capacities".

Massague, Joan, 1996, Nature 382:29–30, "Crossing Receptor Boundaries".

Moore et al., 1996, Nature 382:76–79, "Renal and Neuronal Abnormalities in Mice Lacking GDNF".

Oppenheim et al., 1995 Nature 373:344–346, "Developing Motor Neurons Rescued from Programmed and Axotomy–Induced Cell Death by GDNF".

Pachnis et al., 1993, Development 119:1005–1017, "Expression of the C–Ret Proto–Oncogene During Mouse Embryogenesis".

Pichel et al., 1996, Nature:382:73–76, "Defects in Enteric Innervation and Kidney Development in Mice Lacking GDNF".

Robertson, Katherine and Ivor Mason, 1997, TIG:13:1–3, "The GDNF–RET Signalling Partnership".

Romeo et al., 1994, Nature 367:377–378, "Point Mutations Affecting the Tyrosine Kinase Domain of the RET Proto–oncogene in Hirschsprung's Disease".

Sanchez et al., 1996, Nature 382:70–73, "Renal Agenesis and the Absence of Enteric Neurons in Mice Lacking GDNF".

Santoro et al., 1995, Science 267:381–383, "Activation of RET as a Dominant Transforming Gene by Germline Mutations of MEN2A and MEN2B".

Schuchardt et al., 1994, Nature 367:380–383, "Defects in the Kidney and Enteric Nervous System of Mice Lacking the Tyrosine Kinase Receptor Ret".

Suvanto et al., 1997, Human Molecular Genetics 6:1267–1273, "Cloning, mRNA Distribution and Chromosomal Localisation of the Gene for Glial Cell Line–Derived Neurotrophic Factor Receptor beta, a Homologue to GDNFR–alpha".

Tomac et al., 1995, Nature 373:335–339, "Protection and Repair of the Nigrostriatal Dopaminergic System by GDNF in vivo".

Treanor et al., 1996, Nature 382:80–83, "Characterization of a Multicomponent Receptor for GDNF".

Trupp et al., 1995, Journal of Cell Biology 130:137–148, "Peripheral Expression and Biological Activities og GDNF, a New Neurotrophic Factor for Avian and Mammalian Peripheral Neurons".

Trupp et al, 1996, Nature 381:785–789, "Functional Receptor for GDNF Encoded by the c–ret Proto–oncogene".

Trupp et all., 1997, Journal of Neuroscience 17:3554–3567, "Complementary and Overlapping Expression of Glial Cell Line–Derived Neurotrophic Factor (GDNF), c–ret Proto–oncogene,and GDNF Receptor–alpha Indicates Multiple Mechanisms of Trophic Actions in the Adult Rat CNS".

Van Heyningen, Veronica, 1994, Nature 367:319–320, "One Gene—Four Syndromes".

Van Weering et al., 1997, Journal of Biological Chemistry 272:249–254, "Glial Cell Line–derived Neurotrophic Factor Induces Ret–mediated Lamellipodia Formation".

Worby et al., 1996, Journal of Biological Chemistry 271:23619–23622, "Glial Cell Line–derived Neurotrophic Factor Signals through the RET Receptor and Activates Mitogen–activated Protein Kinase".

Yan et al., 1995, Nature 373:341–344, "In vivo Neurotrophic Effects of GDNF on Neonatal and Adult Facial Motor Neurons".

* cited by examiner

```
201  AGACCGGGCGGCGGCTTTGGATTTTGGGGGGCGGGGACCAGCTGCGCGG        250

251  CGGCACCATGTTCCTAGCCACTCTGTACTTCGCGCTGCCACTCCTGGATT       300
             M  F  L  A  T  L  Y  F  A  L  P  L  L  D  L

301  TGCTGATGTCCGCCGAGGTGAGTGGTGGAGACCGTCTGGACTGTGTGAAA       350
      L  M  S  A  E  V  S  G  G  D  R  L  D  C  V  K

351  GCCAGCGATCAGTGCCTGAAGGAACAGAGCTGCAGCACCAAGTACCGCAC       400
      A  S  D  Q  C  L  K  E  Q  S  C  S  T  K  Y  R  T

401  ACTAAGGCAGTGCGTGGCGGGCAAGGAAACCAACTTCAGCCTGACATCCG       450
      L  R  Q  C  V  A  G  K  E  T  N  F  S  L  T  S  G

451  GCCTTGAGGCCAAGGATGAGTGCCGTAGCGCCATGGAGGCCTTGAAGCAG       500
      L  E  A  K  D  E  C  R  S  A  M  E  A  L  K  Q

501  AAGTCTCTGTACAACTGCCGCTGCAAGCGGGGCATGAAGAAAGAGAAGAA       550
      K  S  L  Y  N  C  R  C  K  R  G  M  K  K  E  K  N

551  TTGTCTGCGTATCTACTGGAGCATGTACCAGAGCCTGCAGGGAAATGACC       600
      C  L  R  I  Y  W  S  M  Y  Q  S  L  Q  G  N  D  L

601  TCCTGGAAGATTCCCCGTATGAGCCGGTTAACAGCAGGTTGTCAGATATA       650
      L  E  D  S  P  Y  E  P  V  N  S  R  L  S  D  I

651  TTCCGGGCAGTCCCGTTCATATCAGATGTTTTCCAGCAAGTGGAACACAT       700
      F  R  A  V  P  F  I  S  D  V  F  Q  Q  V  E  H  I

701  TTCCAAAGGGAACAACTGCCTGGACGCAGCCAAGGCCTGCAACCTGGACG       750
      S  K  G  N  N  C  L  D  A  A  K  A  C  N  L  D  D

751  ACACCTGTAAGAAGTACAGGTCGGCCTACATCACCCCCTGCACCACCAGC       800
      T  C  K  K  Y  R  S  A  Y  I  T  P  C  T  T  S

801  ATGTCCAACGAGGTCTGCAACCGCCGTAAGTGCCACAAGGCCCTCAGGCA       850
      M  S  N  E  V  C  N  R  R  K  C  H  K  A  L  R  Q

851  GTTCTTCGACAAGGTTCCGGCCAAGCACAGCTACGGGATGCTCTTCTGCT       900
      F  F  D  K  V  P  A  K  H  S  Y  G  M  L  F  C  S

901  CCTGCCGGGACATCGCCTGCACCGAGCGGCGGCGACAGACTATCGTCCCC       950
      C  R  D  I  A  C  T  E  R  R  R  Q  T  I  V  P

951  GTGTGCTCCTATGAAGAACGAGAGAGGCCCAACTGCCTGAGTCTGCAAGA       1000
      V  C  S  Y  E  E  R  E  R  P  N  C  L  S  L  Q  D

1001 CTCCTGCAAGACCAATTACATCTGCAGATCTCGCCTTGCAGATTTTTTTA      1050
      S  C  K  T  N  Y  I  C  R  S  R  L  A  D  F  F  T

1051 CCAACTGCCAGCCAGAGTCAAGGTCTGTCAGCAACTGTCTTAAGGAGAAC      1100
      N  C  Q  P  E  S  R  S  V  S  N  C  L  K  E  N

1101 TACGCAGACTGCCTCCTGGCCTACTCGGGACTGATTGGCACAGTCATGAC      1150
      Y  A  D  C  L  L  A  Y  S  G  L  I  G  T  V  M  T
```

FIG. 1a

```
1151  TCCCAACTACGTAGACTCCAGCAGCCTCAGCGTGGCACCATGGTGTGACT  1200
        P  N  Y  V  D  S  S  S  L  S  V  A  P  W  C  D  C

1201  GCAGCAACAGCGGCAATGACCTGGAAGACTGCTTGAAATTTCTGAATTTT  1250
        S  N  S  G  N  D  L  E  D  C  L  K  F  L  N  F

1251  TTTAAGGACAATACTTGTCTCAAAAATGCAATTCAAGCCTTTGGCAATGG  1300
        F  K  D  N  T  C  L  K  N  A  I  Q  A  F  G  N  G

1301  CTCAGATGTGACCATGTGGCAGCCAGCCCCTCCAGTCCAGACCACCACTG  1350
        S  D  V  T  M  W  Q  P  A  P  P  V  Q  T  T  T  A

1351  CCACCACTACCACTGCCTTCCGGGTCAAGAACAAGCCTCTGGGGCCAGCA  1400
        T  T  T  A  F  R  V  K  N  K  P  L  G  P  A

1401  GGGTCTGAGAATGAGATCCCCACACACGTTTTACCACCCTGTGCGAATTT  1450
        G  S  E  N  E  I  P  T  H  V  L  P  P  C  A  N  L

1451  GCAGGCTCAGAAGCTGAAATCCAATGTGTCGGGTAGCACACACCTCTGTC  1500
        Q  A  Q  K  L  K  S  N  V  S  G  S  T  H  L  C  L

1501  TTTCTGATAGTGATTTCGGAAAGGATGGTCTCGCTGGTGCCTCCAGCCAC  1550
        S  D  S  D  F  G  K  D  G  L  A  G  A  S  S  H

1551  ATAACCACAAAATCAATGGCTGCTCCTCCCAGCTGCAGTCTGAGCTCACT  1600
        I  T  T  K  S  M  A  A  P  P  S  C  S  L  S  S  L

1601  GCCGGTGCTGATGCTCACCGCCCTTGCTGCCCTGTTATCTGTATCGTTGG  1650
        P  V  L  M  L  T  A  L  A  A  L  L  S  V  S  L  A

1651  CAGAAACGTCGTAGCTGCATCCGGGAAAACAGTATGAAAAGACAAAAGAG  1700
        E  T  S
```

FIG. 1b

```
  1  CTGCTGGAGGATTCCCCATATGAACCAGTTAACAGCAGATTGTCAGATAT   50
     L  L  E  D  S  P  Y  E  P  V  N  S  R  L  S  D  I

51  ATTCCGGGTGGTCCCATTCATATCAGTGGAGCACATTCCCAAAGGGAACA  100
      F  R  V  V  P  F  I  S  V  E  H  I  P  K  G  N  N

101  ACTGCCTGGATGCAGCGAAGGCCTGCAACCTCGACGACATTTGCAAGAAG  150
       C  L  D  A  A  K  A  C  N  L  D  D  I  C  K  K

151  TACAGGTCGGCGTACATCACCCCGTGCACCACCAGCGTGTCCAACGATGT  200
      Y  R  S  A  Y  I  T  P  C  T  T  S  V  S  N  D  V

201  CTGCAACCGCCGCAAGTGCCACAAGGCCCTCCGGCAGTTCTTTGACAAGG  250
      C  N  R  R  K  C  H  K  A  L  R  Q  F  F  D  K  V

251  TCCCGGCCAAGCACAGCTACGGAATGCTCTTCTGCTCCTGCCGGGACATC  300
       P  A  K  H  S  Y  G  M  L  F  C  S  C  R  D  I

301  GCCTGCACAGAGCGGAGGCGACAGACCATCGTGCCTGTGTGCTCCTATGA  350
      A  C  T  E  R  R  R  Q  T  I  V  P  V  C  S  Y  E

351  AGAGAGGGAGAAGCCCAACTGTTTGAATTTGCAGGACTCCTGCAAGACGA  400
      E  R  E  K  P  N  C  L  N  L  Q  D  S  C  K  T  N

401  ATTACATCTGCAGATCTCGCCTTGCGGATTTTTTTACCAACTGCCAGCCA  450
       Y  I  C  R  S  R  L  A  D  F  F  T  N  C  Q  P

451  GAGTCAAGGTCTGTCAGCAGCTGTCTAAAGGAAAACTACGCTGACTGCCT  500
      E  S  R  S  V  S  S  C  L  K  E  N  Y  A  D  C  L

501  CCTCGCCTACTCGGGGCTTATTGGCACAGTCATGACCCCCAACTACATAG  550
       L  A  Y  S  G  L  I  G  T  V  M  T  P  N  Y  I  D

551  ACTCCAGTAGCCTCAGTGTGGCCCCATGGTGTGACTGCAGCAACAGTGGG  600
        S  S  S  L  S  V  A  P  W  C  D  C  S  N  S  G

601  AACGACCTAGAAGAGTGCTTGAAATTTTTGAATTTCTTCAAGGACAATAC  650
      N  D  L  E  E  C  L  K  F  L  N  F  F  K  D  N  T

651  ATGTCTTAAAAATGCAATTCAAGCCTTTGGCAATGGCTCCGATGTGACCG  700
       C  L  K  N  A  I  Q  A  F  G  N  G  S  D  V  T  V

701  TGTGGCAGCCAGCCTTCCCAGTACAGACCACCACTGCCACTACCACCACT  750
       W  Q  P  A  F  P  V  Q  T  T  T  A  T  T  T  T

751  GCCCTCCGGGTTAAGAACAAGCCCCTGGGGCCAGCAGGGTCTGAGAATGA  800
      A  L  R  V  K  N  K  P  L  G  P  A  G  S  E  N  E

801  AATTCCCACTCATGTTTTGCCACCGTGTGCAAATTTACAGGCACAGAAGC  850
       I  P  T  H  V  L  P  P  C  A  N  L  Q  A  Q  K  L

851  TGAAATCCAATGTGTCGGGCAATACACACCTCTGTATTTCCAATGGTAAT  900
        K  S  N  V  S  G  N  T  H  L  C  I  S  N  G  N
```

FIG. 2A-1

```
901  TATGAAAAAGAAGGTCTCGGTGCTTCCAGCCACATAACCACAAAATCAAT   950
      Y  E  K  E  G  L  G  A  S  S  H  I  T  T  K  S  M

951  GGCTGCTCCTCCAAGCTGTGGTCTGAGCCCACTGCTGGTCCTGGTGGTAA  1000
      A  A  P  P  S  C  G  L  S  P  L  L  V  L  V  V  T

1001 CCGCTCTGTCCACCCTATTATCTTTAACAGAAACATCATAGCTGCATTAA  1050
      A  L  S  T  L  L  S  L  T  E  T  S

1051 AAAAATACAATATGGACATGTAAAAGACAAAAACCAAGTTATCTGTTTC   1100

1101 CTGTTCTCTTGTATAGCTGAAATTCCAGTTTAGGAGCTCAGTTGAGAAAC  1150

1151 AGTTCCATTCAACTGGAACATTTTTTTTTTCCTTTTAAGAAAGCTTCT    1200

1201 TGTGATCCTTCGGGGCTTCTGTG   1223
```

FIG. 2A-2

```
  1  GGGCGGCCAGAGCAGCACAGCTGTCCGGGGATCGCTGCATGCTGAGCTCC   50

51  CTCGGCAAGACCCAGCGGCGGCTCGGGATTTTTTGGGGGGCGGGGACC    100

101  AGCCCCGCGCCGGCACCATGTTCCTGGCGACCCTGTACTTCGCGCTGCCG  150
                      M  F  L  A  T  L  Y  F  A  L  P

151  CTCTTGGACTTGCTCCTGTCGGCCGAAGTGAGCGGCGGAGACCGCCTGGA  200
      L  L  D  L  L  L  S  A  E  V  S  G  G  D  R  L  D

201  TTGCGTGAAAGCCAGTGATCAGTGCCTGAAGGAGCAGAGCTGCAGCACCA  250
      C  V  K  A  S  D  Q  C  L  K  E  Q  S  C  S  T  K

251  AGTACCGCACGCTAAGGCAGTGCGTGGCGGGCAAGGAGACCAACTTCAGC  300
       Y  R  T  L  R  Q  C  V  A  G  K  E  T  N  F  S

301  CTGGCATCCGGCCTGGAGGCCAAGGATGAGTGCCGCAGCGCCATGGAGGC  350
      L  A  S  G  L  E  A  K  D  E  C  R  S  A  M  E  A

351  CCTGAAGCAGAAGTCGCTCTACAACTGCCGCTGCAAGCGGGGTATGAAGA  400
      L  K  Q  K  S  L  Y  N  C  R  C  K  R  G  M  K  K

401  AGGAGAAGAACTGCCTGCGCATTTACTGGAGCATGTACCAGAGCCTGCAG  450
       E  K  N  C  L  R  I  Y  W  S  M  Y  Q  S  L  Q

451  GGAAATGATCTGCTGGAGGATTCCCCATATGAACCAGTTAACAGCAGATT  500
      G  N  D  L  L  E  D  S  P  Y  E  P  V  N  S  R  L

501  GTCAGATATATTCCGGGTGGTCCCATTCATATCAGTGGAGCACATTCCCA  550
       S  D  I  F  R  V  V  P  F  I  S  V  E  H  I  P  K

551  AAGGGAACAACTGCCTGGATGCAGCGAAGGCCTGCAACCTCGACGACATT  600
       G  N  N  C  L  D  A  A  K  A  C  N  L  D  D  I

601  TGCAAGAAGTACAGGTCGGCGTACATCACCCCGTGCACCACCAGCGTGTC  650
      C  K  K  Y  R  S  A  Y  I  T  P  C  T  T  S  V  S

651  CAACGATGTCTGCAACCGCCGCAAGTGCCACAAGGCCCTCCGGCAGTTCT  700
       N  D  V  C  N  R  R  K  C  H  K  A  L  R  Q  F  F

701  TTGACAAGGTCCCGGCCAAGCACAGCTACGGAATGCTCTTCTGCTCCTGC  750
       D  K  V  P  A  K  H  S  Y  G  M  L  F  C  S  C

751  CGGGACATCGCCTGCACAGAGCGGAGGCGACAGACCATCGTGCCTGTGTG  800
      R  D  I  A  C  T  E  R  R  R  Q  T  I  V  P  V  C

801  CTCCTATGAAGAGAGGGAGAAGCCCAACTGTTTGAATTTGCAGGACTCCT  850
       S  Y  E  E  R  E  K  P  N  C  L  N  L  Q  D  S  C

851  GCAAGACGAATTACATCTGCAGATCTCGCCTTGCGGATTTTTTTACCAAC  900
       K  T  N  Y  I  C  R  S  R  L  A  D  F  F  T  N

901  TGCCAGCCAGAGTCAAGGTCTGTCAGCAGCTGTCTAAAGGAAAACTACGC  950
      C  Q  P  E  S  R  S  V  S  S  C  L  K  E  N  Y  A
```

FIG. 2B-1

```
 951 TGACTGCCTCCTCGCCTACTCGGGGCTTATTGGCACAGTCATGACCCCA  1000
      D  C  L  L  A  Y  S  G  L  I  G  T  V  M  T  P  N

1001 ACTACATAGACTCCAGTAGCCTCAGTGTGGCCCCATGGTGTGACTGCAGC  1050
      Y  I  D  S  S  S  L  S  V  A  P  W  C  D  C  S

1051 AACAGTGGGAACGACCTAGAAGAGTGCTTGAAATTTTTGAATTTCTTCAA  1100
      N  S  G  N  D  L  E  E  C  L  K  F  L  N  F  F  K

1101 GGACAATACATGTCTTAAAAATGCAATTCAAGCCTTTGGCAATGGCTCCG  1150
      D  N  T  C  L  K  N  A  I  Q  A  F  G  N  G  S  D

1151 ATGTGACCGTGTGGCAGCCAGCCTTCCCAGTACAGACCACCACTGCCACT  1200
      V  T  V  W  Q  P  A  F  P  V  Q  T  T  T  A  T

1201 ACCACCACTGCCCTCCGGGTTAAGAACAAGCCCCTGGGGCCAGCAGGGTC  1250
      T  T  T  A  L  R  V  K  N  K  P  L  G  P  A  G  S

1251 TGAGAATGAAATTCCCACTCATGTTTTGCCACCGTGTGCAAATTTACAGG  1300
      E  N  E  I  P  T  H  V  L  P  P  C  A  N  L  Q  A

1301 CACAGAAGCTGAAATCCAATGTGTCGGGCAATACACACCTCTGTATTTCC  1350
      Q  K  L  K  S  N  V  S  G  N  T  H  L  C  I  S

1351 AATGGTAATTATGAAAAGAAGGTCTCGGTGCTTCCAGCCACATAACCAC  1400
      N  G  N  Y  E  K  E  G  L  G  A  S  S  H  I  T  T

1401 AAAATCAATGGCTGCTCCTCCAAGCTGTGGTCTGAGCCCACTGCTGGTCC  1450
      K  S  M  A  A  P  P  S  C  G  L  S  P  L  L  V  L

1451 TGGTGGTAACCGCTCTGTCCACCCTATTATCTTTAACAGAAACATCATAG  1500
      V  V  T  A  L  S  T  L  L  S  L  T  E  T  S

1501 CTGCATTAAAAAAATACAATATGGACATGTAAAAAGACAAAAACCAAGTT  1550

1551 ATCTGTTTCCTGTTCTCTTGTATAGCTGAAATTCCAGTTTAGGAGCTCAG  1600

1601 TTGAGAAACAGTTCCATTCAACTGGAACATTTTTTTTTTTCCTTTTAAG  1650

1651 AAAGCTTCTTGTGATCCTTCGGGGCTTCTGTG  1682
```

FIG. 2B-2

```
  1 GGGCGGCCAGAGCAGCACAGCTGTCCGGGGATCGCTGCATGCTGAGCTCC  50
    || |||||||||| ||| |||   | ||||||||||||||||| |||||||||
143 GAGTGGCCAGAGGAGCGCAGTCGCCCGGGGATCGCTGCACGCTGAGCTCT 192

51 CTCGGCAAGACCCAGCGGCGGCTCGGGATTTTTTTGGGGGGGCGGGGACC 100
    |||  | ||||| ||||||||||  |||       |||||||||||||||||
193 CTCCCCGAGACCGGGCGGCGGCTTTGGA...TTTTGGGGGGGCGGGGACC 239

101 AGCCCCGCGCCGGCACCATGTTCCTGGCGACCCTGTACTTCGCGCTGCCG 150
    |||    ||||  ||||||||||||||||  || || |||||||||||||||||
240 AGCTGCGCGGCGGCACCATGTTCCTAGCCACTCTGTACTTCGCGCTGCCA 289

151 CTCTTGGACTTGCTCCTGTCGGCCGAAGTGAGCGGCGGAGACCGCCTGGA 200
    ||| |||| ||||| |||| ||||| ||||| || |||||||| |||||
290 CTCCTGGATTTGCTGATGTCCGCCGAGGTGAGTGGTGGAGACCGTCTGGA 339

201 TTGCGTGAAAGCCAGTGATCAGTGCCTGAAGGAGCAGAGCTGCAGCACCA 250
    || ||||||||||||| ||||||||||||||||| ||||||||||||||||||
340 CTGTGTGAAAGCCAGCGATCAGTGCCTGAAGGAACAGAGCTGCAGCACCA 389

251 AGTACCGCACGCTAAGGCAGTGCGTGGCGGGCAAGGAGACCAACTTCAGC 300
    |||||||||| |||||||||||||||||||||||||||||  |||||||||||
390 AGTACCGCACACTAAGGCAGTGCGTGGCGGGCAAGGAAACCAACTTCAGC 439

301 CTGGCATCCGGCCTGGAGGCCAAGGATGAGTGCCGCAGCGCCATGGAGGC 350
    ||| |||||||||||  ||||||||||||||||||| |||||||||||||
440 CTGACATCCGGCCTTGAGGCCAAGGATGAGTGCCGTAGCGCCATGGAGGC 489

351 CCTGAAGCAGAAGTCGCTCTACAACTGCCGCTGCAAGCGGGGTATGAAGA 400
    | ||||||||||||| || |||||||||||||||||||||||||| ||||||
490 CTTGAAGCAGAAGTCTCTGTACAACTGCCGCTGCAAGCGGGGCATGAAGA 539

401 AGGAGAAGAACTGCCTGCGCATTTACTGGAGCATGTACCAGAGCCTGCAG 450
    | |||||||  || ||||| || |||||||||||||||||||||||||||||
540 AAGAGAAGAATTGTCTGCGTATCTACTGGAGCATGTACCAGAGCCTGCAG 589

451 GGAAATGATCTGCTGGAGGATTCCCCATATGAACCAGTTAACAGCAGATT 500
    |||||||| || ||||| ||||||||| ||||| |||||||||||||| ||
590 GGAAATGACCTCCTGGAAGATTCCCCGTATGAGCCGGTTAACAGCAGGTT 639

501 GTCAGATATATTCCGGGTGGTCCCATTCATATC................AG 535
    ||||||||||||||||| ||||| ||||||||||                ||
640 GTCAGATATATTCCGGGCAGTCCCGTTCATATCAGATGTTTTCCAGCAAG 689

536 TGGAGCACATTCCCAAAGGGAACAACTGCCTGGATGCAGCGAAGGCCTGC 585
    ||||  || ||||||||||||||||||||||||||  ||||||| ||||||||
690 TGGAACACATTTCCAAAGGGAACAACTGCCTGGACGCAGCCAAGGCCTGC 739

586 AACCTCGACGACATTTGCAAGAAGTACAGGTCGGCGTACATCACCCCGTG 635
    |||||| |||||||  || |||||||||||||||| |||||||||||| ||
740 AACCTGGACGACACCTGTAAGAAGTACAGGTCGGCCTACATCACCCCCTG 789

636 CACCACCAGCGTGTCCAACGATGTCTGCAACCGCCGCAAGTGCCACAAGG 685
    |||||||||||| |||||||||  ||||||||||||||  ||||||||||||
790 CACCACCAGCATGTCCAACGAGGTCTGCAACCGCCGTAAGTGCCACAAGG 839
```

FIG. 3A-1

```
 686 CCCTCCGGCAGTTCTTTGACAAGGTCCCGGCCAAGCACAGCTACGGAATG  735
     |||||  ||||||||||| ||||||||  ||||||||||||||||||  |||
 840 CCCTCAGGCAGTTCTTCGACAAGGTTCCGGCCAAGCACAGCTACGGGATG  889

736 CTCTTCTGCTCCTGCCGGGACATCGCCTGCACAGAGCGGAGGCGACAGAC  785
     ||||||||||||||||||||||||||||||||| ||||| ||||||||||
 890 CTCTTCTGCTCCTGCCGGGACATCGCCTGCACCGAGCGGCGGCGACAGAC  939

786 CATCGTGCCTGTGTGCTCCTATGAAGAGAGGGAGAAGCCCAACTGTTTGA  835
     ||||| || ||||||||||||||||| ||  |||| ||||||||| ||||
 940 TATCGTCCCCGTGTGCTCCTATGAAGAACGAGAGAGGCCCAACTGCCTGA  989

836 ATTTGCAGGACTCCTGCAAGACGAATTACATCTGCAGATCTCGCCTTGCG  885
     | ||||| |||||||||||||| |||||||||||||||||||||||||||
 990 GTCTGCAAGACTCCTGCAAGACCAATTACATCTGCAGATCTCGCCTTGCA 1039

886 GATTTTTTTACCAACTGCCAGCCAGAGTCAAGGTCTGTCAGCAGCTGTCT  935
     ||||||||||||||||||||||||||||||||||||||||||| ||||||
1040 GATTTTTTTACCAACTGCCAGCCAGAGTCAAGGTCTGTCAGCAACTGTCT 1089

936 AAAGGAAAACTACGCTGACTGCCTCCTCGCCTACTCGGGGCTTATTGGCA  985
     ||||| |||||||| |||||||||||| ||||||||||| || |||||||
1090 TAAGGAGAACTACGCAGACTGCCTCCTGGCCTACTCGGGACTGATTGGCA 1139

986 CAGTCATGACCCCCAACTACATAGACTCCAGTAGCCTCAGTGTGGCCCCA 1035
     |||||||||| |||||||||| ||||||||| |||||||| |||||  ||
1140 CAGTCATGACTCCCAACTACGTAGACTCCAGCAGCCTCAGCGTGGCACCA 1189

1036 TGGTGTGACTGCAGCAACAGTGGGAACGACCTAGAAGAGTGCTTGAAATT 1085
     ||||||||||||||||||| || || ||||| ||||| |||||||||||
1190 TGGTGTGACTGCAGCAACAGCGGCAATGACCTGGAAGACTGCTTGAAATT 1239

1086 TTTGAATTTCTTCAAGGACAATACATGTCTTAAAAATGCAATTCAAGCCT 1135
     | ||||||| || |||||||||||| ||||| ||||||||||||||||||
1240 TCTGAATTTTTTAAGGACAATACTTGTCTCAAAAATGCAATTCAAGCCT 1289

1136 TTGGCAATGGCTCCGATGTGACCGTGTGGCAGCCAGCCTTCCCAGTACAG 1185
     ||||||||||||| ||||||||| |||||||||||||||  ||||| |||
1290 TTGGCAATGGCTCAGATGTGACCATGTGGCAGCCAGCCCCTCCAGTCCAG 1339

1186 ACCACCACTGCCACTACCACCACTGCCCTCCGGGTTAAGAACAAGCCCCT 1235
     ||||||||||||||| || ||||||||||  |||| |||||||||||  |
1340 ACCACCACTGCCACCACTACCACTGCCTTCCGGGTCAAGAACAAGCCTCT 1389

1236 GGGGCCAGCAGGGTCTGAGAATGAAATTCCCACTCATGTTTTGCCACCGT 1285
     |||||||||||||||||||||||| || ||||| || |||| ||||| |
1390 GGGGCCAGCAGGGTCTGAGAATGAGATCCCCACACACGTTTTACCACCCT 1439

1286 GTGCAAATTTACAGGCACAGAAGCTGAAATCCAATGTGTCGGGCAATACA 1335
     |||| |||||| ||||| ||||||||||||||||||||||||| || ||
1440 GTGCGAATTTGCAGGCTCAGAAGCTGAAATCCAATGTGTCGGGTAGCACA 1489

1336 CACCTCTGTATTTCCAATGGTAATTATGAAAAGAAGGTCTC...GGTGC 1382
     |||||||||  |||   ||  ||  |||  |||  ||||||   |||||
1490 CACCTCTGTCTTTCTGATAGTGATTTCGGAAAGGATGGTCTCGCTGGTGC 1539
```

FIG. 3A-2

```
1383 TTCCAGCCACATAACCACAAAATCAATGGCTGCTCCTCCAAGCTGTGGTC 1432
     ||||||||||||||||||||||||||||||||||||||||| ||||| |||
1540 CTCCAGCCACATAACCACAAAATCAATGGCTGCTCCTCCCAGCTGCAGTC 1589

1433 TGAGCCCACTGCTGGTCCTGGTGGTAACCGCTCTGTCCACCCTATTATCT 1482
     |||||  ||||||  |||  |||  ||  | ||||||  |  |||| ||||||
1590 TGAGCTCACTGCCGGTGCTGATGCTCACCGCCCTTGCTGCCCTGTTATCT 1639

1483 ......TTAACAGAAACATCATAGCTGCATTAAAAAAATACAATATGGAC 1526
            ||  ||||||||  || ||||||||||     ||| ||| ||||
1640 GTATCGTTGGCAGAAACGTCGTAGCTGCATCCGGGAAA.ACAGTATG... 1685

1527 ATGTAAAAGACAAA....AACCAAGTTATCTGTTTCTGTTCTCTTGTA 1572
     ||||||||||        ||||||||  |||| | ||||| ||||||||
1686 .....AAAAGACAAAAGAGAACCAAGTATTCTG.TCCCTGTCCTCTTGTA 1729

1573 TAGCTGAAATTCCAG.TTTAGGAGCTCAGTTGAGAAACAGTTCCATTCAA 1621
     || ||||||| |||||  |||| ||||| ||||||||| ||||| || |||
1730 TATCTGAAAATCCAGTTTTAAAAGCTCCGTTGAGAAGCAGTTTCACCCAA 1779

1622 CTGGAACATTTTTTTTTTTCCTTTTAAGAAAGCTTCTTGTGATCCTTCG 1671
     |||||||    | ||| || |||||||||| ||||||   |||  |  |
1780 CTGGAAC....TCTTTCCTTGTTTTAAGAAAG...CTTGTGGCCCTCAG 1822

1672 GGGCTTCTGT 1681
     ||||||||||
1823 GGGCTTCTGT 1832
```

FIG. 3A-3

```
  1 MFLATLYFALPLLDLLLSAEVSGGDRLDCVKASDQCLKEQSCSTKYRTLR  50
    ||||||||||||||||:|||||||||||||||||||||||||||||||||
  1 MFLATLYFALPLLDLLMSAEVSGGDRLDCVKASDQCLKEQSCSTKYRTLR  50

51 QCVAGKETNFSLASGLEAKDECRSAMEALKQKSLYNCRCKRGMKKEKNCL 100
    |||||||||||.||||||||||||||||||||||||||||||||||||||
 51 QCVAGKETNFSLTSGLEAKDECRSAMEALKQKSLYNCRCKRGMKKEKNCL 100

101 RIYWSMYQSLQGNDLLEDSPYEPVNSRLSDIFRVVPFIS.....VEHIPK 145
    |||||||||||||||||||||||||||||||||.|||||    ||||.|
101 RIYWSMYQSLQGNDLLEDSPYEPVNSRLSDIFRAVPFISDVFQQVEHISK 150

146 GNNCLDAAKACNLDDICKKYRSAYITPCTTSVSNDVCNRRKCHKALRQFF 195
    |||||||||||||.||||||||||||||||:||:||||||||||||||||
151 GNNCLDAAKACNLDDTCKKYRSAYITPCTTSMSNEVCNRRKCHKALRQFF 200

196 DKVPAKHSYGMLFCSCRDIACTERRRQTIVPVCSYEEREKPNCLNLQDSC 245
    |||||||||||||||||||||||||||||||||||||||:||||.|||||
201 DKVPAKHSYGMLFCSCRDIACTERRRQTIVPVCSYEERERPNCLSLQDSC 250

246 KTNYICRSRLADFFTNCQPESRSVSSCLKENYADCLLAYSGLIGTVMTPN 295
    |||||||||||||||||||||||||.||||||||||||||||||||||||
251 KTNYICRSRLADFFTNCQPESRSVSNCLKENYADCLLAYSGLIGTVMTPN 300

296 YIDSSSLSVAPWCDCSNSGNDLEECLKFLNFFKDNTCLKNAIQAFGNGSD 345
    |:|||||||||||||||||||||:||||||||||||||||||||||||||
301 YVDSSSLSVAPWCDCSNSGNDLEDCLKFLNFFKDNTCLKNAIQAFGNGSD 350

346 VTVWQPAFPVQTTTATTTTALRVKNKPLGPAGSENEIPTHVLPPCANLQA 395
    ||:|||| |||||||||||:||||||||||||||||||||||||||||||
351 VTMWQPAPPVQTTTATTTTAFRVKNKPLGPAGSENEIPTHVLPPCANLQA 400

396 QKLKSNVSGNTHLCISNGNYEKEGL.GASSHITTKSMAAPPSCGLSPLLV 444
    ||||||||.||||:|::::|:||    |||||||||||||||||:||.| |
401 QKLKSNVSGSTHLCLSDSDFGKDGLAGASSHITTKSMAAPPSCSLSSLPV 450

445 LVVTALSTLL..SLTETS 460
    |::|||..||  ||.|||
451 LMLTALAALLSVSLAETS 468
```

FIG. 3B

```
  1 AAAAAACGGTGGGATTTATTTAACATGATCTTGGCAAACGTCTTCTGCCT    50
                                  M  I  L  A  N  V  F  C  L

51 CTTCTTCTTTCTAGACGAGACCCTCCGCTCTTTGGCCAGCCCTTCCTCCC   100
     F  F  F  L  D  E  T  L  R  S  L  A  S  P  S  S  L

101 TGCAGGGCCCCGAGCTCCACGGCTGGCGCCCCCAGTGGACTGTGTCCGG    150
     Q  G  P  E  L  H  G  W  R  P  P  V  D  C  V  R

151 GCCAATGAGCTGTGTGCCGCCGAATCCAACTGCAGCTCTCGCTACCGCAC   200
     A  N  E  L  C  A  A  E  S  N  C  S  S  R  Y  R  T

201 TCTGCGGCAGTGCCTGGCAGGCCGCGACCGCAACACCATGCTGGCCAACA   250
     L  R  Q  C  L  A  G  R  D  R  N  T  M  L  A  N  K

251 AGGAGTGCCAGGCGGCCTTGGAGGTCTTGCAGGAGAGCCCGCTGTACGAC   300
     E  C  Q  A  A  L  E  V  L  Q  E  S  P  L  Y  D

301 TGCCGCTGCAAGCGGGGCATGAAGAAGGAGCTGCAGTGTCTGCAGATCTA   350
     C  R  C  K  R  G  M  K  K  E  L  Q  C  L  Q  I  Y

351 CTGGAGCATCCACCTGGGGCTGACCGAGGGTGAGGAGTTCTACGAAGCCT   400
     W  S  I  H  L  G  L  T  E  G  E  E  F  Y  E  A  S

401 CCCCCTATGAGCCGGTGACCTCCCGCCTCTCGGACATCTTCAGGCTTGCT   450
     P  Y  E  P  V  T  S  R  L  S  D  I  F  R  L  A

451 TCAATCTTCTCAGGGACAGGGGCAGACCCGGTGGTCAGCGCCAAGAGCAA   500
     S  I  F  S  G  T  G  A  D  P  V  V  S  A  K  S  N

501 CCATTGCCTGGATGCTGCCAAGGCCTGCAACCTGAATGACAACTGCAAGA   550
     H  C  L  D  A  A  K  A  C  N  L  N  D  N  C  K  K

551 AGCTGCGCTCCTCCTACATCTCCATCTGCAACCGCGAGATCTCGCCCACC   600
     L  R  S  S  Y  I  S  I  C  N  R  E  I  S  P  T

601 GAGCGCTGCAACCGCCGCAAGTGCCACAAGGCCCTGCGCCAGTTCTTCGA   650
     E  R  C  N  R  R  K  C  H  K  A  L  R  Q  F  F  D

651 CCGGGTGCCCAGCGAGTACACCTACCGCATGCTCTTCTGCTCCTGCCAAG   700
     R  V  P  S  E  Y  T  Y  R  M  L  F  C  S  C  Q  D

701 ACCAGGCGTGCGCTGAGCGCCGCCGGCAAACCATCCTGCCCAGCTGCTCC   750
     Q  A  C  A  E  R  R  R  Q  T  I  L  P  S  C  S

751 TATGAGGACAAGGAGAAGCCCAACTGCCTGGACCTGCGTGGCGTGTGCCG   800
     Y  E  D  K  E  K  P  N  C  L  D  L  R  G  V  C  R

801 GACTGACCACCTGTGTCGGTCCCGGCTGGCCGACTTCCATGCCAATTGTC   850
     T  D  H  L  C  R  S  R  L  A  D  F  H  A  N  C  R
```

FIG. 7a

```
851  GAGCCTCCTACCAGACGGTCACCAGCTGCCCTGCGGACAATTACCAGGCG  900
      A  S  Y  Q  T  V  T  S  C  P  A  D  N  Y  Q  A

901  TGTCTGGGCTCTTATGCTGGCATGATTGGGTTTGACATGACACCTAACTA  950
      C  L  G  S  Y  A  G  M  I  G  F  D  M  T  P  N  Y

951  TGTGGACTCCAGCCCCACTGGCATCGTGGTGTCCCCCTGGTGCAGCTGTC  1000
      V  D  S  S  P  T  G  I  V  V  S  P  W  C  S  C

1001 GTGGCAGCGGGAACATGGAGGAGGAGTGTGAGAAGTTCCTCAGGGACTTC  1050
      G  S  G  N  M  E  E  E  C  E  K  F  L  R  D  F

1051 ACCGAGAACCCATGCCTCCGGAACGCCATCCAGGCCTTTGGCAACGGCAC  1100
      T  E  N  P  C  L  R  N  A  I  Q  A  F  G  N  G  T

1101 GGACGTGAACGTGTCCCCAAAAGGCCCCTCGTTCCAGGCCACCCAGGCCC  1150
      D  V  N  V  S  P  K  G  P  S  F  Q  A  T  Q  A  P

1151 CTCGGGTGGAGAAGACGCCTTCTTTGCCAGATGACCTCAGTGACAGTACC  1200
      R  V  E  K  T  P  S  L  P  D  D  L  S  D  S  T

1201 AGCTTGGGGACCAGTGTCATCACCACCTGCACGTCTGTCCAGGAGCAGGG  1250
      S  L  G  T  S  V  I  T  T  C  T  S  V  Q  E  Q  G

1251 GCTGAAGGCCAACAACTCCAAAGAGTTAAGCATGTGCTTCACAGAGCTCA  1300
      L  K  A  N  N  S  K  E  L  S  M  C  F  T  E  L  T

1301 CGACAAATATCATCCCAGGGAGTAACAAGGTGATCAAACCTAACTCAGGC  1350
      T  N  I  I  P  G  S  N  K  V  I  K  P  N  S  G

1351 CCCAGCAGAGCCAGACCGTCGGCTGCCTTGACCGTGCTGTCTGTCCTGAT  1400
      P  S  R  A  R  P  S  A  A  L  T  V  L  S  V  L  M

1401 GCTGAAACTGGCCTTGTAGGCTGTGGGAACCGAGTCAGAAGATTTTTGAA  1450
      L  K  L  A  L

1451 AGCTACGCAGACAAGAACAGCCGCCTGACGAAATGGAAACACACACAGAC  1500

1501 ACACACACACCTTGCAAAAAAAAAATTGTTTTTCCCACCTTGTCGCTGAA  1550

1551 CCTGTCTCCTCCCAGGTTTCTTCTCTGGAGAAGTTTTTGTAAACCAAACA  1600

1601 GACAAGCAGGCAGGCAGCCTGAGAGCTGGCCCAGGGGTCCCCTGGCAGGG  1650

1651 GAAACTCTGGTGCCGGGGAGGGCACGAGGCTCTAGAAATGCCCTTCACTT  1700

1701 TCTCCTGGTGTTTTTCTCTCTGGACCCTTCTGAAGCAGAGACCGGACAAG  1750

1751 AGCCTGCAGCGGAAGGGACTCTGGGCTGTGCCTGAGGCTGGCTGGGGCA  1800

1801 GGACAACACAGCTGCTTCCCCAGGCTGCCCACTCTGGGGACCGCTGGGG  1850

1851 GCTGGCAGAGGGCATCGGTCAGCGGGGCAGCGGGGCTG 1888
```

FIG. 7b

```
  1 MILANVFCLFFFLDETLRSLASPSSLQGPELHGWRPPVDCVRANELCAAE  50
    |:||.::    : :||   |.. .|:.           .:|||:|.: |  |
  1 MFLATLYFALPLLDLLLSAEVSGGD...........RLDCVKASDQCLKE  39

51 SNCSSRYRTLRQCLAGRDRN.....TMLANKECQAALEVLQESPLYDCRC  95
    .||.:|||||||:||::  |      .:|..||..|:|.|.:..||:|||
 40 QSCSTKYRTLRQCVAGKETNFSLASGLEAKDECRSAMEALKQKSLYNCRC  89

96 KRGMKKELQCLQIYWSIHLGLTEGEEFYEASPYEPVTSRLSDIFRLASIF 145
    ||||||  .||.||||::. :|  :|:::.|.|||||.||||||||:..:
 90 KRGMKKEKNCLRIYWSMYQSL.QGNDLLEDSPYEPVNSRLSDIFRVVPFI 138

146 SGTGADPVVSAKSNHCLDAAKACNLNDNCKKLRSSYISICNREISPTERC 195
    |..         :|:|:|||||||||||:|  |||.||.||.  |. .:|  .: |
139 SVEHI.....PKGNNCLDAAKACNLDDICKKYRSAYITPCTTSVS.NDVC 182

196 NRRKCHKALRQFFDRVPSEYTYRMLFCSCQDQACAERRRQTILPSCSYED 245
    ||||||||||||||:||....|  ||||||.|  ||.|||||||||:|  ||||:
183 NRRKCHKALRQFFDKVPAKHSYGMLFCSCRDIACTERRRQTIVPVCSYEE 232

246 KEKPNCLDLRGVCRTDHLCRSRLADFHANCRASYQTVTSCPADNYQACLG 295
    :|||||:|.: |:|:..:||||||||| .||.:.  ..|.|| :||..||
233 REKPNCLNLQDSCKTNYICRSRLADFFTNCQPESRSVSSCLKENYADCLL 282

296 SYAGMIGFDMTPNYVDSSPTGIVVSPWCSCRGSGNMEEECEKFLRDFTEN 345
    .|.|:||  ||||||:|||  ::  |.|||.|..||| |||  ||| . |.:|
283 AYSGLIGTVMTPNYIDSS...SLSVAPWCDCSNSGNDLEECLKFLNFFKDN 330

346 PCLRNAIQAFGNGTDVNVSPKGPSFQATQAPRVEKTPSLPDDLSDSTS.. 393
    .||:|||||||||.||.|...:   ..|.| |.  .    ..|:....|
331 TCLKNAIQAFGNGSDVTVWQPAFPVQTTTATTTTALRVKNKPLGPAGSEN 380

394 .LGTSVITTCTSVQEQGLKANNS..KELSMCFTELTTTNIIPGSNKVIKPN 440
    :.|  |:..|...:.|  ||.|  |    ..|:::  .:....  ::|..........
381 EIPTHVLPPCANLQAQKLKSNVSGNTHLCISNGNYEKEGLGASSHITTKS 430

441 SGPSRARPSAALTVLSVLMLKLAL 464
    ::...  ..:|  ||| |  |.  |
431 MAAPPSCGLSPLLVLVVTALSTLL 454
```

FIG. 8

```
  1  CGCAGGCAGAGCGCTGTCGCATCCCGGGCGTCCACCCGCCATGGGGCTCT   50
                                                  M  G  L  S

51  CCTGGAGCCCGCGACCTCCACTGCTGATGATCCTGCTACTGGTGCTGTCG  100
      W  S  P  R  P  P  L  L  M  I  L  L  L  V  L  S

101  TTGTGGCTGCCACTTGGAGCAGGAAACTCCCTTGCCACAGAGAACAGGTT  150
      L  W  L  P  L  G  A  G  N  S  L  A  T  E  N  R  F

151  TGTGAACAGCTGTACCCAGGCCAGAAAGAAATGCGAGGCTAATCCCGCTT  200
      V  N  S  C  T  Q  A  R  K  K  C  E  A  N  P  A  C

201  GCAAGGCTGCCTACCAGCACCTGGGCTCCTGCACCTCCAGTTTAAGCAGG  250
      K  A  A  Y  Q  H  L  G  S  C  T  S  S  L  S  R

251  CCGCTGCCCTTAGAGGAGTCTGCCATGTCTGCAGACTGCCTAGAGGCAGC  300
      P  L  P  L  E  E  S  A  M  S  A  D  C  L  E  A  A

301  AGAACAACTCAGGAACAGCTCTCTGATAGACTGCAGGTGCCATCGGCGCA  350
      E  Q  L  R  N  S  S  L  I  D  C  R  C  H  R  R  M

351  TGAAGCACCAAGCTACCTGTCTGGACATTTATTGGACCGTTCACCCTGCC  400
      K  H  Q  A  T  C  L  D  I  Y  W  T  V  H  P  A

401  CGAAGCCTTGGTGACTACGAGTTGGATGTCTCACCCTATGAAGACACAGT  450
      R  S  L  G  D  Y  E  L  D  V  S  P  Y  E  D  T  V

451  GACCAGCAAACCCTGGAAAATGAATCTTAGCAAGTTGAACATGCTCAAAC  500
      T  S  K  P  W  K  M  N  L  S  K  L  N  M  L  K  P

501  CAGACTCGGACCTCTGCCTCAAATTTGCTATGCTGTGTACTCTTCACGAC  550
      D  S  D  L  C  L  K  F  A  M  L  C  T  L  H  D

551  AAGTGTGACCGCCTGCGCAAGGCCTACGGGGAGGCATGCTCAGGGATCCG  600
      K  C  D  R  L  R  K  A  Y  G  E  A  C  S  G  I  R

601  CTGCCAGCGCCACCTCTGCCTAGCCCAGCTGCGCTCCTTCTTTGAGAAGG  650
      C  Q  R  H  L  C  L  A  Q  L  R  S  F  F  E  K  A

651  CAGCAGAGTCCCACGCTCAGGGTCTGCTGCTGTGTCCCTGTGCACCAGAA  700
      A  E  S  H  A  Q  G  L  L  L  C  P  C  A  P  E

701  GATGCGGGCTGTGGGGAGCGGCGGCGTAACACCATCGCCCCCAGTTGCGC  750
      D  A  G  C  G  E  R  R  R  N  T  I  A  P  S  C  A

751  CCTGCCTTCTGTAACCCCCAATTGCCTGGATCTGCGGAGCTTCTGCCGTG  800
      L  P  S  V  T  P  N  C  L  D  L  R  S  F  C  R  A

801  CGGACCCTTTGTGCAGATCACGCCTGATGGACTTCCAGACCCACTGTCAT  850
      D  P  L  C  R  S  R  L  M  D  F  Q  T  H  C  H

851  CCTATGGACATCCTTGGGACTTGTGCAACTGAGCAGTCCAGATGTCTGCG  900
      P  M  D  I  L  G  T  C  A  T  E  Q  S  R  C  L  R
```

FIG. 9a

```
 901  GGCATACCTGGGGCTGATTGGGACTGCCATGACCCCAAACTTCATCAGCA   950
       A  Y  L  G  L  I  G  T  A  M  T  P  N  F  I  S  K
 951  AGGTCAACACTACTGTTGCCTTAAGCTGCACCTGCCGAGGCAGCGGCAAC  1000
       V  N  T  T  V  A  L  S  C  T  C  R  G  S  G  N
1001  CTACAGGACGAGTGTGAACAGCTGGAAAGGTCCTTCTCCCAGAACCCCTG  1050
       L  Q  D  E  C  E  Q  L  E  R  S  F  S  Q  N  P  C
1051  CCTCGTGGAGGCCATTGCAGCTAAGATGCGTTTCCACAGACAGCTCTTCT  1100
       L  V  E  A  I  A  A  K  M  R  F  H  R  Q  L  F  S
1101  CCCAGGACTGGGCAGACTCTACTTTTTCAGTGGTGCAGCAGCAGAACAGC  1150
       Q  D  W  A  D  S  T  F  S  V  V  Q  Q  Q  N  S
1151  AACCCTGCTCTGAGACTGCAGCCCAGGCTACCCATTCTTTCTTTCTCCAT  1200
       N  P  A  L  R  L  Q  P  R  L  P  I  L  S  F  S  I
1201  CCTTCCCTTGATTCTGCTGCAGACCCTCTGGTAGCTGGGCTTCCTCAGGG  1250
       L  P  L  I  L  L  Q  T  L  W
1251  TCCTTTGTCCTCTCCACCACACCCAGACTGATTTGCAGCCTGTGGTGGGA  1300
1301  GAGAACTCGCCAGCCTGTGGAAGAAGACGCAGCGTGCTACACAGCAACCC  1350
1351  GGAACCAACCAGGCATTCCGCAGCACATCCGTCTGCTCCAGAAGAGGTC   1400
1401  TTAGAAGTGAGGGCTGTGACCCTTCCGATCCTGAGCGGCTAGTTTTCAAA  1450
1451  CCTCCCTTGCCCCTGCTTCCTTCTGGCTCAGGCTGCTCCTCCTTAGGACT  1500
1501  TTGTGGGTCCAGTTTTGCCTTCTGTTCTGATGGTGATTAGCGGCTCACCT  1550
1551  CCAGCGCTTCTTCCTGTTTCCCAGGACCACCCAGAGGCTAAGGAATCAGT  1600
1601  CATTCCCTGTTGCCTTCTCCAGGAAGGCAGGCTAAGGGTTCTGAGGTGAC  1650
1651  TGAGAAAAATGTTTCCTTTGTGTGGAAGGCTGGTGCTCCAGCCTCCACGT  1700
1701  CCCTCTGAATGGAAGATAAAAACCTGCTGGTGTCTTGACTGCTCTGCCAG  1750
1751  GCAATCCTGAACATTTGGGCATGAAGAGCTAAAGTCTTTGGGTCTTGTTT  1800
1801  AACTCCTATTACTGTCCCCAAATTCCCCTAGTCCCTTGGGTCATGATTAA  1850
1851  ACATTTTGACTTAAAAAAAAAAAAAAAAAAAAAAAAAA  1889
```

FIG. 9b

```
  1  TGTGGACGCGCGCTTCGGAGTTGGAGGGCGGCGCCCAGGACCCTGGTGGG    50

51  AGAGTGTGTGCGTCGCGCTGGAGGGCGGGAGGCGGGGGCGGGAGGTGCCG   100

101  GTCGAGGGAGCCCCGCTCTCAGAGCTCCAGGGGAGGAGCGAGGGGAGCGC   150

151  GGAGCCCGGCGCCTACAGCTCGCCATGGTGCGCCCCCTGAACCCGCGACC   200
                              M  V  R  P  L  N  P  R  P

201  GCTGCCGCCCGTAGTCCTGATGTTGCTGCTGCTGCCGCCGTCGCCGC      250
      L  P  P  V  V  L  M  L  L  L  L  P  P  S  P  L

251  TGCCTCTCGCAGCCGGAGACCCCCTTCCCACAGAAAGCCGACTCATGAAC    300
      P  L  A  A  G  D  P  L  P  T  E  S  R  L  M  N

301  AGCTGTCTCCAGGCCAGGAGGAAGTGCCAGGCTGATCCCACCTGCAGTGC    350
      S  C  L  Q  A  R  R  K  C  Q  A  D  P  T  C  S  A

351  TGCCTACCACCACCTGGATTCCTGCACCTCTAGCATAAGCACCCCACTGC    400
      A  Y  H  H  L  D  S  C  T  S  S  I  S  T  P  L  P

401  CCTCAGAGGAGCCTTCGGTCCCTGCTGACTGCCTGGAGGCAGCACAGCAA    450
      S  E  E  P  S  V  P  A  D  C  L  E  A  A  Q  Q

451  CTCAGGAACAGCTCTCTGATAGGCTGCATGTGCCACCGGCGCATGAAGAA    500
      L  R  N  S  S  L  I  G  C  M  C  H  R  R  M  K  N

501  CCAGGTTGCCTGCTTGGACATCTATTGGACCGTTCACCGTGCCCGCAGCC    550
      Q  V  A  C  L  D  I  Y  W  T  V  H  R  A  R  S  L

551  TTGGTAACTATGAGCTGGATGTCTCCCCCTATGAAGACACAGTGACCAGC    600
      G  N  Y  E  L  D  V  S  P  Y  E  D  T  V  T  S

601  AAACCCTGGAAAATGAATCTCAGCAAACTGAACATGCTCAAACCAGACTC    650
      K  P  W  K  M  N  L  S  K  L  N  M  L  K  P  D  S

651  AGACCTCTGCCTCAAGTTTGCCATGCTGTGTACTCTCAATGACAAGTGTG    700
      D  L  C  L  K  F  A  M  L  C  T  L  N  D  K  C  D

701  ACCGGCTGCGCAAGGCCTACGGGGAGGCGTGCTCCGGGCCCCACTGCCAG    750
      R  L  R  K  A  Y  G  E  A  C  S  G  P  H  C  Q

751  CGCCACGTCTGCCTCAGGCAGCTGCTCACTTTCTTCGAGAAGGCCGCCGA    800
      R  H  V  C  L  R  Q  L  L  T  F  F  E  K  A  A  E

801  GCCCCACGCGCAGGGCCTGCTACTGTGCCCATGTGCCCCCAACGACCGGG    850
      P  H  A  Q  G  L  L  L  C  P  C  A  P  N  D  R  G

851  GCTGCGGGGAGCGCCGGCGCAACACCATCGCCCCCAACTGCGCGCTGCCG    900
      C  G  E  R  R  R  N  T  I  A  P  N  C  A  L  P

901  CCTGTGGCCCCCAACTGCCTGGAGCTGCGGCGCCTCTGCTTCTCCGACCC    950
      P  V  A  P  N  C  L  E  L  R  R  L  C  F  S  D  P
```

FIG. 10a

```
 951  GCTTTGCAGATCACGCCTGGTGGATTTCCAGACCCACTGCCATCCCATGG  1000
       L   C   R   S   R   L   V   D   F   Q   T   H   C   H   P   M   D
1001  ACATCCTAGGAACTTGTGCAACAGAGCAGTCCAGATGTCTACGAGCATAC  1050
       I   L   G   T   C   A   T   E   Q   S   R   C   L   R   A   Y
1051  CTGGGGCTGATTGGGACTGCCATGACCCCCAACTTTGTCAGCAATGTCAA  1100
       L   G   L   I   G   T   A   M   T   P   N   F   V   S   N   V   N
1101  CACCAGTGTTGCCTTAAGCTGCACCTGCCGAGGCAGTGGCAACCTGCAGG  1150
       T   S   V   A   L   S   C   T   C   R   G   S   G   N   L   Q   E
1151  AGGAGTGTGAAATGCTGGAAGGGTTCTTCTCCCACAACCCCTGCCTCACG  1200
       E   C   E   M   L   E   G   F   F   S   H   N   P   C   L   T
1201  GAGGCCATTGCAGCTAAGATGCGTTTTCACAGCCAACTCTTCTCCCAGGA  1250
       E   A   I   A   A   K   M   R   F   H   S   Q   L   F   S   Q   D
1251  CTGGCCACACCCTACCTTTGCTGTGATGGCACACCAGAATGAAAACCCTG  1300
       W   P   H   P   T   F   A   V   M   A   H   Q   N   E   N   P   A
1301  CTGTGAGGCCACAGCCCTGGGTGCCCTCTCTTTTCTCCTGCACGCTTCCC  1350
       V   R   P   Q   P   W   V   P   S   L   F   S   C   T   L   P
1351  TTGATTCTGCTCCTGAGCCTATGGTAGCTGGACTTCCCCAGGGCCCTCTT  1400
       L   I   L   L   L   S   L   W
1401  CCCCTCCACCACACCCAGGTGGACTTGCAGCCCACAAGGGGTGAGGAAAG  1450
1451  GACAGCAGCAGGAAGGAGGTGCAGTGCGCAGATGAGGGCACAGGAGAAGC  1500
1501  TAAGGGTTATGACCTCCAGATCCTTACTGGTCCAGTCCTCATTCCCTCCA  1550
1551  CCCCATCTCCACTTCTGATTCATGCTGCCCCTCCTTGGTGGCCACAATTT  1600
1601  AGCCATGTCATCTGGTGCCTGTGGGCCTTGCTTTATTCCTATTATTGTCC  1650
1651  TAAAGTCTCTCTGGGCTCTTGGATCATGATTAAACCTTTGACTTAAAAA  1699
```

FIG. 10b

RET LIGAND (RETL) FOR STIMULATING NEUTRAL AND RENAL GROWTH

RELATED APPLICATIONS

This is a continuation-in-part of prior application PCT/US97/07726, filed on May 7, 1997, the teachings of which are incorporated herein by reference which is a continuation-in-part of prior application U.S. Ser. No. 60/043,533, filed Apr. 11, 1997, and a continuation-in-part of prior application U.S. Ser. No. 60/023,444, filed Aug. 23, 1996, and a continuation-in-part of prior application U.S. Ser. No. 60/021,859, filed Jul. 16, 1996, and a continuation-in-part of prior application U.S. Ser. No. 60/019,300, filed Jun. 7, 1996, and a continuation-in-part of prior application U.S. Ser. No. 60/017,427, filed May 8, 1996.

FIELD OF THE INVENTION

This invention relates to nucleotide sequences which encode a Ret ligand (RetL), as well as to methods of stimulating neural and renal growth by treating cells and mammalian subjects with Red, DNA or protein.

BACKGROUND OF THE INVENTION

One of the goals of current research on cell signaling and receptor activation is to enable therapeutic modulation of processes involved in cell growth and survival. Such processes determine outcome in diverse medical conditions, including organ failure, fetal development, and tumor growth, among others. Each of these conditions is of worldwide clinical importance, and has limited efficacious treatment options. It is an object of the invention to provide compositions and methods for promoting regeneration or survival of damaged tissue, as well as for treating disorders involving the aberrant growth and development of tissues.

Tissue loss or end-stage organ failure affects millions of people worldwide each year and adds substantially to health care costs. Organ or tissue loss is usually treated by transplanting organs from donors, by surgical reconstruction, or with mechanical devices. Each of these remedies has shortcomings. Transplantation is limited by donor shortage, surgical reconstruction can create other long-term problems, and mechanical devices cannot perform all the functions of a single organ, and therefore cannot prevent progressive deterioration. Thus, a real medical need exists for new solutions to these problems.

Protein factors that affect the growth, differentiation and/or survival of cells may be useful in the treatment of disorders of organs which contain responsive cells. Factors or ligands that interact with receptors of the receptor protein tyrosine kinase (RPTK) family are of particular interest in this regard. These receptors are involved in many cellular programs including cell growth and differentiation, and the genesis of many neoplasias. Thus the factors or ligands that interact with these receptors may prove useful in treating disorders of certain organs where the tissue has been damaged. Alternatively, it may be useful to block the interaction of these factors with their receptors in order to block tumor growth.

The Ret proto-oncogene encodes a receptor tyrosine kinase that is expressed during development in a variety of tissues, including the peripheral and central nervous systems and the kidney. The abnormalities present in ret null mice suggest that Ret is critical for the migration and innervation of enteric neurons to the hindgut, and for proliferation and branching of the ureteric bud epithelium during kidney development (Nature 367, 380–383, 1994). The search for a key component of the Ret signaling pathway, the Ret ligand, has been an area of intensive research.

SUMMARY OF THE INVENTION

The invention provides a purified and isolated DNA molecule coding for a RetL, having the nucleotide sequence of any RetL, but specifically including rat retL1 cDNA (SEQ ID NO:1), partial human retL1 cDNA (SEQ ID NO:8), full-length human retL1 cDNA (SEQ ID NO:10), human retL2 cDNA (SEQ ID NO:12), murine retL3 cDNA (SEQ ID NO:16), partial human retL3 cDNA (SEQ ID NO:18) or human retL3 cDNA (SEQ ID NO:20). The invention further provides a RetL protein, with an amino acid sequence comprising that of rat RetL1 (SEQ ID NO:2), partial human RetL1 (SEQ ID NO:9), full-length human RetL1 (SEQ ID NO:11), human RetL2 (SEQ ID NO:13), murine RetL3 (SEQ ID NO:17), partial human RetL3 (SEQ ID NO:19) or human RetL3 (SEQ ID NO:21).

In another embodiment, the invention includes a DNA sequence which encompasses the sequence (partial human retL1 cDNA (SEQ ID NO:8)) of the insert DNA of clone HRL20, which is ATCC No. 97604, or the sequence of the insert DNA of clone #230-5A-86-17 (rat retL1 cDNA (SEQ ID NO:1)), which is ATCC No. 98047.

In another embodiment of the invention, a purified and isolated DNA molecule for use in securing expression in a prokaryotic or eukaryotic host cell of a polypeptide product has at least a part of the primary structural conformation and the biological activity of RetL; the DNA may be a) a DNA molecule which comprises rat retL1 cDNA, partial human retL1 cDNA, full-length hum an retL1 cDNA, human retL2 cDNA, murine retL3 cDNA or human retL3 cDNA, or the complementary strand of rat retL1 cDNA, partial human retL1 cDNA, full-length human retL1 cDNA, human retL2 cDNA, murine retL3 cDNA or human retL3 cDNA; b) DNA molecules which hybridize under stringent conditions to the DNA molecules defined in a) or fragments thereof; or c) DNA molecules which, but for the degeneracy of the genetic code, would hybridize to the DNA molecules defined in a) and b). A purified and isolated DNA molecule coding for a polypeptide fragment or variant of a human RetL having the biological activity of a RetL is also within the invention.

Any of the recombinant DNA molecules of the invention may be operably linked to an expression control sequence.

Also included within the invention are vectors and delivery systems which encompass the DNA molecules or constructs defined elsewhere in this specification. The vector may encompass a DNA molecule encoding a RetL or a variant of a RetL.

The invention includes prokaryotic or eukaryotic host cells stably transformed or transfected by a vector comprising a DNA molecule encoding a native or variant RetL.

A purified and isolated human RetL substantially free of other human proteins is specifically within the invention, as is a process for the production of a polypeptide product having part or all of the primary structural conformation and the biological activity of a RetL. Such a process may include the steps of growing, under suitable culture conditions, prokaryotic or eukaryotic host cells transformed or transfected with any DNA molecule of the invention, in a manner allowing expression of such polypeptide product, and recovering a RetL. The polypeptide product of the expression in a procaryotic or eukaryotic host cell of a DNA is also included.

The invention also includes proteins and protein fragments, variants and derivatives, whether soluble or membrane bound. In selected embodiments, the protein has an amino acid sequence which comprises rat RetL1, partial human RetL1, full-length human RetL1, human RetL2, murine RetL3, or human RetL3, or is a variant of one of these sequences. In other embodiments, the protein is a fusion protein including Ret or a RetL, fused to another molecule or molecular fragment, such as an immunoglobulin, toxin, imageable compound or radionuclide. Also included are chimeric molecules of RetL.

Other embodiments of the invention include specific monoclonal antibodies to a RetL of the invention. Such an antibody may be associated with a toxin, imageable compound or radionuclide. The invention also includes hybridoma cell lines which produce specific antibodies to Ret, including AA.FF9, AA.HE3, AF.E9, BA.B1, BB.B6, AA.GE7, CD.F11, AH.E3, CD.G4, AG.E7, BD.G6 and BH.G8, as well as subclones of these hybridomas, and the antibodies produced by these hybridomas or subclones of these hybridomas.

The invention further includes a method of promoting growth of new tissue, or promoting survival of damaged tissue in a subject, including administering to the subject a therapeutically effective amount of a compound which interacts with cellular Ret and thereby induces autophosphorylation of Ret. The compound may be RetL1, RetL2, or RetL3, a fragment of a full-length RetL, or an antibody which binds to Ret. The compound may be administered concurrently with a therapeutically effective amount of a second compound, such as GDNF, neurturin or a GDNF-related molecule. While tissues of interest for these methods may include any tissue, preferred tissues include renal tissue, neural tissue, heart, stomach, small intestine, spinal cord, or lung. In one embodiment, the RetL is a soluble RetL. The subject of the methods may be human.

In another method of the invention, Ret signal transduction between a first cell expressing a RetL and a second cell is inhibited by contacting the first cell with a soluble Ret protein or with an antibody to the RetL. The soluble Ret protein may be a fusion protein.

The invention also includes a method for targeting a toxin, imageable compound or radionuclide to a cell expressing Ret, encompassing contacting the cell with a RetL fusion protein or an anti-Ret antibody conjugated to a toxin, imageable compound or radionuclide. The. Ret can be RetL1, RetL2 or RetL3. In another method, growth of a tumor cell which expresses Ret is suppressed, with a step of the method being contacting the cell with a fusion protein of a RetL and a toxin or radionuclide, or an anti-Ret antibody conjugated to a toxin or radionuclide. The cell may be within a subject, and the protein or the conjugated antibody is administered to the subject.

Also encompassed within the invention is a method for targeting a toxin, imageable compound or radionuclide to a cell expressing a RetL, comprising contacting the cell with a fusion protein comprising Ret and a toxin, imageable compound or radionuclide, or an anti-RetL antibody conjugated to a toxin, imageable compound or radionuclide. Another embodiment includes the method of suppressing growth of a tumor cell which expresses a RetL, comprising contacting the cell with a fusion protein of Ret and a toxin or radionuclide or with an anti-RetL antibody conjugated to a toxin or radionuclide; the cell may be within a subject, and the protein administered to the subject.

The RetL for any of the methods of the invention can be RetL1, RetL2 or RetL3, or a variant or fragment of RetL1, RetL2 or RetL3.

Methods of gene therapy are also within the invention. One embodiment is a method of treating a subject with a disorder of Ret metabolism, comprising administering to the subject a vector comprising a DNA molecule encoding a RetL, as well as a method of promoting growth of new tissue in a subject, comprising administering such a vector to the subject. Another embodiment includes a method of promoting survival of damaged tissue in a subject, one step of the method being administering a therapeutically effective amount of a vector encoding a RetL to the subject.

BRIEF DESCRIPTION OF THE DRAWINGS

FIGS. 1a and 1b are a cDNA sequence (SEQ ID NO:1) and deduced amino acid sequence (SEQ ID NO:2) of rat RetL1. The nucleotide sequence extends from base pair 201 through base pair 1700 of SEQ ID NO:1, and contains the entire open reading frame.

FIGS. 2A-1 and 2A-2 are a partial cDNA sequence (SEQ ID NO:8) and deduced amino acid sequence (SEQ ID NO:9) of human RetL1. This sequence is that of the insert of clone HRL20, deposited as ATCC No. 97604.

FIGS. 2B-1 and 2B-2 are a composite full-length DNA sequence (SEQ ID NO:10) and deduced amino acid sequence (SEQ ID NO:11) of human RetL1.

FIGS. 3A-1, 3A-2 and 3A-3 are a comparison of the nucleotide sequence of human RetL1 (upper line of sequence) with that of rat RetL1 sequence (lower line of sequence). Vertical lines between nucleotides show identity at a position, while a dot indicates a gap at that position.

FIG. 3B is a comparison of the amino acid sequence of human RetL1 (upper line of sequence) with that of rat RetL1 sequence (lower line of sequence). Vertical lines between corresponding amino acids show identity at a residue, while a dot indicates a conservative substitution at that residue.

FIGS. 7a and 7b are a cDNA sequence (SEQ ID NO:12) and deduced amino acid sequence (SEQ ID NO:13) of human retL2, as found in clone DSW240. The protein reading frame is contained within nucleotides 25 to 1416.

FIG. 8 is a comparison of the amino acid sequence of human RetL2 (upper line of sequence) with that of human RetL1 sequence (lower line of sequence). Vertical lines between amino acids show identity at a position, while a dot indicates a gap at that position.

FIGS. 9a and 9b are a cDNA sequence (SEQ ID NO:16) and deduced amino acid sequence (SEQ ID NO:17) of murine RetL3.

FIGS. 10a and 10b are a cDNA sequence (SEQ ID NO:20) and deduced amino acid sequence (SEQ ID NO:21) of human RetL3.

DETAILED DESCRIPTION OF THE INVENTION

Sequence Identification Numbers

Figure 4A:
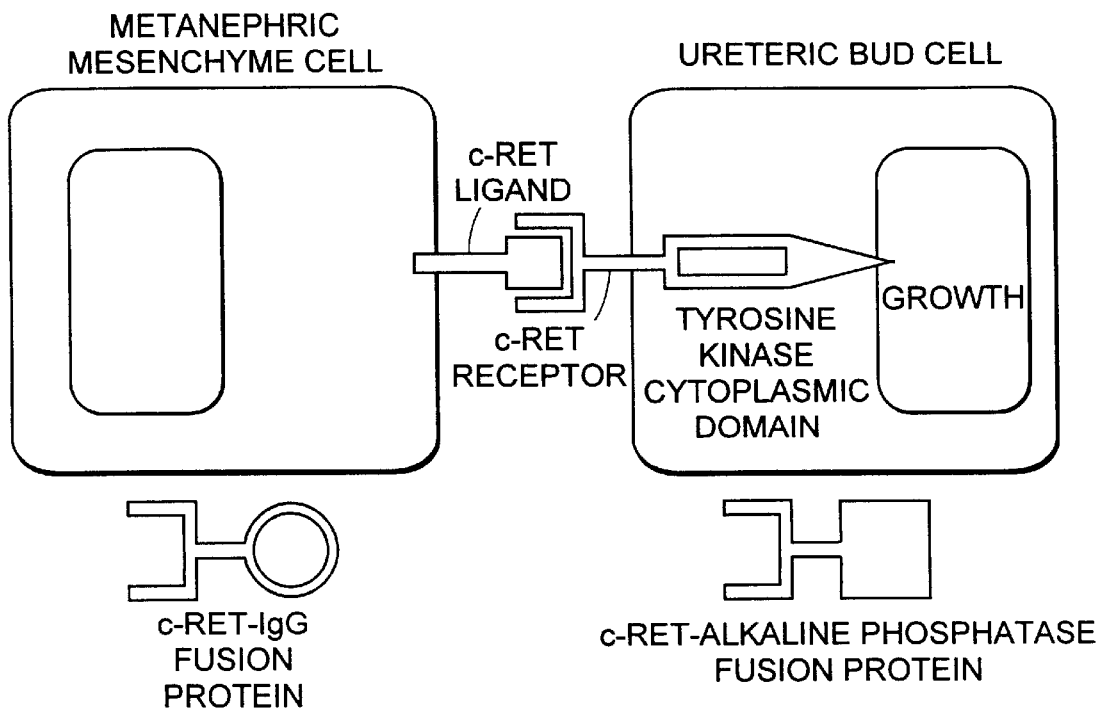
FIG. 4A is a schematic diagram of a possible role for Ret and RetL in the interaction between a metanephric mesenchyme cell and a ureteric bud cell.

Nucleotide and amino acid sequences referred to in the specification have been given the following sequence identification numbers:

SEQ ID NO:1—rat retL1 cDNA
SEQ ID NO:2—rat RetL1 aa
SEQ ID NO:3—oligomer kid-13
SEQ ID NO:4—oligomer kid-14
SEQ ID NO:5—oligomer kid-15
SEQ ID NO:6—extracellular rat ret cDNA
SEQ ID NO:7—extracellular rat Ret aa
SEQ ID NO:8—partial human retL1 cDNA
SEQ ID NO:9—partial human RetL1 aa
SEQ ID NO:10—human retL1 cDNA
SEQ ID NO:11—human RetL1 aa
SEQ ID NO:12—human retL2 cDNA
SEQ ID NO:13—human RetL2 aa
SEQ ID NO:14—partial murine retL3 cDNA (EST AA050083)
SEQ ID NO:15—partial murine RetL3 aa
SEQ ID NO:16—murine retL3 cDNA
SEQ ID NO:17—murine RetL3 aa
SEQ ID NO:18—partial human retL3 cDNA
SEQ ID NO:19—partial human RetL3 aa
SEQ ID NO:20—human retL3 cDNA
SEQ ID NO:21—human retL3 aa Definitions As used herein, the term "RetL" means any protein which specifically interacts with the receptor protein Ret, and which when it interacts with Ret triggers Ret dimerization and/or autophosphorylation of the tyrosine kinase domain of Ret. The DNA sequences which code for RetL and for Ret are termed "retL" and "ret", respectively. A ligand may be soluble, or present as a membrane-bound molecule on the same or on a different cell as the Ret molecule for which it is triggering autophosphorylation. In certain uses or interactions with Ret, the ligand may require additional molecules to trigger autophosphorylation. Ligands of the invention include co-receptors or accessory ligand cofactors. Ligands of the invention further include anti-Ret mAbs which act as Ret antagonists, triggering Ret dimerization and autophosphorylation. The ligand may also be modified in various ways, such as incorporated as a portion of a fusion protein, such as with a toxin or radionuclide.

By "alignment of sequences" is meant the positioning of one sequence, either nucleotide or amino acid, with that of another, to allow a comparison of the sequence of relevant portions of one with that of the other. An example of one method of this procedure is given in Needleman et al. (J. Mol. Biol. 48:443453, 1970). The method may be implemented conveniently by computer programs such as the Align program (DNAstar, Inc.). As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines, but do not materially impair their relationship in the folded structure of the protein. Therefore, internal gaps and amino acid insertions in the candidate sequence are ignored for purposes of calculating the level of amino acid sequence homology or identity between the candidate and reference sequences. One characteristic frequently used in establishing the homology of proteins is the similarity of the number and location of the cysteine residues between one protein and another.

By "icloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise a representation of the mRNA molecules present in an entire organism or tissue, depending on the source of the RNA templates. Such a cDNA library may be prepared by methods known to those of skill, and described, for example, in Maniatis et al., *Molecular Cloning: A Laboratory Manual*, supra. Generally, RNA is first isolated from the cells of an organism from whose genome it is desired to clone a particular gene. Preferred for the purposes of the present invention are mammalian, and particularly human, cell lines. Alternatively, RNA may be isolated from a tumor cell, derived from an animal tumor, and preferably from a human tumor. Thus, a library may be prepared from, for example, a human adrenal tumor, but any tumor may be used.

As used herein, the term "DNA polymorphism" refers to the condition in which two or more different nucleotide sequences can exist at a particular site in DNA.

"Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. A useful, but not a necessary, element of an effective expression vector is a marker encoding sequence, which is a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. Such vectors are frequently in the form of plasmids, so "plasmid" and "expression vector" are often used interchangeably. However, the invention is intended to include such other forms of expression vectors, including phage, which serve equivalent functions and which may from time to time become known in the art.

Similarly, a "functional derivative" of a gene of any of the proteins of the present invention is meant to include "fragments", "variants", and "analogues" of the gene, which may be "substantially similar" in nucleotide sequence, and which encode a molecule possessing similar activity.

"GDNF-related molecule" means any moleule which is at least 40% homologous to either GDNF or neurturin, and is also capable of specifically binding a RetL.

The term "gene" means a polynucleotide sequence encoding a peptide.

By "homogeneous" is meant, when referring to a peptide or DNA sequence, that the primary molecular structure (i.e., the sequence of amino acids or nucleotides) of substantially all molecules present in the composition under consideration is identical.

The term "oligonucleotide" as used herein in referring to probes, oligomer fragments to be detected, oligomer controls, unlabeled blocking oligomers and primers for amplification of sequences is defined as a molecule comprised of more than three deoxyribonucleotides or ribonucleotides. Its exact size will depend on many factors, which in turn depend on the ultimate function or use of the oligonucleotide.

The term "probe" refers to a ligand of known qualities capable Of selectively binding to a target antiligand. As applied to nucleic acids, the term "probe" refers to a strand of nucleic acid having a base sequence complementary to a target strand.

"Recombinant host cells" refers to cells which have been transformed with vectors constructed using recombinant DNA techniques. As defined herein, the antibody or modification thereof produced by a recombinant host cell is by virtue of this transformation, rather than in such lesser amounts, or more commonly, in such less than detectable amounts, as would be produced by the untransformed host.

As used herein, the terms "restriction endonucleases" and "restriction enzymes" refer to bacterial enzymes each of which cut double-stranded DNA at or near a specific nucleotide sequence.

As used herein, the term "restriction fragment length polymorphism" ("RFLP") refers to the differences among individuals in the lengths of a particular restriction fragment.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th ed., Mack Publishing Co:, Easton, Pa. (1980).

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible.

By "substantially pure" is meant any protein of the present invention, or any gene encoding any such protein, which is essentially free of other proteins or genes, respectively, or of other contaminants with which it might normally be found in nature, and as such exists in a form not found in nature.

Compounds of the Invention

The invention includes cDNA coding for a RetL, such as the nucleotide sequence of rat retL1 cDNA, partial human retL1 cDNA, full-length human retL1 cDNA, human retL2 cDNA, murine retL3 cDNA or human retL3 cDNA. In addition, the compounds of the invention include sequences which include the above sequences, or are derivatives of one of these sequences. The invention also includes vectors, liposomes and other carrier vehicles which encompass one of these sequences or a derivative of one of these sequences. The invention also includes proteins transcribed and translated from rat retL1 cDNA, partial human retL1 cDNA, full-length human retL1 cDNA, human retL2 cDNA, murine retL3 cDNA or human retL3 cDNA, including but not limited to rat RetL1, partial human RetL1, full-length human RetL1, human RetL2, murine RetL3, or human RetL3, and their derivatives and variants.

One embodiment of the invention includes soluble variants of a RetL. Soluble variants lack at least a portion of the intramembrane section of the native RetL. In some examples, the soluble variant lacks the phosphatidylinositol glycan linkage of the native RetL. Soluble variants include fusion proteins which encompass derivatives of RetL that lack a phosphatidylinositol motif.

Variants can differ from naturally occurring RetL in amino acid sequence or in ways that do not involve sequence, or both. Variants in amino acid sequence are produced when one or more amino acids in naturally occurring RetL is substituted with a different natural amino acid, an amino acid derivative or non-native amino acid. Particularly preferred variants include naturally occurring RetL, or biologically active fragments of naturally occurring RetL, whose sequences differ from the wild type sequence by one or more conservative amino acid substitutions, which typically have minimal influence on the secondary structure and hydrophobic nature of the protein or peptide. Variants may also have sequences which differ by one or more non-conservative amino acid substitutions, deletions or insertions which do not abolish the RetL biological activity. Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from the table below, and yet others are described by Dayhoff in the Atlas of Protein Sequence and Structure (1988).

TABLE 1

| CONSERVATIVE AMINO ACID REPLACEMENTS | | |
|---|---|---|
| For Amino Acid | Code | Replace with any of |
| Alanine | A | D-Ala, Gly, beta-Ala, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspardc Acid | D | D-Asp, D-Asn, Asn, Glu, D-Glu, Gln, D-Gln |

TABLE 1-continued

CONSERVATIVE AMINO ACID REPLACEMENTS

| For Amino Acid | Code | Replace with any of |
|---|---|---|
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3, 4 or 5-phenylproline, cis 3, 4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met)O, D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D- instead of L-amino acids into the polypeptide may increase its resistance to proteases. See, e.g., U.S. Pat. No. 5,219,990.

The peptides of this invention may also be modified by various changes such as insertions, deletions and substitutions, either conservative or nonconservative where such changes might provide for certain advantages in their use. Splice variants are specifically included in the invention.

In addition to substantially full-length polypeptides, the present invention provides for biologically active fragments of the polypeptides. A RetL polypeptide or fragment is biologically active if it exhibits a biological activity of naturally occurring RetL. Such biological activities include the ability to specifically bind the extracellular portion of Ret, with an affinity that is at least 50% of, and preferably at least equal to, the affinity of naturally occurring RetL for the extracellular portion of Ret. Another biological activity is the ability to bind to an antibody which is directed at an epitope which is present on naturally occurring RetL.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bully side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Generally, substitutions that may be expected to induce changes in the functional properties of Ret polypeptides are those in which: (I) a hydrophilic residue, e.g., serine or threonine, is substituted by a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative charge, e.g., glutamic acid or aspartic acid; or (iv) a residue having a bulky side chain, e.g., phenylalanine, is substituted for (or by) one not having such a side chain, e.g., glycine.

Variants within the scope of the invention include proteins and peptides with amino acid sequences having at least sixty percent homology with rat RetL1 (SEQ ID NO:2), partial human RetL1 (SEQ ID NO:9), full-length human RetL1 (SEQ ID NO:1 1), human RetL2 (SEQ ID NO:13), murine RetL3 (SEQ ID NO:17), partial human RetL3 (SEQ ID NO:19) or human RetL3 (SEQ ID NO:21). More preferably the sequence homology is at least eighty, at least ninety percent, or at least ninety-five percent. For the purposes of determining homology the length of comparison sequences will generally be at least 8 amino acid residues, usually at least amino acid residues. Variants of the compounds of the invention also includes any protein which 1) has an amino acid sequence which is at least forty percent homologous to a RetL protein of the invenion, and also which 2) after being placed in an optimal alignment with the RetL sequence (as depicted for RetL1 and RetL2 in FIG. 8), has at least 80% of its cysteine residues alligned with cysteines in the RetL protein of the invention.

Just as it is possible to replace substituents of the scaffold, it is also possible to substitute functional groups which are bound to the scaffold with groups characterized by similar features. Such modifications do not alter primary sequence. These will initially be conservative, i.e., the replacement group will have approximately the same size, shape, hydrophobicity and charge as the original group. Non-sequence modifications may include, for example, in vivo or in vitro chemical derivatization of portions of naturally occurring RetL, as well as changes in acetylation, methylation, phosphorylation, carboxylation or glycosylation.

Also included within the invention are agents which specifically bind to a protein of the invention, or a fragment of such a protein. These agents include Ig fusion proteins and antibodies (including single chain, double chain, Fab fragments, and others, whether native humanized, primatized, or chimeric). Additional descriptions of these categories of agents are in PCT application 95/16709, the specification of which is herein incorporated by reference.

EXPERIMENTAL PROCEDURE

Overview of Strategy

Figure 4B:
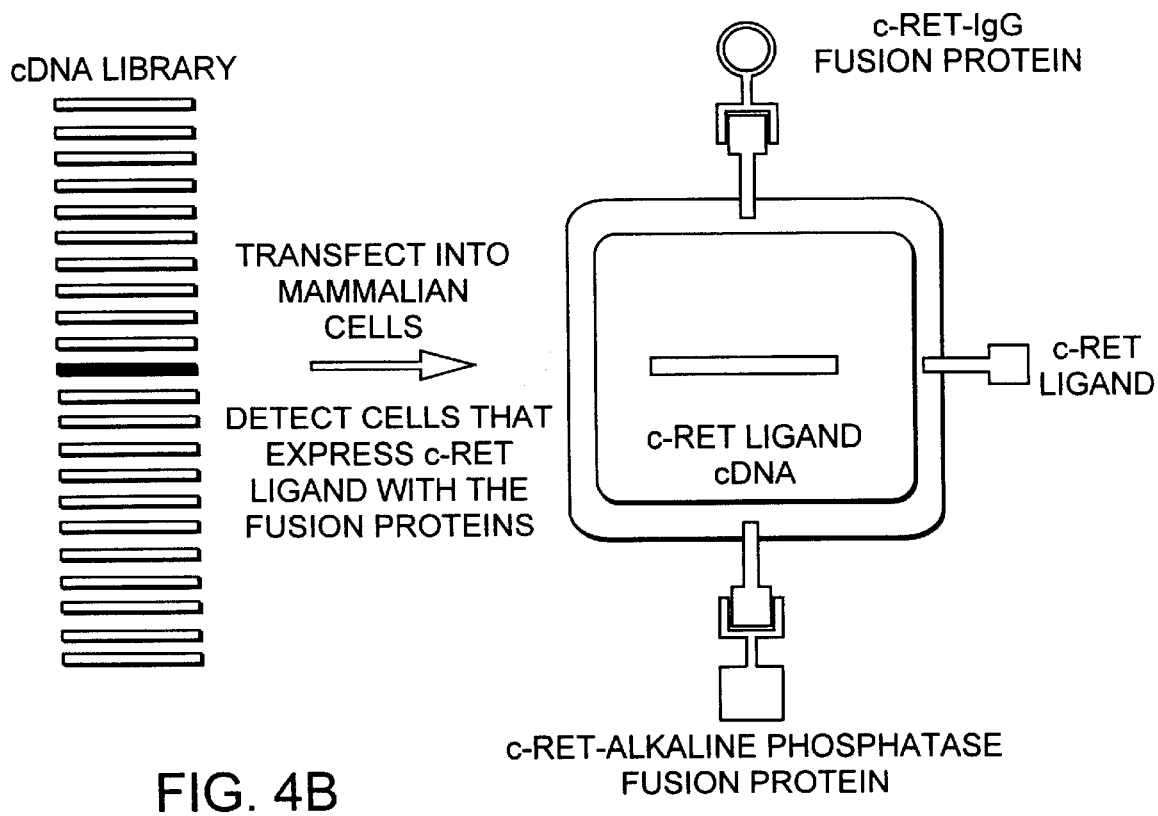
FIG. 4B is a schematic diagram of a method of screening transfectants of a cDNA library for clones that express a RetL. The presence of expressed RetL on transfectants is detected by assessing the binding by those transfectants either of Ret/IgG fusion protein or of Ret/alkaline phosphatase fusion protein.

The general strategy used to clone RetL1 is shown in FIGS. 4A and 4B. Our strategy was based on the premise that at least a RetL is expressed on the metanephric mesenchyme of the developing kidney as a membrane protein (although it is possible that the ligand is also expressed in a soluble form; FIG. 4A). The RetL interacts with the Ret receptor on the ureteric bud cell, activating its tyrosine kinase cytoplasmic domain and sending a signal to the nucleus, which in turn activates genes involved in the growth and branching of the ureteric bud. Therefore, proteins containing the extracellular domain of Ret fused to either the $F_c$ portion of human immunoglobulin G1 (IgG1) or alkaline phosphatase (AP) can be used as part of a strategy to clone RetL as shown in FIG. 4B. The fusion proteins, the expression libraries and other reagents used in the cloning of RetL1 are described below.

We first isolate a cDNA for rat RetL1 and then use it as a probe to isolate a cDNA for human RetL1. cDNAs are subsequently isolated for RetL2 and RetL3.

Generation of Reagents Required for Direct Expression Cloning of Ret Ligands

1. Isolation of cDNA Encoding Rat Ret Extracellular Domain

To identify RetL1, fusion proteins are generated consisting of the extracellular domains of either rat or human Ret fused to a protein, in one example the human Fc portion of IgG1, and in another example alkaline phosphatase. Both fusion partners can be easily assayed to detect cells which express the ligand as illustrated in FIG. 4B.

Since a cDNA coding for rat Ret has never been disclosed, we isolate a cDNA encoding the extracellular domain of the rat Ret receptor using the Reverse Transcriptase-Polymerase Chain Reaction (RT-PCR) method. We compare the two nucleotide sequences for human (Genbank Accession numbers M57464 and X15262) and murine (Genbank Accession number X67812) ret and design oligonucleotide primers from regions of high identity between the two sequences. A sense oligomer called kid-013 (SEQ ID NO:3; contains nucleotides 150–169 of Genbank sequence X15262) is chosen from the 5' end of the human ret cDNA sequence overlapping the ATG initiation codon. It includes nucleotides on its 5' end encoding a NotI restriction site for the purpose of cloning. Two antisense oligomers called kid-014 (SEQ ID NO:4; contains the complement of nucleotides 1819–1839 of Genbank sequence M57464) and kid-015 (SEQ ID NO:5; contains the complement of nucleotides 1894–1914 of Genbank sequence X67812) are chosen, respectively, from the human and murine cDNA sequences immediately 5' to the sequences that encode the transmembrane domains. Oligomers kid-014 and kid-015 contain additional nucleotides at their 5' ends that encode a SalI restriction site for the purpose of cloning.

Total RNA is isolated from the day 14 embryonic rat kidney and mRNA is purified using oligo-dT chromatography. mRNA is converted to cDNA using AMV reverse transcriptase and the cDNA is converted to double stranded cDNA and amplified using Taq polymerase in a standard polymerase chain reaction with oligomers kid-013 and kid-015. The synthesis of a 1942 bp PCR fragment is confirmed by running an aliquot of the PCR reaction on a 1% agarose gel. The rest of the PCR fragment is digested with NotI and SalI and cloned into pSAB132 previously digested with NotI and SalI. The resulting plasmid is called pJC011. The entire insert of plasmid pJC011 contained between the NotI and SalI sites is sequenced, and is shown as extracellular rat ret cDNA, SEQ ID NO:6. A translation of this sequence reveals the peptide sequence (SEQ ID NO:7) for extracellular rat Ret. Because oligomers for PCR were chosen from human and mouse sequences of ret, it is possible that the nucleotide sequence shown as that of extracellular rat ret cDNA, and the peptide sequence shown as that of extracellular rat Ret, may differ from the natural rat ret nucleotide and Ret peptide sequences in the,regions of kid-013 and kid-015 sequences. Subsequently, ret cDNA clones are isolated from a day 18 rat embryonic kidney cDNA library and a few nucleotide changes are observed in the primer regions resulting in two amino acid changes. One change is in the signal sequence (arginine at position 5 to threonine) and one change is near the end of the extracellular domain (glutamic acid at position 633 to alanine). Both of these changes should not affect ligand binding.

2. Ret/IgG Fusion Proteins

Fusion proteins are generated consisting of the extracellular domains of the rat (aa residues #1-637) and human (aa residues #1-636) Ret receptors fused to the Fc portion of human IgG1.

Figure 5:
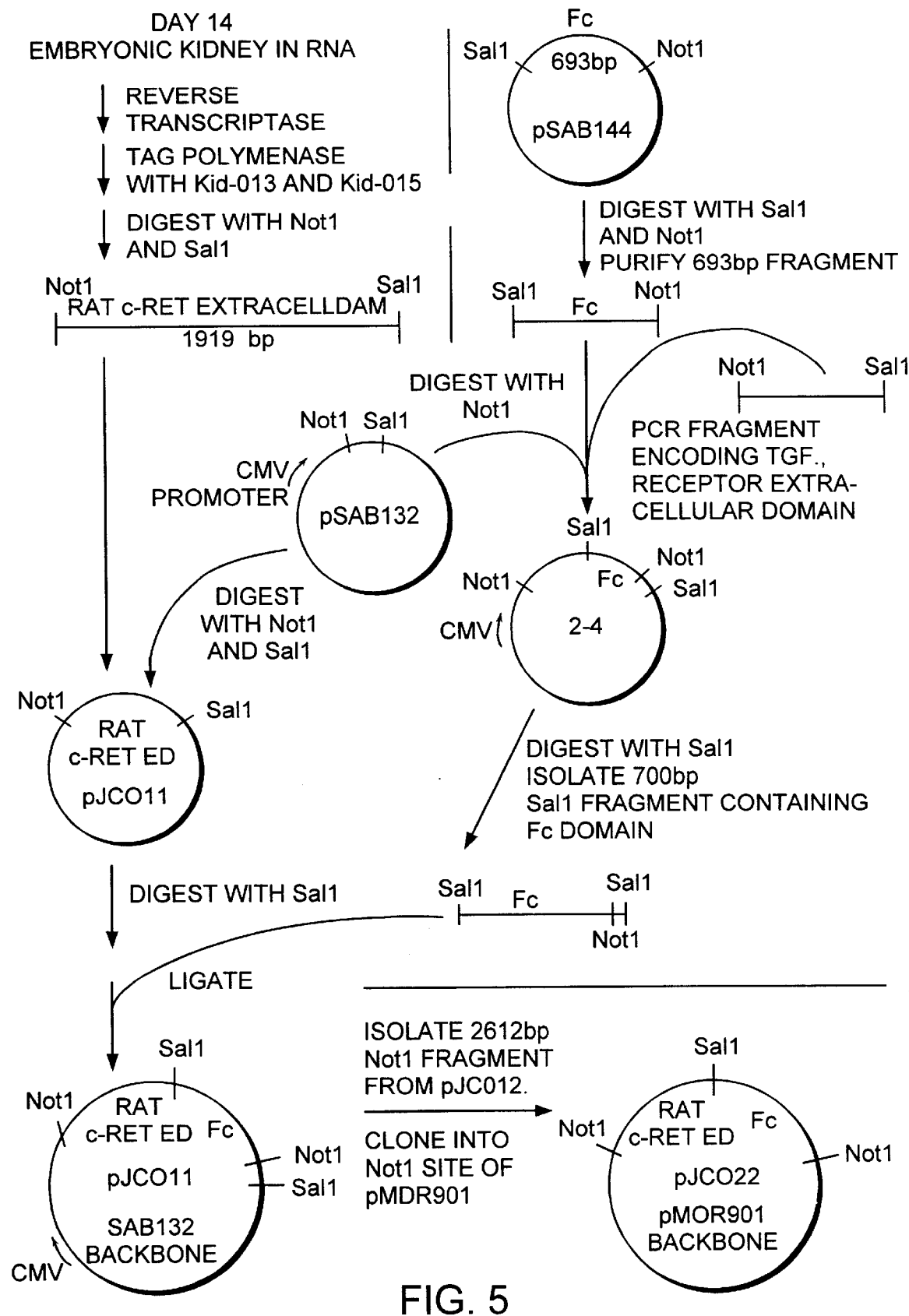
FIG. 5 is a schematic diagram showing the construction of the plasmids used to express the rat Ret/IgG fusion protein.

The construction of the plasmids used to express the rat Ret/IgG fusion protein is shown schematically in FIG. 5. In order to construct a gene encoding the rat Ret/IgG fusion protein, we digest pJC011 (described above) containing the rat Ret extracellular domain with SalI, and ligate it to a 700 bp SalI fragment from plasmid 2–4, to create plasmid pJC012. This SalI fragment contains part of the Fc domain of human IgG1 originally derived from plasmid pSAB144. Plasmid 2–4 was created previously via a three way ligation: a NotI—SalI fragment generated by PCR containing the extracellular domain of the rabbit TGF-beta type II receptor; a 693 bp SalI—NotI fragment from pSAB 144 containing part of the Fc domain of human. IgG1; and NotI digested pSAB132. As shown in FIG. 5, a fragment containing the Fc domain can be released from the 2–4 plasmid as a 700 bp SalI fragment. pJC012 is tansfected into COS cells and the rat Ret/IgG fusion protein is purified from the medium 48 hrs later using Protein-A Sepharose chromatography. In order to make a stable cell line producing the rat Ret/IgG protein, the 2612 bp NotI fragment from pJC012 containing the entire rat Ret/IgG fusion protein is isolated and cloned into the NotI site of expression vector pMDR901. The resulting plasmid is called pJC022. Plasmid pJC022 is transfected into CHO cells to generate stable cell lines. The highest producing cell line is suspension adapted. Typical yields for the rat Ret/IgG CHO line are 75 mg/L.

Figure 6:
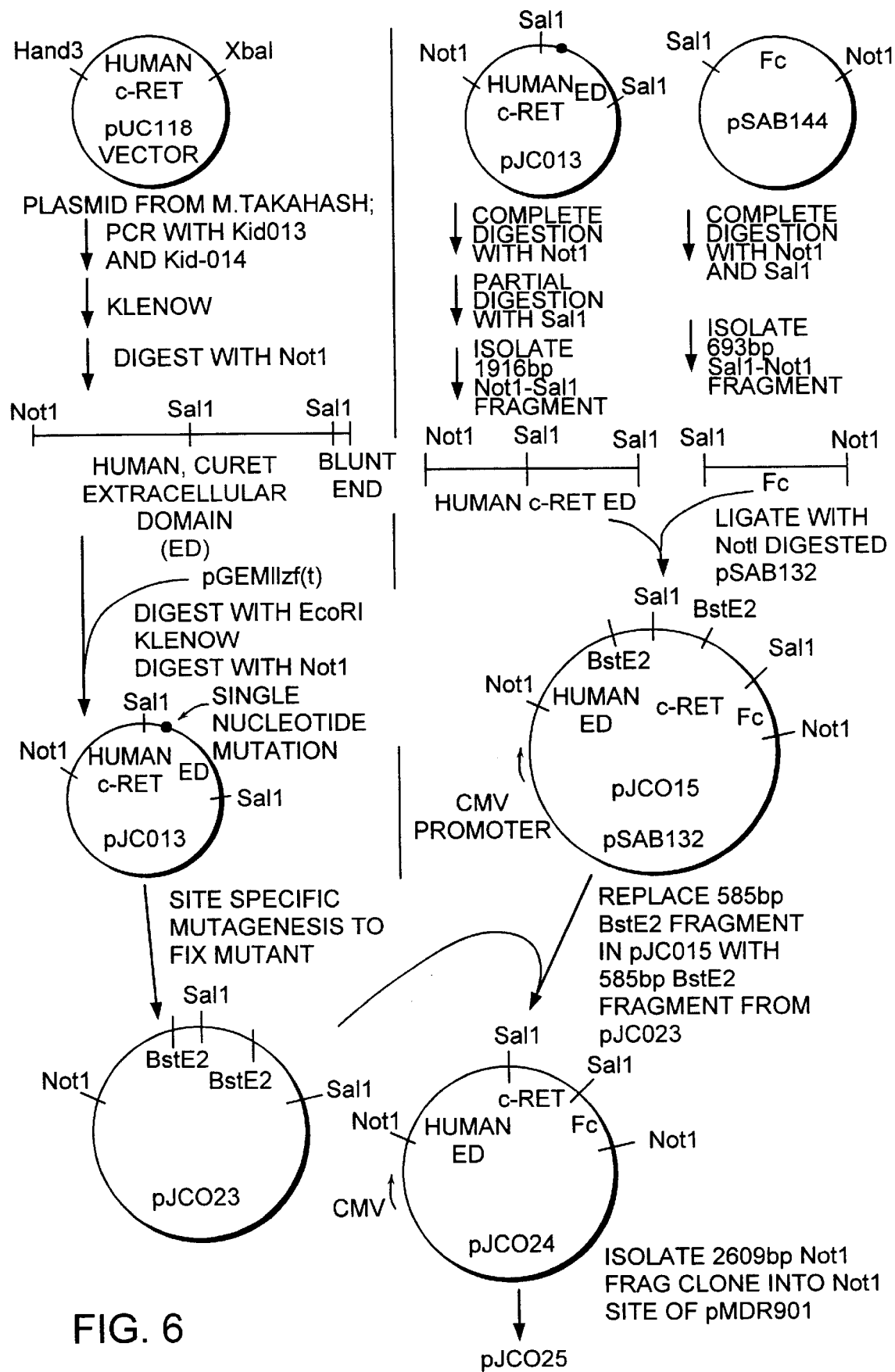
FIG. 6 is a schematic diagram showing the construction of the plasmids used to express the human Ret/IgG fusion protein.

The construction of the plasmids used to express the human Ret/IgG fusion protein is shown schematically in FIG. 6. In order to construct a gene encoding the human Ret/IgG fusion protein, we obtain a plasmid containing a cDNA encoding the human Ret receptor from Dr. M. Takahashi (Department of Pathology, Nagoya University, School of Medicine, Nagoya, Japan). A PCR fragment is generated from this plasmid using oligomers kid-013 and kid-014. The PCR fragment is treated with Klenow fragment followed by digestion with NotI to produce a PCR fragment with a sticky NotI end and one blunt end. This fragment is cloned into the vector pGEMIIzf(+) previously digested with EcoRI, treated with Klenow fragment, and digested with NotI, in order to generate a sticky NotI end and one blunt end. The resulting plasmid is called pJC013. The 1916 bp NotI—SalI fragment from pJC013 is isolated after a complete digestion with NotI and a partial digestion with SalI, and ligated to the 693 bp SalI—NotI fragment from pSAB144 containing part of the Fc domain of human IgG1, and the pSAB132 expression vector digested with NotI. The resulting plasmid is called pJC015. The insert in plasmid pJC013 is sequenced and found to contain a single nucleotide difference which changes one amino acid in the extracellular domain of human Ret (Genbank sequence M57464 has a C at position 812, whereas pJC013 has a T at the corresponding position; this results in a change in amino acids from alanine to valine at position 294 of the human Ret protein sequence). This nucleotide is corrected back to the C residue specified by Genbank sequence M57464 by site specific mutagenesis of plasmid pJC013, producing plasmid pJC023. A 585 bp BstE2 fragment from pJC023 containing the repaired nucleotide sequence is isolated and cloned into plasmid pJC015 from which the 585 bp BstE2 fragment containing the variant nucleotide has been removed. The new plasmid is called pJC024. The 2609 bp NotI fragment from pJC024 containing the entire human Ret/IgG fusion protein is isolated and cloned into the NotI site of expression vector pMDR901. The resulting plasmid is called pJC025. Plasmid pJC025 is transfected into CHO cells to generate stable cell lines. The highest producing cell line is suspension adapted. Typical yields for the human Ret/IgG CHO line are 6 mg/L.

Further details on production of the vectors employed in the methods of the invention are given in PCT applications 94/01456 and 92/02050, the specifications of which are herein incorporated by reference.

3. Bioactivity of the Ret/IgG Fusion Proteins

To determine if the Ret/IgG fusion proteins that we produce are bioactive and therefore would be good screening reagents for the cloning of a RetL, we perform several organ culture assays for bioactivity. The organ culture assay consists of growing day 13–14 embryonic rat kidneys in organ culture for 3–5 days in the presence of the Ret/Ig fusion protein at a concentration of 50 ug/ml. Kidneys are also cultured in the presence of LFA-3TIP/IgG or vehicle buffer. After the culture period, some of the kidneys are stained with the fluorescent lectin Dolichos Biflorus Agglutinin (DB lectin) which stains the collecting duct tissues, which are epithelial cells derived from the ureteric bud. These "DB" positive cells mark the Ret-positive cells, since Ret is expressed in the ureteric bud and its epithelial derivatives. This provides a gross assessment of the Ret/IgG fusion protein on the growth and development of the embryonic kidney. There is a clear difference in collecting duct morphology and growth between kidneys which have been cultured with LFA-3TIP and those cultured with the rat Ret/IgG fusion protein. The Ret/IgG-treated kidneys have collecting ducts which show significantly less branching and are typically smaller overall.

Paraffin sections are prepared from other kidneys for histological examination. Embryonic kidneys are treated with control buffer or with Ret/IgG, then stained with hematoxylin and eosin. The Ret/Ig-treated embryonic kidney exhibits less branching of the collecting ducts than the control buffer-treated embryonic kidneys. In addition, Ret/IgG-treated kidneys have fewer tubules. We have also observed this effect with the human Ret/IgG fusion protein. These observations are consistent with the fusion proteins blocking the inductive signal between the mesenchyme and the ureteric bud. Therefore we conclude that the fusion protein is a good reagent for cloning a RetL.

4. Ret/alkaline Phosphatase Fusion Protein

Receptor/alkaline phosphatase (AP) fusion proteins have been used successfully to identify and clone ligands for c-kit (Cell 63:185, 1990), ligands for members of the eph family of orphan receptors (Cell 79:157, 1994), and recently to clone a receptor for leptin, the product of the ob gene (Cell 83:1263, 1995). Plasmids encoding the rat Ret/AP fusion protein are constructed and the rat Ret/AP protein is produced in COS7 cells in cell factories. Subsequently, a stable NIH3T3 cell line is generated expressing on average 10 mg/L of fusion protein. SDS-PAGE analysis of the rat Ret/AP protein indicates that its size is consistent with the predicted molecular weight, and gel filtration analysis indicates that it is produced as a dimer. Partial purification is achieved by affinity chromatography on an anti-AP column.

5. Anti-Ret Antibodies

A rabbit polyclonal antibody is generated against the rat Ret/IgG fusion protein. The antibody works on Western blots, FACS analysis of Ret positive cell lines, and immunohistochemistry of embryonic kidney sections.

A panel of hamster anti-rat Ret monoclonal antibodies is generated. Rat Ret/IgG fusion protein, coupled to Protein A Sepharose, is used to immunize Armenian hamsters. 316 clones are obtained after the fusion and screened for their ability to bind rat Ret fusion proteins and/or human IgG in an ELISA assay. 11 clones produce antibodies that bind only to rat Ret/IgG (and rat Ret/AP), but not human IgG. The cross reactivity to human Ret is assayed by FACS; four clones produce antibodies that can bind to the Ret positive human cell line THP-1. The following table summarizes the Ret binding properties of twelve monoclonal antibodies.

| Clone | ELISA rat Ret/Ig | FACS human THP-1 |
|---|---|---|
| AA.FF9.5 | + | − |
| AA.HE3.7 | + | + |
| AF.E9.5 | + | − |
| BA.B1.16 | + | − |
| BB.B6 | + | − |
| AA.GE7.3 | + | − |
| CD.F11.2 | + | − |
| AH.E3.11 | + | + |
| CD.G4.2 | + | + |
| AG.E7.9 | + | − |
| BD.G6 | + | + |
| BH.G8 | − | − |

6. cDNA Expression Libraries

We prepare cDNA libraries from rat embryonic kidney, one in the CDM8 vector which utilizes the SV40 origin for amplification, and one in a modified In Vitrogen vector, pCEP4, which utilizes the EBV origin for amplification. This modified vector, CH269, has the EBNA-1 gene sequence removed. The EBNA-1 protein interacts, with the EBV origin, but the gene is not needed on the vector when cells are used which stably express the EBNA protein. The library in the CDM8 vector contains $1.5 \times 10^6$ clones with an average insert size of 1.18 kb, while the library in the CH269 vector contains approximately $1 \times 10^6$ clones with an average insert size of 1.5 kb.

Expression Cloning of Ret Ligand RetL1

A. Cloning of Rat Ret Ligand RetL1

1. Initial Attempts at Cloning of Ret Ligand RetL1

A number of direct expression methods have been tried to clone RetL1. All of these methods are based on the concept illustrated in FIG. 4B. cDNAs from a cDNA library are introduced into mammalian cells; cells that receive RetL1 can be identified using the Ret fusion proteins. Although the three approaches described below were unsuccessful, important knowledge and expertise was acquired, which was deployed in a subsequent approach that met with success.

a. Panning Method with Ret/IgG—The rat Ret/IgG fusion protein is used in an attempt to isolate RetL1 by direct expression cloning using a panning method (Aruffo and Seed, Proc. Natl. Acad. Sci. 84: 8753–8757 (1987)). A day 18 embryonic rat kidney cDNA library in CDM8 is used for the panning effort. Pools of cDNAs from this library (5,000–10,000 cDNAs per pool) are introduced into COS cells using the DEAE-dextran method. After 48 hours, the cells are removed from the plates with EDTA, incubated with the fusion protein, and subsequently panned on plates coated with anti-human IgG$_1$ antibody. DNA is recovered from cells that adhered, transformed back into E. coli, and subsequently isolated for a second round of panning. We are unable to see any cells bind after the third round of panning, and very few clones are obtained after transformation of the Hirt DNA back into E. Coli. A VCAM cDNA, used in conjunction with an anti-VCAM monoclonal antibody as a positive control, could only be diluted to a ratio of 1:100 and still be detected, indicating that our pool sizes are probably too large. Analysis of some of the clones that are obtained after the second round of panning, indicates that the clones are undergoing rearrangement and deletion.

b. Preparative FACS Method with Ret/IgG—80,000 cDNA clones from the day 18 embryonic rat kidney library (CDM8 vector) are introduced into COS7 cells and subjected to preparative FACS using the rat Ret/IgG protein followed by a fluor-tagged secondary antibody. The top 0.5% and 0.9% of fluorescing cells are collected and the plasmid DNA is recovered by Hirt lysis. The DNA is electroporated back into E. coli: 228 clones are obtained for the 0.5% pool and 752 clones for the 0.9% pool. DNA is recovered from the bacterial clones and a second round of preparative FACS is performed. Plasmids recovered from bacterial clones at the end of the second round are analyzed and found to contain large deletions and rearrangements.

c. Colorimetric Detection Method with Ret/AP—COS cells are transfected with 400 pools of the cDNA clones (1000 clones per pool) from the day 18 rat embryonic kidney cDNA library (CDM8 vector) and stained with the Ret/AP protein and a colorimetric substrate for alkaline phosphatase. The transfected cells are inspected under a microscope for positive signals. In one experiment, five potential positives were re-analyzed, but all were negative.

As a control for the Ret/AP protein, a VCAM/AP protein is produced by fusing the first two domains of human VCAM to the N-terminus of placental AP. (VCAM binds to the integrin VLA4, which is composed of two chains, alpha-4 and beta-1). Transient transfections of COS cells produces sufficient VCAM/AP protein for control experiments. The VCAM/AP protein is compared to VCAM/IgG directly coupled to AP, and to VCAM/IgG plus an AP coupled secondary antibody, in order to assess their ability to detect VLA4 on COS cells transfected with the alpha-4 chain cDNA (COS cells already express the beta-1 chain). The results show that while the VCAM/AP protein could detect VLA4 on transfected cells, the best detection is afforded by the VCAM/IgG protein in combination with an AP coupled secondary antibody.

d. Methodological Conclusions:
Three major conclusions emerged from these initial cloning efforts:

1) Methods which require that plasmid DNA be recovered for subsequent rounds (i.e. panning and preparative FACS) are not suitable when the abundance of the target cDNA is low, because of rearrangements and deletions that occur during these subsequent rounds. Based on the low expression of Ret, there is good reason to suspect that the expression of RetL1 is also low. The preferred approach is to transfect in pools and use a detection method that allows a positive pool to be identified. The original pool can then be broken down, with no need to recover the transiently expressed DNA from transfected cells.

2) The Ret/IgG protein when coupled to a secondary reagent affords better detection capability than the Ret/AP protein.

3) Control experiments with a VCAM/IgG control protein (and an AP coupled secondary antibody) and the alpha-4 integrin cDNA (diluted into CDM8 vector and transfected into COS cells) indicate that our detection capability is just about one in a thousand (i.e. the pool size cannot exceed 1000 clones). To attain an improved level of sensitivity, we changed from an SV40 origin based vector (expressed in COS cells) to an EBV origin based vector (expressed in EBNA positive cell lines). EBV origin based vectors are maintained as episomes and are not as toxic to the cell as the SV40 origin based vectors after amplification. Considerable evidence exists that genes can be expressed at higher levels in these vectors and that cDNAs can be diluted much further (i.e. up to 1 to 80,000) and still be detected.

2. Screening of Pools From the EBV Origin Based cDNA Library

We screen pools of clones from the day 18 rat embryonic kidney cDNA library (CH269 vector with the EBV origin) with the rat Ret/IgG fusion protein. In one experiment, 256 pools, each containing 5000 clones from the library, are generated. Briefly, an aliquot of the cDNA library is titered, 5000 cells are plated (256 times), and are allowed to grow overnight. The colonies are scraped into medium: part of the culture is used to generate a glycerol stock for the pool (stored at −70) and part is used for a plasmid preparation. DNAs from the 256 pools are individually transfected into 293/EBNA cells ($8 \times 10^5$ on a 60 mm plate) using the lipofection method. After 48 hr, the cells are washed two times with HBHA buffer (0.5 mg/ml BSA, 0.1% NaN$_3$, 20 mM HEPES (pH 7.0)) and incubated with 20 ug/ml rat Ret/IgG in Tris-buffered saline plus 1 mM MgCl$_2$ and CaCl$_2$ for 60–90 min at RT. Following this incubation, the cells are washed four times with HBHA buffer and then fixed with 60% acetone/3% formaldehyde/20 mM HEPES (pH 7.0) for 30 sec. Following two washes with HBS buffer (150 mM NaCl, 20 mM HEPES (pH 7.0)), the cells are incubated with an AP-coupled secondary antibody (goat anti-human. IgG Fc-gamma-specific F(ab')$_2$ (Jackson Immuno Research Laboratories; catalog #109-056-098; 1:5000 dilution in Tris-buffered saline plus 1 mM MgCl$_2$ and CaCl$_2$) for 60 min at RT. The cells are then washed twice with HBS buffer and twice with AP substrate buffer (100 mM Tris-HCl (pH 9.5), 100 mM NaCl, 5 mM MgCl$_2$) containing 2×Pierce Immuno Pure$^R$ Phosphatase suppressor (catalog #35002). The last wash is left for 15 min. The AP substrates NBT (0.33 mg/ml) and BCIP (0.17 mg/ml) are then added in AP substrate buffer containing the Pierce AP inhibitor and incubated with the cells for 5–20 min. The plates are then washed twice with water. The plates are then inspected under a dissecting microscope for the presence of purple stained cells.

From an analysis of the 256 pools, 17 positive pools are identified in the primary screen. DNA from each positive pool is re-transfected into 293/EBNA cells and the above procedure repeated along with some additional control experiments to confirm that the staining observed is Ret/IgG specific. 10 out of the 17 positive pools only show staining with Ret/IgG fusion protein and not with another IgG fusion protein.

3. Breakdown of Pool #230

As an example, one of the above-described positive pools, designated #230, is broken down into smaller subpools in order to identify the cDNA within the pool that is conferring binding to the Ret/IgG fusion protein. 600 cells from the glycerol stock for pool #230 are plated (10 times) and grown overnight. Colonies on these plates are scraped into medium: one tenth of the culture is used to generate a glycerol stock and the remaining portion is used for a DNA preparation. The ten subpools of 600 clones are designated 230-1A through 230-5A and 230-1B through 230-5B. DNAs from these subpools are transfected into 293/EBNA cells and the procedure described above for staining with the Ret/IgG fusion protein is repeated. One subpool #230-5A is positive for staining with the Ret/IgG protein.

Pool #230-5A is further broken down in order to identify the cDNA with this subpool that is conferring binding to the Ret/IgG fusion protein. Cells from the glycerol stock of pool 230-5A are plated and grown overnight. Colonies are picked into the wells of seven 96-well Bioblocks® and grown overnight. From each 96-well Bioblock, 4 pools of 20 clones and 1 pool of 16 clones are made. Thus 35 pools are generated from the seven Bioblocks® designated 230-5A-71 through 230-5A-105. DNAs are prepared from each of these pools and transfected into 293/EBNA cells and re-assayed with the Ret/IgG fusion protein as described above. Pool #230-5A-86 is positive.

Pool #230-5A-86 is broken down by going back to the Bioblock and identifying the 20 clones that we mixed together to make this pool. DNAs are made from all twenty clones and transfected individually into 293/EBNA cells and re-assayed for Ret/IgG as described above. Pool #230-5A-86-17 is found to be positive.

4. Characterization of Clone #236-5A-86-17

Clone #230-5A-86-17 (called retL-17 or clone 17 and deposited as ATCC 98047) is further analyzed by DNA sequencing. The entire nucleotide sequence of the insert of this clone is SEQ ID NO:1 (rat retL1 cDNA), and part of the nucleotide sequence is shown in FIG. 1. Within this nucleotide sequence, we find a reading frame coding for a protein of 468 amino acids (rat RetL1). The predicted protein has a signal sequence with a predicted cleavage after amino acid 24 (Von Heijne et al., Nucl. Acid Res. 14:14683 (1986)). The hydrophobic C-terminus indicates that the protein may be linked to the cell via a phosphatidylinositol glycan linkage. There are three predicted N-linked glycosylation sites. These properties are consistent with those expected for a ligand for Ret.

We can express soluble forms of the rat RetL1 protein by truncating the gene prior to the, hydrophobic C terminus. For example, this could be done by truncating after Lysine 435 (rat RetL1). Truncation upstream of this amino acid should also result in the expression of a soluble form of the rat RetL1 protein. The soluble rat RetL1 protein can be expressed by itself or as a part of a fusion with human immunoglobulin, a histidine tag, or a small epitope that is recognized by an antibody.

B. Cloning of Human Ret Ligand RetL1

A human embryonic kidney cDNA library in the vector lambda gt10 is purchased from Clontech (catalog #HL5004A). One million plaque forming units from the phage stock are plated on 10 Nunc™ plates. Duplicate plaque lifts are made on Schleicher and Schuell Optitran™ filters.

A probe is generated by digesting plasmid rat RetL1 with the restriction enzyme PvuII, followed by agarose gel isolation of a 1.34 kb fragment which corresponds to nt 242–1582 of the rat RetL nucleotide sequence (rat retL1 cDNA). This coding region probe is $P^{32}$ labeled by random priming (Feinberg and Vogelstein, Anal. Biochem. 137:266–267, 1984). The filters are hybridized overnight in 300 ml plaque screen PSB buffer (50 mM Tris pH 7.5, 1M NaCl, 0.1% sodium pyrophosphate, 0.2% PVP, and 0.2% Ficoll) containing 10% dextran sulphate, 100 ug/ml tRNA, and $6.7 \times 10^7$ CPM of the rat probe, at 55 C. They are washed twice with plaque screen buffer and twice with 2xSSC/1%SDS at 55 C and exposed to film at −70 C with an intensifying screen.

Duplicate positives are cored from the master plates into SM (100 mM NaCl, 10 mM $SO_4$, 50 mM Tris pH 7.5) plus gelatin. 24 of these positives are plaque purified. Lambda miniprep DNA from the purified candidate plaques is digested with NotI, electrophoresed on 1% agarose gel and Southern blotted. The Southern blot is hybridized with the rat rat RetL1 coding region probe. Clone HRL20 has the longest insert (4.4 kb) which hybridizes intensely to the rat probe. DNA sequence (partial human retL1 cDNA; SEQ ID NO: 8; FIG. 2A) and deduced peptide sequence (partial human RetL1; SEQ ID NO: 9; FIG. 2A) have been obtained from this clone, confirming that it is the human homologue. This clone encodes most of the coding region, including the 3' end of the coding region.

To obtain the 5' end of the human cDNA, a human fetal kidney Marathon-Ready™ cDNA kit is purchased from Clontech (catalog #7423-1). Antisense oligonucleotides Kid-155, corresponding to the complement of nucleotides 62–81 of SEQ ID NO: 8 (partial human retL1 cDNA) and Kid-154, corresponding to the complement of nucleotides 17–43 of SEQ ID NO: 8 (partial human retL1 cDNA) are synthesized. PCR is performed using the Advantage™ cDNA PCR kit (Clontech catalog #8417-1) combined with Marathon™ cDNA reagents and the oligonucleotides Kid-155 or Kid-154. The first PCR reaction is set up as follows: 35.5 ul $H_2O$; 5.0 ul 10xKlenTaq Buffer; 1.0 ul 10 mM dNTP mix; 1.0 ul 50xAdvantage™ KlenTaq. Polymerase mix. These reagents are combined and mixed. Then 5.0 ul Marathon-Ready™ Fetal Kidney cDNA;. 1.0 ul 10 uM AP1 primer and 1.5 ul 6.4 uM Kid-155 are added (final volume= 50 ul). PCR is carried out in a Perkin-Elmer Cetus DNA Thermal Cycler 480 with the following cycle conditions: 1 cycle of 94 C for 1 min; 30 cycles of 94 C for 30 sec, 55 C for 30 sec, 68 C for 4 min. A nested PCR is performed using the product of the first PCR reaction. First, 5 ul of PCR product #1 is diluted 50 fold with TE (final volume 250 ul). The nested PCR reaction contains 35.5 ul $H_2O$; 5.0 ul 10xKlenTaq Buffer; 1.0 ul 10 mM dNTP mix; 1.0 ul 50xAdvantage™ KlenTaq Polymerase mix. These reagents are mixed as above. 5.0 ul diluted PCR product #1; 1.0 ul 10 uM AP2 primer and 1.5 ul 6.9 uM Kid-154 are then added. Cycle conditions are the same as above. The resultant product of approximately 700 bp is purified on a 1% low-melt agarose gel and phenol extracted. The purified DNA is cloned into the EcoR5 site of pZErO™ (Invitrogen catalog #K2510-01). Sequence information is obtained from multiple isolates, including clones called HRL7G6 and HRL7G8.

The sequence obtained from clone HRL7G8 is found to overlap with the sequence of clone HRL20 (partial human retL1 cDNA) and is used to generate a full-length sequence of human RetL1 (full-length human retL1 cDNA), also shown in FIG. 2B. The nucleotide sequence obtained from clone HRL7G8 represents nucleotides 1 to 502 of full-length human retL1 cDNA; the nucleotide sequence from clone HRL20 represents nucleotides 460 to 1682 of full-length human retL1 cDNA. The sequence from clone HRL7G8 is confirmed by sequencing another cDNA clone (GJ102) isolated from the human embryonic kidney lambda gt10 cDNA library described above, using a probe derived from clone HRL7G6. Nucleotides 118 to 1497 comprise the protein reading frame of full-length human retL1 cDNA.

The complete amino acid sequence of human RetL1 is also shown in FIG. 2B. As shown by the BESTFIT analysis depicted in FIG. 3A, the human retL1 cDNA is 88.2% identical to the rat retL1 cDNA. The peptide comparison (FIG. 3B) shows the human putative peptide sequence to be 93.3% identical, and 97.2% similar, to that of the rat.

Cloning of Ret Ligand RetL2

A. Cloning of Human RetL2

The peptide sequence of rat RetL1 (rat RetL1) is used to search the GenBank database with the program BLAST in order to identify related proteins (i.e. isologs). BLAST, or Basic Local Alignment Search Tool, uses the method of Altschul et al. (J. Mol. Biol. 215: 403–410, 1990) to search for similarities between a query sequence and all the sequences in the sequence database. The query sequence and the database to be searched can be either peptide or nucleotide in any combination. When the rat RetL1 peptide sequence is queried against the Expressed Sequence Tag (EST) nucleotide database, two significant matches are obtained. One is with GenBank Accession #R02249, a 229 bp EST from a combined human fetal liver and spleen cDNA library, and the other is with Genbank Accession #H12981, a 521 bp EST from a human infant brain cDNA library. The two ESTs share 99% identity in a region of overlap indicating that they are from the same cDNA. Oligonucleotides are generated from the H12981 EST: KID-228 (GAA TGA CAA CTG CAA GAA GCT GCG CTC CTC; corresponding to nucleotides 38–67 and also to nucleotides 534–563 of SEQ ID NO:12), and antisense oligonucleotide KID-229 (GTG TAC TCG CTG GGC ACC CG; corresponding to the complement of nucleotides 156–175 and also to the complement of nucleotides 652–671 of SEQ ID NO:12).

$1\times10^6$ plaque forming units from a Clontech Human Fetal Liver 5'-Stretch Plus lambda GT10 cDNA library (cat #HL5003a) are screened in duplicate on OPTITRAN™ filters. The filters are hybridized with $^{32}$P-labeled oligonucleotides KID-228 and KID-229 in 400 mls plaque screen buffer (50 mM Tris pH 7.5, 1M NaCl, 0.1% sodium pyrophosphate, 0.2% Polyvinylpryrolidine and 0.2% Ficoll) containing 10% Dextran sulfate and 100 ug/ml tRNA and 80 pmole each $^{32}$P-labeled oligonucleotide at 65 C overnight. They are washed twice with 2×SSC/1% SDS and twice with 1×SSC/1% SDS and exposed to film. 11 duplicate positives are purified. DNA from each of these clones is analyzed by restriction enzyme digest followed by agarose gel electrophoresis and Southern blotting. The filters are hybridized to KID-228 and KID-229 to confirm that the inserts hybridize to the probe. The insert of clone DSW240 is completely sequenced (human retL2 cDNA, SEQ ID NO:12) and is shown in FIG. 7.

Nucleotides 25–1416 comprise the protein reading frame of human retL2 cDNA, which encodes a protein of 464 amino acids (human RetL2; SEQ ID NO:13), and is shown in FIG. 7. As shown by the BESTFIT analysis depicted in FIG. 8, the human RetL2 protein is 49.1% identical and 63.7% similar to the human RetL1 protein. It shares in common with human RetL1 a hydrophobic N-terminus indicative of a signal sequence and a hydrophobic C-terminus indicative of a phosphatidylinositol glycan linkage motif. In addition, 30 cysteines out of the 31 that are present in each protein are conserved.

B. Demonstration That RetL2 is a Ligand for Ret

We demonstrate that RetL2 is a ligand for Ret by transfecting 293/EBNA cells with an expression plasmid that contains the insert of clone DSW240 and by showing that the cells can bind a soluble Ret/IgG fusion protein.

The insert of DSW240 is removed using NotI and cloned into the expression vector CH269 which contains an EBV origin and allows for high expression in EBNA positive cell lines. Restriction digests are performed to identify clones that have the correct orientation. Plasmid DNA is prepared from a clone having the correct orientation.

Plasmid DNAs (the retL2 expression plasmid, a retL expression plasmid for a positive control, and an expression plasmid containing an unrelated protein for a negative control) are transfected into 293/EBNA cells ($8\times10^5$ on a 60 mm plate) using the lipofection method. After 48 hr, the cells are washed two times with HBHA buffer (0.5 mg/ml BSA, 0.1% NaN$_3$, 20 mM HEPES (pH 7.0)) and incubated with 20 ug/ml rat Ret/IgG in Tris-buffered saline plus 1 mM MgCl$_2$ and CaCl$_2$ for 60–90 min at room temperature. Following this incubation, the cells are washed four times with HBHA buffer and then fixed with 60% acetone/3% formaldehyde/ 20 mM HEPES (pH 7.0) for 30 sec. Following two washes with HBS buffer (150 mM NaCl, 20 mM HEPES (pH 7.0)), the cells are incubated with an AP-coupled secondary antibody (goat anti-human IgG Fc-gamma-specific F(ab')$_2$ (Jackson Immuno Research Laboratories; catalog #109-056-098; 1:5000 dilution in Tris-buffered saline plus 1 mM MgCl$_2$ and CaCl$_2$) for 60 min at RT. The cells are then washed twice with HBS buffer and twice with AP substrate buffer (100 mM Tris-HCl (pH 9.5), 100 mM NaCl, 5 mM MgCl$_2$) containing 2×Pierce Immuno Pure® Phosphatase suppressor (catalog #35002). The last wash is left for 15 min. The AP substrates NBT (0.33 mg/ml) and BCIP (0.17 mg/ml) are then added in AP substrate buffer containing the Pierce AP inhibitor and incubated with the cells for 5–20 min. The plates are then washed twice with water. The plates are then inspected under a dissecting microscope for the presence of purple stained cells. The presence of purple stained cells indicates that the Ret/fusion protein has bound to the cells and that the RetL2 protein is a ligand for Ret. Purple stained cells are also observed after trasfection with the retL1 expression vector but not with the negative control vector.

Cloning of Ret Ligand RetL3

A. Murine RetL3

A search of the EST data base with rat RetL1 amino acid sequence discloses two murine ESTs with homology to Ret ligands. These ESTs are AA049894, and AA050083 (which is partial murine retL3 cDNA, SEQ ID NO:14). Plasmids encoding these ESTs are obtained from Genome Systems Inc. (Catalog #475791 and #475497) as bacterial stabs. Plasmid DNA is prepared from single colonies obtained by streaking the stabs onto LB Amp plates. The inserts from these plasmids are sequenced in their entirety. Comparison of the two sequences demonstrates that AA049894, which has a 1.4 kb insert, is contained within AA050083, which has a 1.9 kb insert. Translation of the DNA sequence from AA050083 indicates there is a continuous open reading frame from N205 to NT1242 (partial murine RetL3; SEQ ID NO:15). This ORF had 37.5% identity to that of rat retL1 and 40.2% identity to rat retL2. However, the open reading frame does not encode a Met or a signal sequence at the 5' end. We examine the 5' ORFs upstream of this region and find a Met in the context of a Kozak consensus sequence for translation iniation and a potential signal sequence for surface expression/secretion. This ORF is out of frame with the downstream ORF indicating that EST AA050083 contains a potential mutation, such as an insertion, deletion, intron or cloning artifact, at its 5' end.

In order to obtain the correct 5' end, we employ Marathon RACE. Mouse 11-day embryo Marathon-Ready™ cDNA (cat. #7458-1) and an Advantage Kit (cat. #8417-1) is purchased from Clontech. Antisense oligonucleotides, Kid- 366, corresponding to the complement of nucleotides 847–866 of SEQ ID NO:14 and Kid-365, corresponding to the complement of nucleotides 589–615 of SEQ ID NO:14 are synthesized. PCR is performed using and an Advantage™ cDNA PCR kit (Clontech cat. #8417-1) combined with Marathon™ cDNA reagents and oligonucleotide Kid-366. The first PCR reaction is set up as follows: 35.3 ul H$_2$O; 5.0 ul 10×KlenTaq Buffer; 1.0 ul 10 mM dNTP mix; 1.0 ul 50×Advantage™ KlenTaq Polymerase mix. These reagents are combined and mixed. Then 5.0 ul Marathon-Ready™ mouse 11-day embryo cDNA; 1.0 ul 10 uM AP1 primer and 1.7 ul 5.88 uM Kid-366 are added (final volume=50 ul). PCR is carried out in a Perkin-Elmer Cetus DNA Thermal Cycler 480 with the following cycle conditions: 1 cycle of 94 C for 1 min; 5 cycles of 94 C for 30 sec, 72 C for 4 min 5 cycles of 94 C for 30 sec, 70 C for 4 min; 25 cycles 94 C for 30 sec, 68 C for 4 min. PCR is performed using the product of the first PCR reaction. First, 5 ul of PCR product#1 is diluted 50 fold with TE(Final volume 250 ul). The nested PCR reaction contains 35.5 ul H$_2$O; 5.0 ul 10×KlenTaq Buffer; 1.0 ul 10 mM dNTP mix; 1.0 ul 50×Advantage™ KlenTaq Polymerase mix. These reagents are mixed as above. 5.0 ul diluted PCR product #1; 1.0 ul 10 uM AP2 primer and 3.6 ul 2.8 uM Kid-365 are then added. Cycle conditions are the same as above. The resultant product of approximately 665 bp is purified on a 1% low-melt agarose gel and Qiaex II (Qiagen cat #20021) extracted. The purified DNA is cloned into pNoTA/T7™ using PRIME PCR CLONER™ cloning system (5 Prime—>3 Prime cat. #1-725029). Sequence information is obtained from multiple isolates, including clones called DSW252 and DSW253.

The sequence of DSW252 is found to overlap with SEQ ID NO:14 except that an additional T is present between NT 252 and NT 253 of the SEQ ID NO:14 sequence. This T is also present in the other isolates DSW251 and DSW253. Insertion of this additional base corrects the ORF such that a single 1191 bp ORF (counting from the first Met) encoding 397 amino acids is obtained. This ORF encodes a Met in the context of a canonical translation initiation consensus sequence (Kozak) and includes a signal sequence for surface expression/secretion.

To obtain a full-length murine clone which is capable of being expressed, a 630 bp NotI-BamHI fragment of DSW252 and a 1308 bp BamHI-NotI fragment of AA050083 is purified and ligated to NotI digested expression vector CH269. The ligation is transformed into E. coli XL1-Blue (Strategene cat. #200236). Qiawell Ultra minipreps are performed on resultant transformants. These are analysed by restriction digest and gel electrophoresis for correct size and for orientation. This construct is called DSW254. The insert of DSW254 is sequenced in its entirety (murine retL3; SEQ ID NO:16) and the ORF is confirmed as encoding a protein of 397 amino acids (murine RetL3; SEQ ID NO:17). These sequences are also shown in FIG. 9. The C-terminus of RetL3 is hydrophobic and indicative of a phosphatidylinositol glycan linkage motif.

B. Human RetL3

In order to find a candidate tissue source for cloning human RetL3, we utilize northern blots of mouse tissues to determine the expression pattern of murine RetL3. Of the tissues surveyed, expression of RetL3 is highest in heart tissue. A human adult heart cDNA library in the vector lambda gt10 is purchased from Clontech (catalog #HL3026a). One million plaque forming units from the phage stock are plated on 10 Nunc plates. Duplicate plaque lifts are made on Schleicher and Schuell Optitran™ filters. A probe is generated by PCR with primers Kid-366 and Kid-367, corresponding to nucleotides 397–420 of the AA050083 sequence. PCR reaction is set up as follows: 10 ul 10×PFU Buffer, 2.0 ul 10 mM dNTP mix, 72.1 ul H$_2$O, 3.1 ul 13.2 uM Kid-367, 6.8 ul 5.88 uM Kid-366, 5.0 ul 0.1 ug/ul AA050083 DNA and 2.0 ul 2.5 Units/ul PFU (Stategene catalog #600154) are mixed. PCR is carried out in Perkin-Elmer Cetus DNA Thermal Cycler 480 with the following conditions: 25 cycles of 94 C for 1 min, 53 C for 1 min., 72 C for 4 min. The product is purified by extraction with phenol, chloroform, isoamyl alcohol 50:49:1 followed by low-melt agarose gel electrophoresis and QiaexII purification of the excised fragment. This coding region probe is P$^{32}$ labeled by random priming (Feinberg and Vogelstein). The filters are hybridized overnight in 200 ml Plaque screen buffer 0 containing 10% dextran sulphate, 100 ug/ml tRNA and 1.8×10$^8$ CPM of the mouse probe at 65 C. They are washed twice with plaque screen buffer, twice with 2×SSC/1% SDS, twice with 1×SSC/1% SDS at 65 C and exposed to film at −70 C with an intensifying screen. Duplicate positives are plaque purified. Lambda miniprep DNA from the purified candidate plaques is digested with EcoRI, electrophoresed on a 1% agarose gel and Southern blotted. The Southern blot is hybridized with the mouse probe. Clone GJ128, which has a 1.3 kb insert, hybridizes intensely to the mouse coding region probe. DNA sequence (partial human retL3 cDNA; SEQ ID NO:18) and deduced peptide sequence (partial human RetL3; SEQ ID NO:19) are obtained from this clone, confirming that it is the human homologue. This clone encodes most of the coding region, including the 3' end of the coding region.

The 1.3 kb insert from GJ128 is purified, labeled with P$^{32}$ and used to screen the Clontech human adult heart library in order to obtain a clone with the 5' end. No clones containing the 5' end are obtained in a screen of 2×10$^6$ plaques from this library. Northern analysis of human adult tissue mRNA blots (Clontech catalog #7760-1, 7759-1 and 7767-1) hybridized with the same probe, using protocols supplied by manufacturer, indicates that human RetL3 is expressed in human adult spinal cord, stomach, heart, pancreas, small intestine, colon, prostate and testis. A Clontech human adult spinal cord cDNA library (catalog #5001a) is screened with GJ128 insert. 3 independant clones are purified and the longest, GJ135 is sequenced. The sequence of the insert of GJ135 overlaps with the insert of GJ128, allowing the generation of a composite sequence of the full-length human retL3 cDNA (SEQ ID NO:20) and the determination of the full-length human RetL3 (SEQ ID NO:21). These sequences are also shown in FIG. 10. Human RetL3 is 34.3% and 34.9% identical to human RetL1 and human RetL2, respectively. It has 76.8% identity with murine RetL3.

THERAPEUTIC USES OF THE COMPOUNDS OF THE INVENTION

Native and variant RetL's, anti-RetL antibodies, anti-Ret antibodies, and fusion proteins of Ret and of RetL's may have therapeutic utility in situations where it is desirable to block or to activate the Ret signaling pathway, to stimulate renal and/or neuronal cell growth or survival in disease situations where these cells are lost or damaged, or to suppress growth of or to kill undesirable cells such as tumor cells that express Ret or a RetL.

In general, compounds of the invention that bind to Ret, inducing dimerization and/or autophosphorylation of Ret, are useful for stimulating growth of or limiting damage to Ret-expressing tissues. The compounds of the invention are useful for stimulating renal tissue growth and/or survival, supporting renal function, and in minimizing damage to renal tissue after various insults. Particular conditions which may be beneficially treated with the compounds of the invention include acute renal failure, acute nephritis, chronic renal failure, nephrotic syndrome, renal tubule defects, kidney transplants, toxic injury, hypoxic injury, and trauma. Renal tubule defects include those of either hereditary or acquired nature, such as polycystic renal disease, medullary cystic disease, and medullary sponge kidney. This list is not limited, and may include many other renal disorders (see, e.g., Harrison's Principles of Internal Medicine, 13th ed., 1994, which is herein incorporated by reference.)

In other applications, the genes and proteins of the invention may be used to treat conditions where neural growth and regeneration is desirable. This would include any conditions involving disorders of neural degeneration, such as Alzheimer's disease, Parkinson's, Huntington's, Tourette's, amyotrophic lateral sclerosis, as well as motor neuron disease, demyelinating diseases such as multiple sclerosis, bacterial diseases such as meningitis, abscess, or empyema, viral diseases such as HIV-associated myelopathy, prion diseases including Creutzfeldt-Jakob disease. Also included are disorders of damage to neural tissue, whether caused by neoplastic impingement, trauma, or cerebrovascular events such as hemorrhage or emboli. Diseases of the cranial nerves and of the spinal cord, including disorders involving traumatic, inflammatory, congenital or vascular etiologies, are specifically included, as are disorders affecting the autonomic nervous system. Also included are developmental neural disorders such as mental retardation, autism, fetal alcohol syndrome, Down's syndrome, and cerebral palsy. The compounds of the invention may also be used to treat syndromes involving the peripheral nervous system. These disorders include those caused by any of the factors previously listed, and specifically include Lyme disease, HIV-associated neuropathies, polymyositis, muscular dystrophy, and myasthenia gravis.

Anti-RetL antibodies and Ret fusion proteins of the invention, which specifically bind to the protein of rat RetL, partial human RetL1, full-length human RetL1, human RetL2, murine RetL3 or human RetL3, or fragments of these proteins, are useful in several methods. The compounds may be used therapeutically to inhibit or block Ret receptor signaling, such as for blocking growth of tumors which depend on activation of Ret signaling for growth. These agents may also be fused to detectable markers, such as fluoroscopically or radiographically opaque substances, and administered to a subject to allow imaging of tissues which express a RetL. The agents may also be bound to substances, such as horseradish peroxidase, which can be used as immunocytochemical stains to allow visualization of areas of RetL-positive cells on histological sections. A specific antibody could be used alone in this manner, and sites where it is bound can be visualized in a sandwich assay using an anti-immunoglobulin antibody which is itself bound to a detectable marker. Specific antibodies to any RetL are also useful in immunoassays to quantify the substance for which a given antibody has specificity. Specific antibodies to a RetL may also be bound to solid supports, such as beads or dishes, and used to remove the ligand from a solution, either for use in purifying the protein or in clearing it from the solution. Each of these techniques is routine to those of skill in the immunological arts.

Other methods of the invention include modulating Ret-RetL signaling by contacting Ret with an anti-Ret monoclonal antibody. The effect of such a mAb-Ret contact can be to either block or to stimulate activation of the Ret signaling pathway, depending on the characteristics of the interaction of each particular mAb with Ret. Certain mAbs interact with Ret as agonists, with the agonist mAb-Ret binding triggering the dimerization and autophosphorylation of Ret. Other mAbs act as Ret antagonists. The interaction of Ret with an antagonist mAb prevents Ret signaling activation by other RetL's, or by complexes comprising RetL's, which would otherwise activate the Ret signaling pathway.

A RetL and/or antibodies to Ret or to a Ret fusion protein can be used to allow imaging of tissues which express Ret, or in the immunohistological or preparative methods described above for antibodies to a RetL.

Fusion proteins encompassing a RetL and/or anti-Ret antibodies can be used to specifically target medical therapies against cancers and tumors which express Ret. Such tumors might include the several different tumor phenotypes which have been associated with mutations in Ret (N. Engl. J. Med. 335 :943–951, 1996; Nature 367: 319–320, 1996; Trends Gen. 12:138–144, 1996). Therapeutic interventions against neoplasias which express a RetL utilize fusion proteins which incorporate Ret and/or an anti-RetL antibody. The anti-Ret antibody or anti-RetL antibody may be effective by itself through antibody-dependent and complement-dependent cytolysis mediated by the Fc domain. Such hybrid ligands and antibodies can be made more effective as cancer therapeutics by using them as delivery vehicles for antineoplastic drugs, toxins and cytocidal radionuclides, such as yttrium 90. Cytotoxic effector cells may be targeted to tumor cells using heteroconjugate antibodies, where an antibody specific for either Ret or for a RetL expressed by a tumor is covalently coupled to an antibody directed against a surface protein on cytotoxic effector cells, such as NK cells or CTLs.

One example of an anti-Ret antibody or RetL therapy is to conjugate the toxic A chain of ricin or a modified full-length form of ricin (which can no longer bind cells) to a RetL or to an antibody directed against the Ret polypeptide expressed on the surface of malignant cells. In another embodiment, a toxin is conjugated to Ret or to an anti-RetL antibody to selectively target and kill RetL-positive cells, such as a tumor expressing a RetL. Such an approach has proved successful with blocked ricin conjugated to a monoclonal antibody against the CD19 antigen expressed on most neoplastic cells (Grossbard et al., Blood 79:576, 1992). Other toxins are equally useful, as known to those of skill in the art. Such toxins include, but are not limited to, pseudomonas exotoxin, diphtheria toxin, and saporin. This approach should prove even more successful using a RetL or anti-Ret antibody, as contrasted to the known anti-CD19 antigen approach, because Ret is expressed in a very limited number of tissues.

The above approaches, using fusions of ricin or other toxins, are equally applicable to toxic conjugates of RetL or of an anti-Ret antibody; these are useful for selectively targeting and killing Ret-positive cells, such as tumor cells expressing Ret.

Another approach to such medical therapies is to use radioisotope labeled RetL or anti-Ret antibodies. Such radiolabeled compounds will preferentially target radioactivity to tumor sites in cells expressing Ret, sparing normal tissues. Depending on the radioisotope employed, the radiation emitted from a radiolabeled antibody bound to a tumor cell may also kill nearby malignant tumor cells that do not express Ret. A variety of radionuclides may be used. Isotopes that emit β particles (for example, $^{131}I$) have been successful when employed with monoclonal antibodies against CD20 present on B-cell lymphomas (Kaminski et al., N. Engl. J. Med. 329: 459 (1993); Press et al., N. Engl. J. Med. 329: 1219 (1993). Radionuclides emitting β particles generate radioactive emissions that are tumoricidal over distances spanning several cell diameters, permitting the eradication of antigen negative cells and diminishing the consequences of nonhomogenous deposition of antibody or ligand in tumors.

Radionuclides emitting a particles may also be employed. The low dose rate irradiation generated by radionuclide labeled RetL or anti-Ret antibodies may be more therapeutically effective than the instantaneous irradiation delivered externally in conventional radiation therapy. Low dose rate irradiation can induce apoptosis (programmed cell death) in certain cell lines (Macklis et al., Radiat. Res. 130: 220 (1992); Maklis et al., Radiopharm. 5: 339 (1992).

The compounds of the invention are administered in therapeutically-effective amounts, which means an amount of a compound which produces a medically desirable result or exerts an influence on the particular condition being treated.

The term "subject" used herein is taken to mean any mammal to which Ret ligand or gene may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

Use of Compounds of the Invention in Gene Therapy

The RetL genes of the invention are introduced into damaged tissue to stimulate production of a RetL by the transfected cells, to promote cell growth and/or survival of cells that express Ret.

In a specific embodiment of a gene therapy method a RetL gene may be introduced into a renal or neural target tissue of choice. A RetL would then be stably expressed and stimulate Ret receptor-positive cells to grow, divide, differentiate, and/or potentiate cell survival. Furthermore, RetL genes may be introduced into a target cell using a variety of well-known methods that use either viral or non-viral based strategies.

Non-viral methods include electroporation, membrane fusion with liposomes, high velocity bombardment with DNA-coated microprojectiles, incubation with calcium-phosphate-DNA precipitate, DEAE-dextran mediated transfection, and direct micro-injection into single cells. For instance, a RetL gene may be introduced into a cell by calcium phosphate coprecipitation (Pillicer et al., Science, 209: 1414–1422 (1980); mechanical microinjection and/or particle acceleration (Anderson et al., Proc. Natl. Acad. Sci. USA, 77: 5399–5403 (1980); liposome based DNA transfer (e.g., LIPOFECTIN-mediated transfection-Fefgner et al., Proc. Nat. Acad. Sci., USA, 84: 471–477,1987; Gao and Huang, Biochim. Biophys. Res. Comm., 179: 280–285, 1991; DEAE Dextran-mediated transfection; electroporation (U.S. Pat. No. 4,956,288); or polylysine-based methods in which DNA is conjugated to deliver DNA preferentially to liver hepatocytes (Wolff et al., Science, 247: 465–468, 1990; Curiel et al., Human Gene Therapy 3: 147–154, 1992).

Target cells may be transfected with the genes of the invention by direct gene transfer. See, e.g., Wolff et al., "Direct Gene Transfer Into Moose Muscle In Vivo", Science 247:1465–68, 1990. In many cases, vector-mediated transfection will be desirable. Any of the methods known in the art for the insertion of polynucleotide sequences into a vector may be used. See, for example, Sambrook et al., Molecular Cloning: A Laboratory Manual, Cold Spring Harbor Laboratory, Cold Spring Harbor, N.Y. (1989) and Ausubel et al., Current Protocols in Molecular Biology, J. Wiley & Sons, N.Y. (1992), both of which are incorporated herein by reference. Promoter activation may be tissue specific or inducible by a metabolic product or administered substance. Such promoters/enhancers include, but are not limited to, the native RetL promoter, the cytomegalovirus immediate-early promoter/enhancer (Karasuyama et al., J. Exp. Med., 169: 13 (1989)); the human beta-actin promoter (Gunning et al., Proc. Nat. Acad. Sci. USA, 84: 4831 (1987); the glucocorticoid-inducible promoter present in the mouse mammary tumor virus long terminal repeat (MMTV LTR) (Klessig et al., Mol. Cell. Biol., 4: 1354 (1984)); the long terminal repeat sequences of Moloney murine leukemia virus (MuLV LTR) (Weiss et al., RNA Tumor Viruses, Cold Spring Harbor Laboratory, Cold Spring Harbor, N.Y. (1985)); the SV40 early region promoter (Bernoist and Chambon, Nature, 290:304 (1981)); the promoter of the Rous sarcoma virus (RSV) (Yamamoto et al., Cell, 22:787 (1980)); the herpes simplex virus (HSV) thymidine kinase promoter (Wagner et al., Proc. Nat. Acad. Sci. USA, 78:1441 (1981)); the adenovirus promoter (Yamada et al., Proc. Nat. Acad. Sci. USA, 82: 3567 (1985)).

The RetL genes may also be introduced by specific viral vectors for use in gene transfer systems which are now well established. See for example: Madzak et al., J. Gen. Virol., 73: 1533–36, 1992 (papovavirus SV40); Berkner et al., Curr. Top. Microbiol. Immunol., 158: 39–61, 1992 (adenovirus); Hofmann et al., Proc. Natl. Acad. Sci. 92: 10099–10103, 1995 (baculovirus); Moss et al., Curr. Top. Microbiol. Immunol., 158: 25–38,1992 (vaccinia virus); Muzyczka, Curr. Top. Microbiol. Immunol., 158: 97–123,1992 (adeno-associated virus); Margulskee, Curr. Top. Microbiol. Immunol., 158: 67–93, 1992 (herpes simplex virus (HSV) and Epstein-Barr virus (HBV)); Miller, Curr. Top, Microbiol. Immunol., 158: 1–24,1992 (retrovirus); Brandyopadhyay et al., Mol. Cell. Biol., 4: 749–754, 1984 (retrovirus); Miller et al., Nature, 357: 455–450, 1992 (retrovirus); Anderson, Science, 256: 808–813, 1992 (retrovirus), Current Protocols in Molecular Biology: Sections 9.10–9.14 (Ausubel et al., Eds.), Greene Publishing Associates, 1989, all of which are incorporated herein by reference.

Preferred vectors are DNA viruses that include adenoviruses (preferably Ad-2 or Ad-5 based vectors), baculovirus, herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., Gene Therapy 1: 367–384, 1994; U.S. Pat. No. 4,797,368 and 5,399,346 and discussion below.

The choice of a particular vector system for transferring, for instance, a RetL sequence will depend on a variety of factors. One important factor is the nature of the target cell population. Although retroviral vectors have been extensively studied and used in a number of gene therapy applications, they are generally unsuited for infecting cells that are not dividing but may be useful in cancer therapy since they only integrate and express their genes in replicating cells. They are useful for ex vivo approaches and are attractive in this regard due to their stable integration into the target cell genome.

Adenoviruses are eukaryotic DNA viruses that can be modified to efficiently deliver a therapeutic or reporter transgene to a variety of cell types. The general adenoviruses types 2 and (Ad2 and Ad5, respectively), which cause respiratory disease in humans, are currently being developed for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing extremely high levels of transgene delivery to virtually all cell types, regardless of the mitotic state. High titers ($10^{10}$ plaque forming units/ml) of recombinant virus can be easily generated in 293 cells (an adenovirus-transformed, complementation human embryonic kidney cell line: ATCC CRL1573) and cryo-stored for extended periods without appreciable losses. The efficacy of this system in delivering a therapeutic transgene in vivo that complements a genetic imbalance has been demonstrated in animal models of various disorders. See Y. Watanabe, *Atherosclerosis*, 36: 261–268 (1986); K. Tanzawa et al, *FEBS Letters*, 118(1): 81–84 (1980); J. L. Golasten et al, *New Engl. J. Med.*, 309 (11983): 288–296 (1983); S. Ishibashi et al, *J. Clin. Invest.*, 92:883–893 (1993); and S. Ishibashi et al, *J. Clin. Invest.*, 93: 1889–1893 (1994), all of which are incorporated herein by reference. Indeed, recombinant replication defective adenovirus encoding a cDNA for the cystic fibrosis transmembrane regulator (CFTR) has been approved for use in at least two human CF clinical trials. See, e.g., J. Wilson, *Nature*, 365: 691–692 (Oct. 21, 1993). Further support of the safety of recombinant adenoviruses for gene therapy is the extensive experience of live adenovirus vaccines in human populations.

Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis. See, e.g., Horwitz, Virology, 2d edit., ed. B. N. Fields, Raven Press Ltd., New York (1990).

The first-generation recombinant, replication-deficient adenoviruses which have been developed for gene therapy of DMD and other inherited disorders contain deletions of the entire E1a and part of the E1b regions. This replication-defective virus is grown in 293 cells containing a functional adenovirus E1a gene which provides a transacting E1a protein. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection. Adenoviruses have the advantage that they have a broad host range, can infect quiescent or terminally differentiated cells such as neurons, and appear essentially non-oncogenic. Adenoviruses do not appear to integrate in to the host genome. Because they exist extrachromasomally, the risk of insertional mutagenesis is greatly reduced. Ali et al., supra, at 373. Recombinant adenoviruses (rAdV) produce very high titers, the viral particles are moderately stable, expression levels are high, and a wide range of cells can be infected. Their natural host cells are airway epithelium, so they are useful for therapy of lung cancers.

Baculovirus-mediated transfer has several advantages. Baculoviral gene transfer can occur in replicating and non-replicating cells, and can occur in renal cells, as well as in hepatocytes, neural cells, spleen, skin, and muscle. Baculovirus is non-replicating and nonpathogenic in mammalian cells. Humans lack preexisting antibodies to recombinant baculovirus which could block infection. In addition, baculovirus is capable of incorporating and transducing very large DNA inserts.

Adeno-associated viruses (AAV) have also been employed as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See B. J. Carter, in Handbook of Parvoviruses, ed., P. Tijsser, CRC Press, pp. 155–168 (1990). It has been shown that the ITRs represent the minimal sequence required for replication, rescue, packaging, and integration of the AAV genome.

The AAV life cycle is biphasic, composed of both latent and lytic episodes. During a latent infection, AAV virions enter a cell as an encapsilated ssDNA, and shortly thereafter are delivered to the nucleus where the AAV DNA stably integrates in to a host chromosome without the apparent need for host cell division. In the absence of a helper virus, the integrated AAV genome remains latent but capable of being activated and rescued. The lytic phase of the life cycle begins when a cell harboring an AAV provirus is challenged with a secondary infection by a herpesvirus or adenovirus which encodes helper functions that are recruited by AAV to aid in its excision from host chromatin (B. J. Carter, supra). The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or –ssDNA genomes following cell lysis.

Adeno-associated viruses (AAV) have significant potential in gene therapy. The viral particles are very stable and recombinant AAVs (rAAV) have "drug-like" characteristics in that. rAAV can be purified by pelleting or by CsCl gradient banding. They are heat stable and can be lyophilized to a powder and rehydrated to full activity. Their DNA stably integrates into host chromosomes so expression is long-term. Their host range is broad and AAV causes no known disease so that the recombinant vectors are non-toxic.

Once introduced into a target cell, sequences of interest can be identified by conventional methods such as nucleic acid hybridization using probes comprising sequences that are homologous/complementary to the inserted gene sequences of the vector. In another approach, the sequence (s) may be identified by the presence or absence of a "marker" gene function (e.g, thymidine kinase activity, antibiotic resistance, and the like) caused by introduction of the expression vector into the target cell.

Formulations and Administration

The compounds of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The term "pharmaceutically acceptable carrier" means one or more organic or inorganic ingredients, natural or synthetic, with which the mutant proto-oncogene or mutant oncoprotein is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses liposomes and the HIV-1 tat protein (See Chen et al., Anal. Biochem. 227: 168–175, 1995) as well as any plasmid and viral expression vectors. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

The liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637; 4,762,915; 5,000,958 or 5,185,154. In addition, it may be desirable to express the novel polypeptides of this invention, as well as other selected polypeptides, as lipoproteins, in order to enhance their binding to liposomes. As an example, treatment of human acute renal failure with liposome-encapsulated RetL may be performed in vivo by introducing a RetL into cells in need of such treatment using liposomes. The liposomes can be delivered via catheter to the renal artery. The recombinant RetL protein is purified, for example, from CHO cells by immunoaffinity chromatography or any other convenient method, then mixed with liposomes and incorporated into them at high efficiency. The encapsulated protein may be tested in vitro for any effect on stimulating cell growth.

This invention also contemplates that the novel polypeptide of this invention may be administered to an animal via liposome delivery system in order to enhance their stability and/or immunogenicity. Delivery of the novel polypeptides via liposomes may be particularly advantageous because the liposome may be internalized by phagocytic cells in the treated animal. Such cells, upon ingesting the liposomal membrane and subsequently present the polypeptides to the immune system in conjunction with other molecules required to elicit a strong immune response.

Any of the novel RetL polypeptides of this invention may be used in the form of a pharmaceutically acceptable salt. Suitable acids and bases which are capable of forming salts with the polypeptides of the present invention are well known to those of skill in the art, and include inorganic and organic acids and bases.

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. An isolated nucleic acid encoding a polypeptide selected from the group consisting of (SEQ ID No: 17) and (SEQ ID No: 21).

2. An isolated nucleic acid encoding a polypeptide with at least 80% identity to an amino acid sequence selected from the group consisting of (SEQ ID No: 17) and (SEQ ID No: 21), wherein said polypeptide interacts with a receptor protein Ret to trigger dimerization of the receptor protein Ret or autophosphorylation of a tyrosine kinase domain of the receptor protein Ret.

3. An isolated nucleic acid having a nucleotide sequence selected from the group consisting of (SEQ ID No: 16) and (SEQ ID No: 20).

4. A vector comprising an insert comprising the nucleic acid of claim 2.

5. An isolated host cell comprising the vector of claim 4.

6. A method for producing a polypeptide comprising the steps of: culturing the host cell of claim 5; and recovering the polypeptide expressed from the insert within said host cells.

7. An isolated nucleic acid encoding a polypeptide with at least 90% sequence identity to (SEQ ID No: 21), wherein said polypeptide interacts with a receptor protein Ret to trigger dimerization of the receptor protein Ret or autophosphorylation of a tyrosine kinase domain of the receptor protein Ret.

8. The nucleic acid of claim 1, wherein the polypeptided encoded is (SEQ ID No: 21).

9. An isolated nucleic acid encoding a polypeptide with at least 80% sequence identity to, and sharing at least 80% of aligned cysteine residues with, (SEQ ID No: 21), wherein said polypeptide interacts with a receptor protein Ret to trigger dimerization of the receptor protein Ret or autophosphorylation of a tyrosine kinase domain of the receptor protein Ret.

10. The nucleic acid of claim 2, wherein the polypeptide encoded is (SEQ ID NO:21).

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 3616 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 257..1660

(xi) SEQUENCE DESCRIPTION: SEQ ID NO:1:

```
GCGGCCGCAG GTTGGGTCGG AACTGAACCC CTGAAAGCGG GTCCGCCTCC CGCCCTCGCG      60

CCCGCCCGGA TCTGAGTCGC TGGCGGCGGT GGGCGGCAGA GCGACGGGGA GTCTGCTCTC     120

ACCCTGGATG GAGCTGAACT TTGAGTGGCC AGAGGAGCGC AGTCGCCCGG GGATCGCTGC     180
```

```
ACGCTGAGCT CTCTCCCCGA GACCGGGCGG CGGCTTTGGA TTTTGGGGGG GCGGGGACCA    240

GCTGCGCGGC GGCACC ATG TTC CTA GCC ACT CTG TAC TTC GCG CTG CCA        289
               Met Phe Leu Ala Thr Leu Tyr Phe Ala Leu Pro
                1               5                  10

CTC CTG GAT TTG CTG ATG TCC GCC GAG GTG AGT GGT GGA GAC CGT CTG      337
Leu Leu Asp Leu Leu Met Ser Ala Glu Val Ser Gly Gly Asp Arg Leu
             15                  20                  25

GAC TGT GTG AAA GCC AGC GAT CAG TGC CTG AAG GAA CAG AGC TGC AGC      385
Asp Cys Val Lys Ala Ser Asp Gln Cys Leu Lys Glu Gln Ser Cys Ser
         30                  35                  40

ACC AAG TAC CGC ACA CTA AGG CAG TGC GTG GCG GGC AAG GAA ACC AAC      433
Thr Lys Tyr Arg Thr Leu Arg Gln Cys Val Ala Gly Lys Glu Thr Asn
     45                  50                  55

TTC AGC CTG ACA TCC GGC CTT GAG GCC AAG GAT GAG TGC CGT AGC GCC      481
Phe Ser Leu Thr Ser Gly Leu Glu Ala Lys Asp Glu Cys Arg Ser Ala
 60                  65                  70                  75

ATG GAG GCC TTG AAG CAG AAG TCT CTG TAC AAC TGC CGC TGC AAG CGG      529
Met Glu Ala Leu Lys Gln Lys Ser Leu Tyr Asn Cys Arg Cys Lys Arg
                 80                  85                  90

GGC ATG AAG AAA GAG AAG AAT TGT CTG CGT ATC TAC TGG AGC ATG TAC      577
Gly Met Lys Lys Glu Lys Asn Cys Leu Arg Ile Tyr Trp Ser Met Tyr
             95                 100                 105

CAG AGC CTG CAG GGA AAT GAC CTC CTG GAA GAT TCC CCG TAT GAG CCG      625
Gln Ser Leu Gln Gly Asn Asp Leu Leu Glu Asp Ser Pro Tyr Glu Pro
         110                 115                 120

GTT AAC AGC AGG TTG TCA GAT ATA TTC CGG GCA GTC CCG TTC ATA TCA      673
Val Asn Ser Arg Leu Ser Asp Ile Phe Arg Ala Val Pro Phe Ile Ser
     125                 130                 135

GAT GTT TTC CAG CAA GTG GAA CAC ATT TCC AAA GGG AAC AAC TGC CTG      721
Asp Val Phe Gln Gln Val Glu His Ile Ser Lys Gly Asn Asn Cys Leu
140                 145                 150                 155

GAC GCA GCC AAG GCC TGC AAC CTG GAC GAC ACC TGT AAG AAG TAC AGG      769
Asp Ala Ala Lys Ala Cys Asn Leu Asp Asp Thr Cys Lys Lys Tyr Arg
                160                 165                 170

TCG GCC TAC ATC ACC CCC TGC ACC ACC AGC ATG TCC AAC GAG GTC TGC      817
Ser Ala Tyr Ile Thr Pro Cys Thr Thr Ser Met Ser Asn Glu Val Cys
            175                 180                 185

AAC CGC CGT AAG TGC CAC AAG GCC CTC AGG CAG TTC TTC GAC AAG GTT      865
Asn Arg Arg Lys Cys His Lys Ala Leu Arg Gln Phe Phe Asp Lys Val
        190                 195                 200

CCG GCC AAG CAC AGC TAC GGG ATG CTC TTC TGC TCC TGC CGG GAC ATC      913
Pro Ala Lys His Ser Tyr Gly Met Leu Phe Cys Ser Cys Arg Asp Ile
    205                 210                 215

GCC TGC ACC GAG CGG CGG CGA CAG ACT ATC GTC CCC GTG TGC TCC TAT      961
Ala Cys Thr Glu Arg Arg Arg Gln Thr Ile Val Pro Val Cys Ser Tyr
220                 225                 230                 235

GAA GAA CGA GAG AGG CCC AAC TGC CTG AGT CTG CAA GAC TCC TGC AAG     1009
Glu Glu Arg Glu Arg Pro Asn Cys Leu Ser Leu Gln Asp Ser Cys Lys
                240                 245                 250

ACC AAT TAC ATC TGC AGA TCT CGC CTT GCA GAT TTT TTT ACC AAC TGC     1057
Thr Asn Tyr Ile Cys Arg Ser Arg Leu Ala Asp Phe Phe Thr Asn Cys
            255                 260                 265

CAG CCA GAG TCA AGG TCT GTC AGC AAC TGT CTT AAG GAG AAC TAC GCA     1105
Gln Pro Glu Ser Arg Ser Val Ser Asn Cys Leu Lys Glu Asn Tyr Ala
        270                 275                 280

GAC TGC CTC CTG GCC TAC TCG GGA CTG ATT GGC ACA GTC ATG ACT CCC     1153
Asp Cys Leu Leu Ala Tyr Ser Gly Leu Ile Gly Thr Val Met Thr Pro
    285                 290                 295

AAC TAC GTA GAC TCC AGC AGC CTC AGC GTG GCA CCA TGG TGT GAC TGC     1201
```

-continued

```
Asn Tyr Val Asp Ser Ser Ser Leu Ser Val Ala Pro Trp Cys Asp Cys
300                 305                 310                 315

AGC AAC AGC GGC AAT GAC CTG GAA GAC TGC TTG AAA TTT CTG AAT TTT     1249
Ser Asn Ser Gly Asn Asp Leu Glu Asp Cys Leu Lys Phe Leu Asn Phe
                320                 325                 330

TTT AAG GAC AAT ACT TGT CTC AAA AAT GCA ATT CAA GCC TTT GGC AAT     1297
Phe Lys Asp Asn Thr Cys Leu Lys Asn Ala Ile Gln Ala Phe Gly Asn
            335                 340                 345

GGC TCA GAT GTG ACC ATG TGG CAG CCA GCC CCT CCA GTC CAG ACC ACC     1345
Gly Ser Asp Val Thr Met Trp Gln Pro Ala Pro Pro Val Gln Thr Thr
        350                 355                 360

ACT GCC ACC ACT ACC ACT GCC TTC CGG GTC AAG AAC AAG CCT CTG GGG     1393
Thr Ala Thr Thr Thr Thr Ala Phe Arg Val Lys Asn Lys Pro Leu Gly
    365                 370                 375

CCA GCA GGG TCT GAG AAT GAG ATC CCC ACA CAC GTT TTA CCA CCC TGT     1441
Pro Ala Gly Ser Glu Asn Glu Ile Pro Thr His Val Leu Pro Pro Cys
380                 385                 390                 395

GCG AAT TTG CAG GCT CAG AAG CTG AAA TCC AAT GTG TCG GGT AGC ACA     1489
Ala Asn Leu Gln Ala Gln Lys Leu Lys Ser Asn Val Ser Gly Ser Thr
                400                 405                 410

CAC CTC TGT CTT TCT GAT AGT GAT TTC GGA AAG GAT GGT CTC GCT GGT     1537
His Leu Cys Leu Ser Asp Ser Asp Phe Gly Lys Asp Gly Leu Ala Gly
            415                 420                 425

GCC TCC AGC CAC ATA ACC ACA AAA TCA ATG GCT GCT CCT CCC AGC TGC     1585
Ala Ser Ser His Ile Thr Thr Lys Ser Met Ala Ala Pro Pro Ser Cys
        430                 435                 440

AGT CTG AGC TCA CTG CCG GTG CTG ATG CTC ACC GCC CTT GCT GCC CTG     1633
Ser Leu Ser Ser Leu Pro Val Leu Met Leu Thr Ala Leu Ala Ala Leu
    445                 450                 455

TTA TCT GTA TCG TTG GCA GAA ACG TCG TAGCTGCATC CGGGAAAACA           1680
Leu Ser Val Ser Leu Ala Glu Thr Ser
460                 465

GTATGAAAAG ACAAAAGAGA ACCAAGTATT CTGTCCCTGT CCTCTTGTAT ATCTGAAAAT   1740

CCAGTTTTAA AAGCTCCGTT GAGAAGCAGT TTCACCCAAC TGGAACTCTT TCCTTGTTTT   1800

TAAGAAAGCT TGTGGCCCTC AGGGGCTTCT GTTGAAGAAC TGCTACAGGG CTAATTCCAA   1860

ACCCATAAGG CTCTGGGGCG TGGTGCGGCT TAAGGGGACC ATTTGCACCA TGTAAAGCAA   1920

GCTGGGCTTA TCATGTGTTT GATGGTGAGG ATGGTAGTGG TGATGATGAT GGTAATTTTA   1980

ACAGCTTGAA CCCTGTTCTC TCTACTGGTT AGGAACAGGA GATACTATTG ATAAAGATTC   2040

TTCCATGTCT TACTCAGCAG CATTGCCTTC TGAAGACAGG CCCGCAGCCT AGTGTGAATG   2100

ACAAGTGGAG GTTGGCCTCA AGAGTGGACT TGGCAGACTC TACCTTGTAG TAATGTTCAC   2160

CTTTCCGTGT ATGGTCTCCA CAGAGTGTTT ATGTATTTAC AGACTGTTCT GTGATCCCCC   2220

AACAACAACA ACCACAAATT CCTTGGTCAC CTCCAAATGT AACCGGTCCT TTAGCCCAGT   2280

AGAGGAGGGT GGGTGTGGCC CTGGCACAGC TCCCGGATTG TTGATGGGCA CTCTCCTGAG   2340

CTTTGCTTGA GTGAGAAGCT GAATGTAGCT GAAAATCAAC TCTTCTTACA CTTCTTACTG   2400

CTTCGTTCAC TTACGAGGTC ACATATAGAA CAAACATCAC CAACTATTAG CTTACCGTTA   2460

GCTTCCCAAC TATTAGCTTT CTATGTTTTG AAAGCAGTGT TGCTGACCCC ATGTTTTAAT   2520

GATGGTTTAA TACATGCAGC CCTTTCCTCT CATCGGTAAC ACTAGCTCCA ACATCAACTT   2580

CATGCATGTG GCTCTCAAAA GCAGGCCCCA AGAAGCCCAG TTCTTAGGA GAAAGCTGCG    2640

TCCTGTTTCT GTGGACAGGC AGGAGGAAAC AGAGCAGCCT GCCCGTGGTG TCTTTATCTG   2700

TTTTGAAATC AAGGCTGCCT GTGTGTAAGG AATGGTTCAA TTCTTATAAA GGGTGCCACT   2760
```

-continued

```
GTTGATGCCA CAACTGGCAG TTGGTCTAGC TCCAGGACAC CGGTTTCCAT GTTGCCTGGC    2820

AGAGACAGCT TTGATTGGGA CTGGCTGGCC ACAAGGGATG GGATGAAGAT GTGCTGCCCT    2880

CTCTTTCAAA GTTGAGCCCT GCCAGGGCAC ATAGAAGCAT CTTTGCTCCT GACCACAACG    2940

TAGAACAGCT TGGATTCAAG GTCATCAAGC GTCTCCTGTA CATTGCTCTG TGACCTTCAT    3000

AACAGACTGT CCCGCACAAA AGGAACGGCA GTTTATGGAT CTAGAGTGGG AGCACAGGGT    3060

CTGGAAAGGT GAACCGATTG GCAAAATACA CAGAACAGGA GGGAGAGTCT CAAGCCGAGA    3120

CATCTTGCTT ACTAGCCACA CACCATCTCC TGGAGCCCTC CTCCTGACCT GGGCAGACCC    3180

TTAGGTGTAT ATCTAAAGAC CTCTTCAATG TTCAGGTTCA GAATCTGTAA ATGGTTGCGT    3240

CCTGGCACCC ATTCCTGAAA ACTGAACAAA GGAGAGGATA TCTTTCCTCC ATTGAGCCCT    3300

GAAAGTATGA CTGGCTTCTC ACCCTCCCAC AGAGCAGGGA GCCCTGGTGC ACACAGTCTC    3360

CTGATATCCT CCCTGCTCTT TGAGGTTTGC CTTGGGAGAA AATGATTCAC CTCGGGAGGG    3420

GACGCTTTGG TGTCTGAAGT ACGTTTATAT CGAAATGTTA ATGAATACCC ATGTAAAATA    3480

CTCAATAGCC ACCTTTCTTC CCTTCACAAT GTTTTCGAGG GGAATGCATC CAACATCCAA    3540

GTGTACCTGG TCAGTGGGAA GTTCCATGAA GACTCATACA TTGAATAAAC ATATTCGATG    3600

TGCCGAAAGC GGCCGC                                                    3616
```

(2) INFORMATION FOR SEQ ID NO:2:

(i) SEQUENCE CHARACTERISTICS:
        (A) LENGTH: 468 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Leu Ala Thr Leu Tyr Phe Ala Leu Pro Leu Leu Asp Leu Leu
 1               5                  10                  15

Met Ser Ala Glu Val Ser Gly Gly Asp Arg Leu Asp Cys Val Lys Ala
                20                  25                  30

Ser Asp Gln Cys Leu Lys Glu Gln Ser Cys Ser Thr Lys Tyr Arg Thr
            35                  40                  45

Leu Arg Gln Cys Val Ala Gly Lys Glu Thr Asn Phe Ser Leu Thr Ser
        50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
                100                 105                 110

Asn Asp Leu Leu Glu Asp Ser Pro Tyr Glu Pro Val Asn Ser Arg Leu
            115                 120                 125

Ser Asp Ile Phe Arg Ala Val Pro Phe Ile Ser Asp Val Phe Gln Gln
        130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175

Pro Cys Thr Thr Ser Met Ser Asn Glu Val Cys Asn Arg Arg Lys Cys
                180                 185                 190

His Lys Ala Leu Arg Gln Phe Phe Asp Lys Val Pro Ala Lys His Ser
```

-continued

```
                       195                 200                 205
Tyr Gly Met Leu Phe Cys Ser Cys Arg Asp Ile Ala Cys Thr Glu Arg
    210                 215                 220
Arg Arg Gln Thr Ile Val Pro Val Cys Ser Tyr Glu Arg Glu Arg
225                 230                 235                 240
Pro Asn Cys Leu Ser Leu Gln Asp Ser Cys Lys Thr Asn Tyr Ile Cys
                245                 250                 255
Arg Ser Arg Leu Ala Asp Phe Phe Thr Asn Cys Gln Pro Glu Ser Arg
            260                 265                 270
Ser Val Ser Asn Cys Leu Lys Glu Asn Tyr Ala Asp Cys Leu Leu Ala
        275                 280                 285
Tyr Ser Gly Leu Ile Gly Thr Val Met Thr Pro Asn Tyr Val Asp Ser
    290                 295                 300
Ser Ser Leu Ser Val Ala Pro Trp Cys Asp Cys Ser Asn Ser Gly Asn
305                 310                 315                 320
Asp Leu Glu Asp Cys Leu Lys Phe Leu Asn Phe Lys Asp Asn Thr
                325                 330                 335
Cys Leu Lys Asn Ala Ile Gln Ala Phe Gly Asn Gly Ser Asp Val Thr
                340                 345                 350
Met Trp Gln Pro Ala Pro Val Gln Thr Thr Thr Ala Thr Thr Thr
            355                 360                 365
Thr Ala Phe Arg Val Lys Asn Lys Pro Leu Gly Pro Ala Gly Ser Glu
    370                 375                 380
Asn Glu Ile Pro Thr His Val Leu Pro Pro Cys Ala Asn Leu Gln Ala
385                 390                 395                 400
Gln Lys Leu Lys Ser Asn Val Ser Gly Ser Thr His Leu Cys Leu Ser
                405                 410                 415
Asp Ser Asp Phe Gly Lys Asp Gly Leu Ala Gly Ala Ser Ser His Ile
                420                 425                 430
Thr Thr Lys Ser Met Ala Ala Pro Pro Ser Cys Ser Leu Ser Ser Leu
            435                 440                 445
Pro Val Leu Met Leu Thr Ala Leu Ala Ala Leu Leu Ser Val Ser Leu
    450                 455                 460
Ala Glu Thr Ser
465
```

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AAGGAAAAAA GCGGCCGCCA TGGCGAAGGC GACGTCCGG                      39

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AGTTTTGTCG ACCGTGCGGC ACAGCTCGTC GCA                            33

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGTTTTGTCG ACCGTGCGGC ACAGCGCATC ACA                            33

(2) INFORMATION FOR SEQ ID NO:6:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 10..1920

(xi) SEQUENCE DESCRIPTION: SEQ ID NO:6:

```
GCGGCCGCC ATG GCG AAG GCG ACG TCC GGC GCC GCA GGG CTG GGG CTG         48
           Met Ala Lys Ala Thr Ser Gly Ala Ala Gly Leu Gly Leu
               470             475                 480

AAG CTG TTT TTG CTG CTG CCG CTA CTG GGA GAA GCC CCG CTG GGT CTC       96
Lys Leu Phe Leu Leu Leu Pro Leu Leu Gly Glu Ala Pro Leu Gly Leu
            485                 490                 495

TAC TTC TCA AGG GAT GCT TAC TGG GAG AGG CTG TAT GTG GAC CAG CCA      144
Tyr Phe Ser Arg Asp Ala Tyr Trp Glu Arg Leu Tyr Val Asp Gln Pro
        500                 505                 510

GCT GGC ACA CCT CTG CTC TAT GTC CAT GCC CTA CGG GAT GCC CCT GGA      192
Ala Gly Thr Pro Leu Leu Tyr Val His Ala Leu Arg Asp Ala Pro Gly
515                 520                 525

GAA GTG CCC AGC TTC CGC CTG GGC CAG TAT CTC TAT GGC GTC TAC CGC      240
Glu Val Pro Ser Phe Arg Leu Gly Gln Tyr Leu Tyr Gly Val Tyr Arg
530                 535                 540                 545

ACG CGT CTG CAT GAG AAT GAC TGG ATC CAC ATC GAT GCG GGC ACT GGC      288
Thr Arg Leu His Glu Asn Asp Trp Ile His Ile Asp Ala Gly Thr Gly
            550                 555                 560

CTC CTC TAC CTC AAT CAG AGC CTG GAC CAT AGT TCC TGG GAG CAG CTC      336
Leu Leu Tyr Leu Asn Gln Ser Leu Asp His Ser Ser Trp Glu Gln Leu
            565                 570                 575

AGC ATC CGA AAT GGC GGC TTC CCC TTG CTC ACC GTC TTC CTC CAG GTC      384
Ser Ile Arg Asn Gly Gly Phe Pro Leu Leu Thr Val Phe Leu Gln Val
            580                 585                 590

TTC CTG GGG TCC ACA GCC CAG AGA GAG GGA GAG TGT CAT TGG CCA GGC      432
Phe Leu Gly Ser Thr Ala Gln Arg Glu Gly Glu Cys His Trp Pro Gly
            595                 600                 605

TGT GCC CGT GTG TAC TTC TCC TTC ATC AAC GAC ACC TTC CCA AAT TGT      480
Cys Ala Arg Val Tyr Phe Ser Phe Ile Asn Asp Thr Phe Pro Asn Cys
610                 615                 620                 625

AGC TCC TTC AAA GCC CGG GAT CTC TGC ACC CCA GAG ACG GGT GTG TCC      528
Ser Ser Phe Lys Ala Arg Asp Leu Cys Thr Pro Glu Thr Gly Val Ser
                630                 635                 640
```

```
TTC CGC ATC AGG GAG AAC AGG CCC CCT GGC ACC TTC TAC CAG TTC CGC      576
Phe Arg Ile Arg Glu Asn Arg Pro Pro Gly Thr Phe Tyr Gln Phe Arg
            645                 650                 655

ATG CTA CCT GTG CAG TTC CTT TGT CCT AAC ATC AGT GTG AAG TAC AAA      624
Met Leu Pro Val Gln Phe Leu Cys Pro Asn Ile Ser Val Lys Tyr Lys
        660                 665                 670

CTC TTA GAA GGG GAC GGT CTG CCC TTC CGT TGT GAC CCC GAC TGT CTG      672
Leu Leu Glu Gly Asp Gly Leu Pro Phe Arg Cys Asp Pro Asp Cys Leu
    675                 680                 685

GAG GTG AGC ACG CGG TGG GCA CTG GAT CGG GAG CTT CAG GAG AAG TAT      720
Glu Val Ser Thr Arg Trp Ala Leu Asp Arg Glu Leu Gln Glu Lys Tyr
690                 695                 700                 705

GTG CTG GAG GCT GAG TGC GCA GTG GCA GGC CCT GGA GCC AAC AAG GAG      768
Val Leu Glu Ala Glu Cys Ala Val Ala Gly Pro Gly Ala Asn Lys Glu
                710                 715                 720

AAG GTG GCC GTG TCC TTC CCG GTG ACG GTG TAT GAT GAA GAC GAC TCC      816
Lys Val Ala Val Ser Phe Pro Val Thr Val Tyr Asp Glu Asp Asp Ser
                    725                 730                 735

CCG CCC ACC TTC TCC GGA GGT GTG GGC ACC GCC AGT GCT GTG GTG GAG      864
Pro Pro Thr Phe Ser Gly Gly Val Gly Thr Ala Ser Ala Val Val Glu
                        740                 745                 750

TTT AAG CGG AAG GAG GGC ACT GTG GTA GCC ACT CTG CAG GTG TTT GAT      912
Phe Lys Arg Lys Glu Gly Thr Val Val Ala Thr Leu Gln Val Phe Asp
    755                 760                 765

GCA GAT GTG GTC CCA GCA TCT GGG GAG CTG GTG AGG CGG TAC ACA AGC      960
Ala Asp Val Val Pro Ala Ser Gly Glu Leu Val Arg Arg Tyr Thr Ser
770                 775                 780                 785

ACA CTA CTC TCA GGG GAT TCC TGG GCC CAG CAG ACC TTC CGG GTG GAG     1008
Thr Leu Leu Ser Gly Asp Ser Trp Ala Gln Gln Thr Phe Arg Val Glu
                790                 795                 800

CAC ACA CCC AAC GAG ACC TTG GTC CAG TCC AAC AAC AAC TCC GTG CGG     1056
His Thr Pro Asn Glu Thr Leu Val Gln Ser Asn Asn Asn Ser Val Arg
        805                 810                 815

GCA ACC ATG CAC AAT TAC AAG CTG GTT CTC AAC AGG AGC CTG TCC ATC     1104
Ala Thr Met His Asn Tyr Lys Leu Val Leu Asn Arg Ser Leu Ser Ile
    820                 825                 830

TCA GAG AGC CGA GTC CTG CAG CTA GTA GTC CTG GTC AAT GAC TCA GAC     1152
Ser Glu Ser Arg Val Leu Gln Leu Val Val Leu Val Asn Asp Ser Asp
835                 840                 845

TTC CAG GGG CCT GGG TCA GGT GTT CTC TTC CTC CAT TTC AAC GTG TCT     1200
Phe Gln Gly Pro Gly Ser Gly Val Leu Phe Leu His Phe Asn Val Ser
850                 855                 860                 865

GTG CTG CCT GTC ACC CTG AAC CTA CCC ATG GCC TAC TCC TTC CCA GTG     1248
Val Leu Pro Val Thr Leu Asn Leu Pro Met Ala Tyr Ser Phe Pro Val
                870                 875                 880

AAT AGG AGA GCC CGC CGT TAT GCC CAG ATT GGG AAA GTT TGC GTG GAG     1296
Asn Arg Arg Ala Arg Arg Tyr Ala Gln Ile Gly Lys Val Cys Val Glu
                    885                 890                 895

AAC TGC CAG GAG TTC AGC GGT GTC TCC ATC CAG TAC AAG CTG CAG CCC     1344
Asn Cys Gln Glu Phe Ser Gly Val Ser Ile Gln Tyr Lys Leu Gln Pro
                        900                 905                 910

TCC AGC ACC AAC TGC AGT GCC CTA GGT GTG GTC ACC TCA ACA GAA GAC     1392
Ser Ser Thr Asn Cys Ser Ala Leu Gly Val Val Thr Ser Thr Glu Asp
    915                 920                 925

ACC TCA GGG ACC CTA TAT GTA AAT GAC ACG GAG GCC CTG CGG CGA CCT     1440
Thr Ser Gly Thr Leu Tyr Val Asn Asp Thr Glu Ala Leu Arg Arg Pro
930                 935                 940                 945

GAG TGT ACC GAG CTT CAG TAC ACA GTG GTA GCC ACT GAC CGG CAG ACC     1488
Glu Cys Thr Glu Leu Gln Tyr Thr Val Val Ala Thr Asp Arg Gln Thr
```

|  |  |  |  |  |  |  |  |  |  |  |  |  |  |  |
|---|---|---|---|---|---|---|---|---|---|---|---|---|---|---|
|  |  |  | 950 |  |  |  | 955 |  |  |  | 960 |  |  |  |
| CGC | AGG | CAG | ACC | CAA | GCT | TCG | TTA | GTC | GTC | ACA | GTG | GAG | GGG | ACA | TAC | 1536 |
| Arg | Arg | Gln | Thr | Gln | Ala | Ser | Leu | Val | Val | Thr | Val | Glu | Gly | Thr | Tyr |
|  |  |  | 965 |  |  |  | 970 |  |  |  | 975 |
| ATT | GCA | GAA | GAA | GTG | GGC | TGC | CCC | AAG | TCC | TGT | GCA | GTA | AAC | AAG | AGG | 1584 |
| Ile | Ala | Glu | Glu | Val | Gly | Cys | Pro | Lys | Ser | Cys | Ala | Val | Asn | Lys | Arg |
|  |  |  | 980 |  |  |  | 985 |  |  |  | 990 |
| CGA | CCT | GAG | TGT | GAG | GAG | TGT | GGT | GGC | CTG | GGT | TCT | CCA | ACT | GGC | AGA | 1632 |
| Arg | Pro | Glu | Cys | Glu | Glu | Cys | Gly | Gly | Leu | Gly | Ser | Pro | Thr | Gly | Arg |
|  | 995 |  |  |  |  | 1000 |  |  |  |  | 1005 |
| TGT | GAG | TGG | CGT | CAG | GGA | GAT | GGT | AAA | GGG | ATC | ACC | AGG | AAC | TTC | TCC | 1680 |
| Cys | Glu | Trp | Arg | Gln | Gly | Asp | Gly | Lys | Gly | Ile | Thr | Arg | Asn | Phe | Ser |
| 1010 |  |  |  | 1015 |  |  |  | 1020 |  |  |  | 1025 |
| ACC | TGT | TCT | CCT | AGC | ACC | AGG | ACC | TGT | CCT | GAT | GGC | CAC | TGT | GAT | GCT | 1728 |
| Thr | Cys | Ser | Pro | Ser | Thr | Arg | Thr | Cys | Pro | Asp | Gly | His | Cys | Asp | Ala |
|  |  |  | 1030 |  |  |  | 1035 |  |  |  | 1040 |
| CTG | GAG | AGC | CGG | GAT | ATC | AAC | ATT | TGC | CCC | CAG | GAC | TGT | CTC | CGT | GGC | 1776 |
| Leu | Glu | Ser | Arg | Asp | Ile | Asn | Ile | Cys | Pro | Gln | Asp | Cys | Leu | Arg | Gly |
|  |  |  | 1045 |  |  |  | 1050 |  |  |  | 1055 |
| CCC | ATT | GTT | GGC | GGG | CAT | GAG | CGA | GGG | GAG | CGC | CAG | GGG | ATT | AAA | GCC | 1824 |
| Pro | Ile | Val | Gly | Gly | His | Glu | Arg | Gly | Glu | Arg | Gln | Gly | Ile | Lys | Ala |
|  |  |  | 1060 |  |  |  | 1065 |  |  |  | 1070 |
| GGC | TAT | GGC | ATC | TGC | AAC | TGT | TTC | CCT | GAT | GAG | AAG | AAG | TGC | TTC | TGC | 1872 |
| Gly | Tyr | Gly | Ile | Cys | Asn | Cys | Phe | Pro | Asp | Glu | Lys | Lys | Cys | Phe | Cys |
|  | 1075 |  |  |  |  | 1080 |  |  |  |  | 1085 |
| GAG | CCA | GAG | GAC | AGC | CAG | GGC | CCA | TTG | TGT | GAT | GCG | CTG | TGC | CGC | ACG | 1920 |
| Glu | Pro | Glu | Asp | Ser | Gln | Gly | Pro | Leu | Cys | Asp | Ala | Leu | Cys | Arg | Thr |
| 1090 |  |  |  | 1095 |  |  |  | 1100 |  |  |  | 1105 |
| GTCGAC | | | | | | | | | | | | | | | | 1926 |

(2) INFORMATION FOR SEQ ID NO:7:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO:7:

| Met | Ala | Lys | Ala | Thr | Ser | Gly | Ala | Ala | Gly | Leu | Gly | Leu | Lys | Leu | Phe |
|---|---|---|---|---|---|---|---|---|---|---|---|---|---|---|---|
| 1 |  |  |  | 5 |  |  |  |  | 10 |  |  |  |  | 15 |  |
| Leu | Leu | Leu | Pro | Leu | Leu | Gly | Glu | Ala | Pro | Leu | Gly | Leu | Tyr | Phe | Ser |
|  |  |  | 20 |  |  |  |  | 25 |  |  |  |  | 30 |  |  |
| Arg | Asp | Ala | Tyr | Trp | Glu | Arg | Leu | Tyr | Val | Asp | Gln | Pro | Ala | Gly | Thr |
|  |  |  | 35 |  |  |  |  | 40 |  |  |  |  | 45 |  |  |
| Pro | Leu | Leu | Tyr | Val | His | Ala | Leu | Arg | Asp | Ala | Pro | Gly | Glu | Val | Pro |
|  |  | 50 |  |  |  |  | 55 |  |  |  |  | 60 |  |  |  |
| Ser | Phe | Arg | Leu | Gly | Gln | Tyr | Leu | Tyr | Gly | Val | Tyr | Arg | Thr | Arg | Leu |
| 65 |  |  |  |  | 70 |  |  |  |  | 75 |  |  |  |  | 80 |
| His | Glu | Asn | Asp | Trp | Ile | His | Ile | Asp | Ala | Gly | Thr | Gly | Leu | Leu | Tyr |
|  |  |  |  | 85 |  |  |  |  | 90 |  |  |  |  | 95 |  |
| Leu | Asn | Gln | Ser | Leu | Asp | His | Ser | Ser | Trp | Glu | Gln | Leu | Ser | Ile | Arg |
|  |  |  |  | 100 |  |  |  |  | 105 |  |  |  |  | 110 |  |
| Asn | Gly | Gly | Phe | Pro | Leu | Leu | Thr | Val | Phe | Leu | Gln | Val | Phe | Leu | Gly |
|  |  |  | 115 |  |  |  |  | 120 |  |  |  |  | 125 |  |  |
| Ser | Thr | Ala | Gln | Arg | Glu | Gly | Glu | Cys | His | Trp | Pro | Gly | Cys | Ala | Arg |
|  |  | 130 |  |  |  |  | 135 |  |  |  |  | 140 |  |  |  |

```
Val Tyr Phe Ser Phe Ile Asn Asp Thr Phe Pro Asn Cys Ser Ser Phe
145                 150                 155                 160

Lys Ala Arg Asp Leu Cys Thr Pro Glu Thr Gly Val Ser Phe Arg Ile
                165                 170                 175

Arg Glu Asn Arg Pro Pro Gly Thr Phe Tyr Gln Phe Arg Met Leu Pro
            180                 185                 190

Val Gln Phe Leu Cys Pro Asn Ile Ser Val Lys Tyr Lys Leu Leu Glu
        195                 200                 205

Gly Asp Gly Leu Pro Phe Arg Cys Asp Pro Asp Cys Leu Glu Val Ser
210                 215                 220

Thr Arg Trp Ala Leu Asp Arg Glu Leu Gln Glu Lys Tyr Val Leu Glu
225                 230                 235                 240

Ala Glu Cys Ala Val Ala Gly Pro Gly Ala Asn Lys Glu Lys Val Ala
                245                 250                 255

Val Ser Phe Pro Val Thr Val Tyr Asp Glu Asp Asp Ser Pro Pro Thr
            260                 265                 270

Phe Ser Gly Gly Val Gly Thr Ala Ser Ala Val Val Glu Phe Lys Arg
        275                 280                 285

Lys Glu Gly Thr Val Val Ala Thr Leu Gln Val Phe Asp Ala Asp Val
290                 295                 300

Val Pro Ala Ser Gly Glu Leu Val Arg Tyr Thr Ser Thr Leu Leu
305                 310                 315                 320

Ser Gly Asp Ser Trp Ala Gln Gln Thr Phe Arg Val Glu His Thr Pro
                325                 330                 335

Asn Glu Thr Leu Val Gln Ser Asn Asn Ser Val Arg Ala Thr Met
            340                 345                 350

His Asn Tyr Lys Leu Val Leu Asn Arg Ser Leu Ser Ile Ser Glu Ser
        355                 360                 365

Arg Val Leu Gln Leu Val Leu Val Asn Asp Ser Asp Phe Gln Gly
370                 375                 380

Pro Gly Ser Gly Val Leu Phe Leu His Phe Asn Val Ser Val Leu Pro
385                 390                 395                 400

Val Thr Leu Asn Leu Pro Met Ala Tyr Ser Phe Pro Val Asn Arg Arg
                405                 410                 415

Ala Arg Arg Tyr Ala Gln Ile Gly Lys Val Cys Val Glu Asn Cys Gln
            420                 425                 430

Glu Phe Ser Gly Val Ser Ile Gln Tyr Lys Leu Gln Pro Ser Ser Thr
        435                 440                 445

Asn Cys Ser Ala Leu Gly Val Val Thr Ser Thr Glu Asp Thr Ser Gly
450                 455                 460

Thr Leu Tyr Val Asn Asp Thr Glu Ala Leu Arg Arg Pro Glu Cys Thr
465                 470                 475                 480

Glu Leu Gln Tyr Thr Val Val Ala Thr Asp Arg Gln Thr Arg Gln
                485                 490                 495

Thr Gln Ala Ser Leu Val Val Thr Val Glu Gly Thr Tyr Ile Ala Glu
            500                 505                 510

Glu Val Gly Cys Pro Lys Ser Cys Ala Val Asn Lys Arg Arg Pro Glu
        515                 520                 525

Cys Glu Glu Cys Gly Gly Leu Gly Ser Pro Thr Gly Arg Cys Glu Trp
        530                 535                 540

Arg Gln Gly Asp Gly Lys Gly Ile Thr Arg Asn Phe Ser Thr Cys Ser
545                 550                 555                 560

Pro Ser Thr Arg Thr Cys Pro Asp Gly His Cys Asp Ala Leu Glu Ser
```

```
                    565                570                575
Arg Asp Ile Asn Ile Cys Pro Gln Asp Cys Leu Arg Gly Pro Ile Val
                580                585                590

Gly Gly His Glu Arg Gly Glu Arg Gln Gly Ile Lys Ala Gly Tyr Gly
            595                600                605

Ile Cys Asn Cys Phe Pro Asp Glu Lys Lys Cys Phe Cys Glu Pro Glu
        610                615                620

Asp Ser Gln Gly Pro Leu Cys Asp Ala Leu Cys Arg Thr
625                630                635

(2) INFORMATION FOR SEQ ID NO:8:

(i) SEQUENCE CHARACTERISTICS:
        (A) LENGTH: 1223 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1038

(xi) SEQUENCE DESCRIPTION: SEQ ID NO:8:

CTG CTG GAG GAT TCC CCA TAT GAA CCA GTT AAC AGC AGA TTG TCA GAT      48
Leu Leu Glu Asp Ser Pro Tyr Glu Pro Val Asn Ser Arg Leu Ser Asp
            640                645                650

ATA TTC CGG GTG GTC CCA TTC ATA TCA GTG GAG CAC ATT CCC AAA GGG      96
Ile Phe Arg Val Val Pro Phe Ile Ser Val Glu His Ile Pro Lys Gly
        655                660                665

AAC AAC TGC CTG GAT GCA GCG AAG GCC TGC AAC CTC GAC GAC ATT TGC     144
Asn Asn Cys Leu Asp Ala Ala Lys Ala Cys Asn Leu Asp Asp Ile Cys
670                675                680                685

AAG AAG TAC AGG TCG GCG TAC ATC ACC CCG TGC ACC ACC AGC GTG TCC     192
Lys Lys Tyr Arg Ser Ala Tyr Ile Thr Pro Cys Thr Thr Ser Val Ser
                690                695                700

AAC GAT GTC TGC AAC CGC CGC AAG TGC CAC AAG GCC CTC CGG CAG TTC     240
Asn Asp Val Cys Asn Arg Arg Lys Cys His Lys Ala Leu Arg Gln Phe
            705                710                715

TTT GAC AAG GTC CCG GCC AAG CAC AGC TAC GGA ATG CTC TTC TGC TCC     288
Phe Asp Lys Val Pro Ala Lys His Ser Tyr Gly Met Leu Phe Cys Ser
        720                725                730

TGC CGG GAC ATC GCC TGC ACA GAG CGG AGG CGA CAG ACC ATC GTG CCT     336
Cys Arg Asp Ile Ala Cys Thr Glu Arg Arg Arg Gln Thr Ile Val Pro
    735                740                745

GTG TGC TCC TAT GAA GAG AGG GAG AAG CCC AAC TGT TTG AAT TTG CAG     384
Val Cys Ser Tyr Glu Glu Arg Glu Lys Pro Asn Cys Leu Asn Leu Gln
750                755                760                765

GAC TCC TGC AAG ACG AAT TAC ATC TGC AGA TCT CGC CTT GCG GAT TTT     432
Asp Ser Cys Lys Thr Asn Tyr Ile Cys Arg Ser Arg Leu Ala Asp Phe
                770                775                780

TTT ACC AAC TGC CAG CCA GAG TCA AGG TCT GTC AGC AGC TGT CTA AAG     480
Phe Thr Asn Cys Gln Pro Glu Ser Arg Ser Val Ser Ser Cys Leu Lys
            785                790                795

GAA AAC TAC GCT GAC TGC CTC CTC GCC TAC TCG GGG CTT ATT GGC ACA     528
Glu Asn Tyr Ala Asp Cys Leu Leu Ala Tyr Ser Gly Leu Ile Gly Thr
        800                805                810

GTC ATG ACC CCC AAC TAC ATA GAC TCC AGT AGC CTC AGT GTG GCC CCA     576
Val Met Thr Pro Asn Tyr Ile Asp Ser Ser Ser Leu Ser Val Ala Pro
    815                820                825
```

```
TGG TGT GAC TGC AGC AAC AGT GGG AAC GAC CTA GAA GAG TGC TTG AAA       624
Trp Cys Asp Cys Ser Asn Ser Gly Asn Asp Leu Glu Glu Cys Leu Lys
830                 835                 840                 845

TTT TTG AAT TTC TTC AAG GAC AAT ACA TGT CTT AAA AAT GCA ATT CAA       672
Phe Leu Asn Phe Phe Lys Asp Asn Thr Cys Leu Lys Asn Ala Ile Gln
                850                 855                 860

GCC TTT GGC AAT GGC TCC GAT GTG ACC GTG TGG CAG CCA GCC TTC CCA       720
Ala Phe Gly Asn Gly Ser Asp Val Thr Val Trp Gln Pro Ala Phe Pro
            865                 870                 875

GTA CAG ACC ACC ACT GCC ACT ACC ACC ACT GCC CTC CGG GTT AAG AAC       768
Val Gln Thr Thr Thr Ala Thr Thr Thr Thr Ala Leu Arg Val Lys Asn
        880                 885                 890

AAG CCC CTG GGG CCA GCA GGG TCT GAG AAT GAA ATT CCC ACT CAT GTT       816
Lys Pro Leu Gly Pro Ala Gly Ser Glu Asn Glu Ile Pro Thr His Val
    895                 900                 905

TTG CCA CCG TGT GCA AAT TTA CAG GCA CAG AAG CTG AAA TCC AAT GTG       864
Leu Pro Pro Cys Ala Asn Leu Gln Ala Gln Lys Leu Lys Ser Asn Val
910                 915                 920                 925

TCG GGC AAT ACA CAC CTC TGT ATT TCC AAT GGT AAT TAT GAA AAA GAA       912
Ser Gly Asn Thr His Leu Cys Ile Ser Asn Gly Asn Tyr Glu Lys Glu
                930                 935                 940

GGT CTC GGT GCT TCC AGC CAC ATA ACC ACA AAA TCA ATG GCT GCT CCT       960
Gly Leu Gly Ala Ser Ser His Ile Thr Thr Lys Ser Met Ala Ala Pro
            945                 950                 955

CCA AGC TGT GGT CTG AGC CCA CTG CTG GTC CTG GTG GTA ACC GCT CTG      1008
Pro Ser Cys Gly Leu Ser Pro Leu Leu Val Leu Val Val Thr Ala Leu
        960                 965                 970

TCC ACC CTA TTA TCT TTA ACA GAA ACA TCA TAGCTGCATT AAAAAAATAC        1058
Ser Thr Leu Leu Ser Leu Thr Glu Thr Ser
    975                 980

AATATGGACA TGTAAAAAGA CAAAAACCAA GTTATCTGTT TCCTGTTCTC TTGTATAGCT    1118

GAAATTCCAG TTTAGGAGCT CAGTTGAGAA ACAGTTCCAT TCAACTGGAA CATTTTTTTT    1178

TTTTCCTTTT AAGAAAGCTT CTTGTGATCC TTCGGGCTT CTGTG                     1223

(2) INFORMATION FOR SEQ ID NO:9:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:9:

Leu Leu Glu Asp Ser Pro Tyr Glu Pro Val Asn Ser Arg Leu Ser Asp
1               5                   10                  15

Ile Phe Arg Val Val Pro Phe Ile Ser Val Glu His Ile Pro Lys Gly
                20                  25                  30

Asn Asn Cys Leu Asp Ala Ala Lys Ala Cys Asn Leu Asp Asp Ile Cys
            35                  40                  45

Lys Lys Tyr Arg Ser Ala Tyr Ile Thr Pro Cys Thr Thr Ser Val Ser
    50                  55                  60

Asn Asp Val Cys Asn Arg Arg Lys Cys His Lys Ala Leu Arg Gln Phe
65                  70                  75                  80

Phe Asp Lys Val Pro Ala Lys His Ser Tyr Gly Met Leu Phe Cys Ser
                85                  90                  95

Cys Arg Asp Ile Ala Cys Thr Glu Arg Arg Arg Gln Thr Ile Val Pro
            100                 105                 110
```

```
Val Cys Ser Tyr Glu Glu Arg Glu Lys Pro Asn Cys Leu Asn Leu Gln
        115                 120                 125

Asp Ser Cys Lys Thr Asn Tyr Ile Cys Arg Ser Arg Leu Ala Asp Phe
    130                 135                 140

Phe Thr Asn Cys Gln Pro Glu Ser Arg Ser Val Ser Ser Cys Leu Lys
145                 150                 155                 160

Glu Asn Tyr Ala Asp Cys Leu Leu Ala Tyr Ser Gly Leu Ile Gly Thr
                165                 170                 175

Val Met Thr Pro Asn Tyr Ile Asp Ser Ser Ser Leu Ser Val Ala Pro
            180                 185                 190

Trp Cys Asp Cys Ser Asn Ser Gly Asn Asp Leu Glu Glu Cys Leu Lys
        195                 200                 205

Phe Leu Asn Phe Phe Lys Asp Asn Thr Cys Leu Lys Asn Ala Ile Gln
    210                 215                 220

Ala Phe Gly Asn Gly Ser Asp Val Thr Val Trp Gln Pro Ala Phe Pro
225                 230                 235                 240

Val Gln Thr Thr Thr Ala Thr Thr Thr Ala Leu Arg Val Lys Asn
                245                 250                 255

Lys Pro Leu Gly Pro Ala Gly Ser Glu Asn Glu Ile Pro Thr His Val
            260                 265                 270

Leu Pro Pro Cys Ala Asn Leu Gln Ala Gln Lys Leu Lys Ser Asn Val
        275                 280                 285

Ser Gly Asn Thr His Leu Cys Ile Ser Asn Gly Asn Tyr Glu Lys Glu
    290                 295                 300

Gly Leu Gly Ala Ser Ser His Ile Thr Thr Lys Ser Met Ala Ala Pro
305                 310                 315                 320

Pro Ser Cys Gly Leu Ser Pro Leu Leu Val Leu Val Thr Ala Leu
                325                 330                 335

Ser Thr Leu Leu Ser Leu Thr Glu Thr Ser
            340                 345

(2) INFORMATION FOR SEQ ID NO:10:

(i) SEQUENCE CHARACTERISTICS:
        (A) LENGTH: 1682 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 118..1497

(xi) SEQUENCE DESCRIPTION: SEQ ID NO:10:

GGGCGGCCAG AGCAGCACAG CTGTCCGGGG ATCGCTGCAT GCTGAGCTCC CTCGGCAAGA      60

CCCAGCGGCG GCTCGGGATT TTTTTGGGGG GGCGGGGACC AGCCCCGCGC CGGCACC        117

ATG TTC CTG GCG ACC CTG TAC TTC GCG CTG CCG CTC TTG GAC TTG CTC       165
Met Phe Leu Ala Thr Leu Tyr Phe Ala Leu Pro Leu Leu Asp Leu Leu
        350                 355                 360

CTG TCG GCC GAA GTG AGC GGC GGA GAC CGC CTG GAT TGC GTG AAA GCC       213
Leu Ser Ala Glu Val Ser Gly Gly Asp Arg Leu Asp Cys Val Lys Ala
        365                 370                 375

AGT GAT CAG TGC CTG AAG GAG CAG AGC TGC AGC ACC AAG TAC CGC ACG       261
Ser Asp Gln Cys Leu Lys Glu Gln Ser Cys Ser Thr Lys Tyr Arg Thr
    380                 385                 390

CTA AGG CAG TGC GTG GCG GGC AAG GAG ACC AAC TTC AGC CTG GCA TCC       309
```

```
                                             -continued

Leu Arg Gln Cys Val Ala Gly Lys Glu Thr Asn Phe Ser Leu Ala Ser
395                 400                 405                 410

GGC CTG GAG GCC AAG GAT GAG TGC CGC AGC GCC ATG GAG GCC CTG AAG      357
Gly Leu Glu Ala Lys Asp Glu Cys Arg Ser Ala Met Glu Ala Leu Lys
                    415                 420                 425

CAG AAG TCG CTC TAC AAC TGC CGC TGC AAG CGG GGT ATG AAG AAG GAG      405
Gln Lys Ser Leu Tyr Asn Cys Arg Cys Lys Arg Gly Met Lys Lys Glu
                430                 435                 440

AAG AAC TGC CTG CGC ATT TAC TGG AGC ATG TAC CAG AGC CTG CAG GGA      453
Lys Asn Cys Leu Arg Ile Tyr Trp Ser Met Tyr Gln Ser Leu Gln Gly
                445                 450                 455

AAT GAT CTG CTG GAG GAT TCC CCA TAT GAA CCA GTT AAC AGC AGA TTG      501
Asn Asp Leu Leu Glu Asp Ser Pro Tyr Glu Pro Val Asn Ser Arg Leu
460                 465                 470

TCA GAT ATA TTC CGG GTG GTC CCA TTC ATA TCA GTG GAG CAC ATT CCC      549
Ser Asp Ile Phe Arg Val Val Pro Phe Ile Ser Val Glu His Ile Pro
475                 480                 485                 490

AAA GGG AAC AAC TGC CTG GAT GCA GCG AAG GCC TGC AAC CTC GAC GAC      597
Lys Gly Asn Asn Cys Leu Asp Ala Ala Lys Ala Cys Asn Leu Asp Asp
                495                 500                 505

ATT TGC AAG AAG TAC AGG TCG GCG TAC ATC ACC CCG TGC ACC ACC AGC      645
Ile Cys Lys Lys Tyr Arg Ser Ala Tyr Ile Thr Pro Cys Thr Thr Ser
                510                 515                 520

GTG TCC AAC GAT GTC TGC AAC CGC CGC AAG TGC CAC AAG GCC CTC CGG      693
Val Ser Asn Asp Val Cys Asn Arg Arg Lys Cys His Lys Ala Leu Arg
                525                 530                 535

CAG TTC TTT GAC AAG GTC CCG GCC AAG CAC AGC TAC GGA ATG CTC TTC      741
Gln Phe Phe Asp Lys Val Pro Ala Lys His Ser Tyr Gly Met Leu Phe
                540                 545                 550

TGC TCC TGC CGG GAC ATC GCC TGC ACA GAG CGG AGG CGA CAG ACC ATC      789
Cys Ser Cys Arg Asp Ile Ala Cys Thr Glu Arg Arg Arg Gln Thr Ile
555                 560                 565                 570

GTG CCT GTG TGC TCC TAT GAA GAG AGG GAG AAG CCC AAC TGT TTG AAT      837
Val Pro Val Cys Ser Tyr Glu Glu Arg Glu Lys Pro Asn Cys Leu Asn
                575                 580                 585

TTG CAG GAC TCC TGC AAG ACG AAT TAC ATC TGC AGA TCT CGC CTT GCG      885
Leu Gln Asp Ser Cys Lys Thr Asn Tyr Ile Cys Arg Ser Arg Leu Ala
                590                 595                 600

GAT TTT TTT ACC AAC TGC CAG CCA GAG TCA AGG TCT GTC AGC AGC TGT      933
Asp Phe Phe Thr Asn Cys Gln Pro Glu Ser Arg Ser Val Ser Ser Cys
                605                 610                 615

CTA AAG GAA AAC TAC GCT GAC TGC CTC CTC GCC TAC TCG GGG CTT ATT      981
Leu Lys Glu Asn Tyr Ala Asp Cys Leu Leu Ala Tyr Ser Gly Leu Ile
                620                 625                 630

GGC ACA GTC ATG ACC CCC AAC TAC ATA GAC TCC AGT AGC CTC AGT GTG     1029
Gly Thr Val Met Thr Pro Asn Tyr Ile Asp Ser Ser Ser Leu Ser Val
635                 640                 645                 650

GCC CCA TGG TGT GAC TGC AGC AAC AGT GGG AAC GAC CTA GAA GAG TGC     1077
Ala Pro Trp Cys Asp Cys Ser Asn Ser Gly Asn Asp Leu Glu Glu Cys
                655                 660                 665

TTG AAA TTT TTG AAT TTC TTC AAG GAC AAT ACA TGT CTT AAA AAT GCA     1125
Leu Lys Phe Leu Asn Phe Phe Lys Asp Asn Thr Cys Leu Lys Asn Ala
                670                 675                 680

ATT CAA GCC TTT GGC AAT GGC TCC GAT GTG ACC GTG TGG CAG CCA GCC     1173
Ile Gln Ala Phe Gly Asn Gly Ser Asp Val Thr Val Trp Gln Pro Ala
                685                 690                 695

TTC CCA GTA CAG ACC ACC ACT GCC ACT ACC ACC ACT GCC CTC CGG GTT     1221
Phe Pro Val Gln Thr Thr Thr Ala Thr Thr Thr Thr Ala Leu Arg Val
                700                 705                 710
```

```
AAG AAC AAG CCC CTG GGG CCA GCA GGG TCT GAG AAT GAA ATT CCC ACT    1269
Lys Asn Lys Pro Leu Gly Pro Ala Gly Ser Glu Asn Glu Ile Pro Thr
715                 720                 725                 730

CAT GTT TTG CCA CCG TGT GCA AAT TTA CAG GCA CAG AAG CTG AAA TCC    1317
His Val Leu Pro Pro Cys Ala Asn Leu Gln Ala Gln Lys Leu Lys Ser
                735                 740                 745

AAT GTG TCG GGC AAT ACA CAC CTC TGT ATT TCC AAT GGT AAT TAT GAA    1365
Asn Val Ser Gly Asn Thr His Leu Cys Ile Ser Asn Gly Asn Tyr Glu
            750                 755                 760

AAA GAA GGT CTC GGT GCT TCC AGC CAC ATA ACC ACA AAA TCA ATG GCT    1413
Lys Glu Gly Leu Gly Ala Ser Ser His Ile Thr Thr Lys Ser Met Ala
        765                 770                 775

GCT CCT CCA AGC TGT GGT CTG AGC CCA CTG CTG GTC CTG GTG GTA ACC    1461
Ala Pro Pro Ser Cys Gly Leu Ser Pro Leu Leu Val Leu Val Val Thr
    780                 785                 790

GCT CTG TCC ACC CTA TTA TCT TTA ACA GAA ACA TCA TAGCTGCATT         1507
Ala Leu Ser Thr Leu Leu Ser Leu Thr Glu Thr Ser
795                 800                 805

AAAAAAATAC AATATGGACA TGTAAAAAGA CAAAAACCAA GTTATCTGTT TCCTGTTCTC  1567

TTGTATAGCT GAAATTCCAG TTTAGGAGCT CAGTTGAGAA ACAGTTCCAT TCAACTGGAA  1627

CATTTTTTTT TTTTCCTTTT AAGAAAGCTT CTTGTGATCC TTCGGGGCTT CTGTG       1682

(2) INFORMATION FOR SEQ ID NO:11:

(i) SEQUENCE CHARACTERISTICS:
        (A) LENGTH: 460 amino acids
        (B) TYPE: amino acid
        (D) TOPOLOGY: linear (ii) MOLECULE TYPE: protein (xi) SEQUENCE DESCRIPTION: SEQ ID NO:11:

Met Phe Leu Ala Thr Leu Tyr Phe Ala Leu Pro Leu Leu Asp Leu Leu
  1               5                  10                  15

Leu Ser Ala Glu Val Ser Gly Gly Asp Arg Leu Asp Cys Val Lys Ala
             20                  25                  30

Ser Asp Gln Cys Leu Lys Glu Gln Ser Cys Ser Thr Lys Tyr Arg Thr
         35                  40                  45

Leu Arg Gln Cys Val Ala Gly Lys Glu Thr Asn Phe Ser Leu Ala Ser
     50                  55                  60

Gly Leu Glu Ala Lys Asp Glu Cys Arg Ser Ala Met Glu Ala Leu Lys
 65                  70                  75                  80

Gln Lys Ser Leu Tyr Asn Cys Arg Cys Lys Arg Gly Met Lys Lys Glu
                 85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Val Glu His Ile Pro
    130                 135                 140

Lys Gly Asn Asn Cys Leu Asp Ala Ala Lys Ala Cys Asn Leu Asp Asp
145                 150                 155                 160

Ile Cys Lys Lys Tyr Arg Ser Ala Tyr Ile Thr Pro Cys Thr Thr Ser
                165                 170                 175

Val Ser Asn Asp Val Cys Asn Arg Arg Lys Cys His Lys Ala Leu Arg
            180                 185                 190

Gln Phe Phe Asp Lys Val Pro Ala Lys His Ser Tyr Gly Met Leu Phe
```

```
                195                 200                      205
Cys Ser Cys Arg Asp Ile Ala Cys Thr Glu Arg Arg Gln Thr Ile
    210                 215                 220

Val Pro Val Cys Ser Tyr Glu Glu Arg Glu Lys Pro Asn Cys Leu Asn
225                 230                 235                 240

Leu Gln Asp Ser Cys Lys Thr Asn Tyr Ile Cys Arg Ser Arg Leu Ala
                245                 250                 255

Asp Phe Phe Thr Asn Cys Gln Pro Glu Ser Arg Ser Val Ser Ser Cys
            260                 265                 270

Leu Lys Glu Asn Tyr Ala Asp Cys Leu Leu Ala Tyr Ser Gly Leu Ile
        275                 280                 285

Gly Thr Val Met Thr Pro Asn Tyr Ile Asp Ser Ser Leu Ser Val
    290                 295                 300

Ala Pro Trp Cys Asp Cys Ser Asn Ser Gly Asn Asp Leu Glu Cys
305                 310                 315                 320

Leu Lys Phe Leu Asn Phe Phe Lys Asp Asn Thr Cys Leu Lys Asn Ala
                325                 330                 335

Ile Gln Ala Phe Gly Asn Gly Ser Asp Val Thr Val Trp Gln Pro Ala
            340                 345                 350

Phe Pro Val Gln Thr Thr Thr Ala Thr Thr Thr Ala Leu Arg Val
        355                 360                 365

Lys Asn Lys Pro Leu Gly Pro Ala Gly Ser Glu Asn Glu Ile Pro Thr
370                 375                 380

His Val Leu Pro Pro Cys Ala Asn Leu Gln Ala Gln Lys Leu Lys Ser
385                 390                 395                 400

Asn Val Ser Gly Asn Thr His Leu Cys Ile Ser Asn Gly Asn Tyr Glu
                405                 410                 415

Lys Glu Gly Leu Gly Ala Ser Ser His Ile Thr Thr Lys Ser Met Ala
            420                 425                 430

Ala Pro Pro Ser Cys Gly Leu Ser Pro Leu Val Leu Val Val Thr
        435                 440                 445

Ala Leu Ser Thr Leu Leu Ser Leu Thr Glu Thr Ser
450                 455                 460
```

(2) INFORMATION FOR SEQ ID NO:12:

(i) SEQUENCE CHARACTERISTICS:
        (A) LENGTH: 1888 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 25..1416

(xi) SEQUENCE DESCRIPTION: SEQ ID NO:12:

```
AAAAAACGGT GGGATTTATT TAAC ATG ATC TTG GCA AAC GTC TTC TGC CTC          51
                         Met Ile Leu Ala Asn Val Phe Cys Leu
                                         465

TTC TTC TTT CTA GAC GAG ACC CTC CGC TCT TTG GCC AGC CCT TCC TCC         99
Phe Phe Phe Leu Asp Glu Thr Leu Arg Ser Leu Ala Ser Pro Ser Ser
470                 475                 480                 485

CTG CAG GGC CCC GAG CTC CAC GGC TGG CGC CCC CCA GTG GAC TGT GTC        147
Leu Gln Gly Pro Glu Leu His Gly Trp Arg Pro Pro Val Asp Cys Val
                490                 495                 500
```

```
CGG GCC AAT GAG CTG TGT GCC GCC GAA TCC AAC TGC AGC TCT CGC TAC        195
Arg Ala Asn Glu Leu Cys Ala Ala Glu Ser Asn Cys Ser Ser Arg Tyr
            505                 510                 515

CGC ACT CTG CGG CAG TGC CTG GCA GGC CGC GAC CGC AAC ACC ATG CTG        243
Arg Thr Leu Arg Gln Cys Leu Ala Gly Arg Asp Arg Asn Thr Met Leu
        520                 525                 530

GCC AAC AAG GAG TGC CAG GCG GCC TTG GAG GTC TTG CAG GAG AGC CCG        291
Ala Asn Lys Glu Cys Gln Ala Ala Leu Glu Val Leu Gln Glu Ser Pro
535                 540                 545

CTG TAC GAC TGC CGC TGC AAG CGG GGC ATG AAG AAG GAG CTG CAG TGT        339
Leu Tyr Asp Cys Arg Cys Lys Arg Gly Met Lys Lys Glu Leu Gln Cys
550                 555                 560                 565

CTG CAG ATC TAC TGG AGC ATC CAC CTG GGG CTG ACC GAG GGT GAG GAG        387
Leu Gln Ile Tyr Trp Ser Ile His Leu Gly Leu Thr Glu Gly Glu Glu
            570                 575                 580

TTC TAC GAA GCC TCC CCC TAT GAG CCG GTG ACC TCC CGC CTC TCG GAC        435
Phe Tyr Glu Ala Ser Pro Tyr Glu Pro Val Thr Ser Arg Leu Ser Asp
            585                 590                 595

ATC TTC AGG CTT GCT TCA ATC TTC TCA GGG ACA GGG GCA GAC CCG GTG        483
Ile Phe Arg Leu Ala Ser Ile Phe Ser Gly Thr Gly Ala Asp Pro Val
            600                 605                 610

GTC AGC GCC AAG AGC AAC CAT TGC CTG GAT GCT GCC AAG GCC TGC AAC        531
Val Ser Ala Lys Ser Asn His Cys Leu Asp Ala Ala Lys Ala Cys Asn
615                 620                 625

CTG AAT GAC AAC TGC AAG AAG CTG CGC TCC TCC TAC ATC TCC ATC TGC        579
Leu Asn Asp Asn Cys Lys Lys Leu Arg Ser Ser Tyr Ile Ser Ile Cys
630                 635                 640                 645

AAC CGC GAG ATC TCG CCC ACC GAG CGC TGC AAC CGC CGC AAG TGC CAC        627
Asn Arg Glu Ile Ser Pro Thr Glu Arg Cys Asn Arg Arg Lys Cys His
            650                 655                 660

AAG GCC CTG CGC CAG TTC TTC GAC CGG GTG CCC AGC GAG TAC ACC TAC        675
Lys Ala Leu Arg Gln Phe Phe Asp Arg Val Pro Ser Glu Tyr Thr Tyr
            665                 670                 675

CGC ATG CTC TTC TGC TCC TGC CAA GAC CAG GCG TGC GCT GAG CGC CGC        723
Arg Met Leu Phe Cys Ser Cys Gln Asp Gln Ala Cys Ala Glu Arg Arg
            680                 685                 690

CGG CAA ACC ATC CTG CCC AGC TGC TCC TAT GAG GAC AAG GAG AAG CCC        771
Arg Gln Thr Ile Leu Pro Ser Cys Ser Tyr Glu Asp Lys Glu Lys Pro
            695                 700                 705

AAC TGC CTG GAC CTG CGT GGC GTG TGC CGG ACT GAC CAC CTG TGT CGG        819
Asn Cys Leu Asp Leu Arg Gly Val Cys Arg Thr Asp His Leu Cys Arg
710                 715                 720                 725

TCC CGG CTG GCC GAC TTC CAT GCC AAT TGT CGA GCC TCC TAC CAG ACG        867
Ser Arg Leu Ala Asp Phe His Ala Asn Cys Arg Ala Ser Tyr Gln Thr
            730                 735                 740

GTC ACC AGC TGC CCT GCG GAC AAT TAC CAG GCG TGT CTG GGC TCT TAT        915
Val Thr Ser Cys Pro Ala Asp Asn Tyr Gln Ala Cys Leu Gly Ser Tyr
            745                 750                 755

GCT GGC ATG ATT GGG TTT GAC ATG ACA CCT AAC TAT GTG GAC TCC AGC        963
Ala Gly Met Ile Gly Phe Asp Met Thr Pro Asn Tyr Val Asp Ser Ser
            760                 765                 770

CCC ACT GGC ATC GTG GTG TCC CCC TGG TGC AGC TGT CGT GGC AGC GGG       1011
Pro Thr Gly Ile Val Val Ser Pro Trp Cys Ser Cys Arg Gly Ser Gly
            775                 780                 785

AAC ATG GAG GAG GAG TGT GAG AAG TTC CTC AGG GAC TTC ACC GAG AAC       1059
Asn Met Glu Glu Glu Cys Glu Lys Phe Leu Arg Asp Phe Thr Glu Asn
790                 795                 800                 805

CCA TGC CTC CGG AAC GCC ATC CAG GCC TTT GGC AAC GGC ACG GAC GTG       1107
Pro Cys Leu Arg Asn Ala Ile Gln Ala Phe Gly Asn Gly Thr Asp Val
            810                 815                 820
```

```
AAC GTG TCC CCA AAA GGC CCC TCG TTC CAG GCC ACC CAG GCC CCT CGG         1155
Asn Val Ser Pro Lys Gly Pro Ser Phe Gln Ala Thr Gln Ala Pro Arg
            825                 830                 835

GTG GAG AAG ACG CCT TCT TTG CCA GAT GAC CTC AGT GAC AGT ACC AGC         1203
Val Glu Lys Thr Pro Ser Leu Pro Asp Asp Leu Ser Asp Ser Thr Ser
            840                 845                 850

TTG GGG ACC AGT GTC ATC ACC ACC TGC ACG TCT GTC CAG GAG CAG GGG         1251
Leu Gly Thr Ser Val Ile Thr Thr Cys Thr Ser Val Gln Glu Gln Gly
            855                 860                 865

CTG AAG GCC AAC AAC TCC AAA GAG TTA AGC ATG TGC TTC ACA GAG CTC         1299
Leu Lys Ala Asn Asn Ser Lys Glu Leu Ser Met Cys Phe Thr Glu Leu
870                 875                 880                 885

ACG ACA AAT ATC ATC CCA GGG AGT AAC AAG GTG ATC AAA CCT AAC TCA         1347
Thr Thr Asn Ile Ile Pro Gly Ser Asn Lys Val Ile Lys Pro Asn Ser
                890                 895                 900

GGC CCC AGC AGA GCC AGA CCG TCG GCT GCC TTG ACC GTG CTG TCT GTC         1395
Gly Pro Ser Arg Ala Arg Pro Ser Ala Ala Leu Thr Val Leu Ser Val
                905                 910                 915

CTG ATG CTG AAA CTG GCC TTG TAGGCTGTGG GAACCGAGTC AGAAGATTTT            1446
Leu Met Leu Lys Leu Ala Leu
                920

TGAAAGCTAC GCAGACAAGA ACAGCCGCCT GACGAAATGG AAACACACAC AGACACACAC       1506

ACACCTTGCA AAAAAAAAT TGTTTTTCCC ACCTTGTCGC TGAACCTGTC TCCTCCCAGG        1566

TTTCTTCTCT GGAGAAGTTT TTGTAAACCA AACAGACAAG CAGGCAGGCA GCCTGAGAGC       1626

TGGCCCAGGG GTCCCCTGGC AGGGGAAACT CTGGTGCCGG GGAGGGCACG AGGCTCTAGA       1686

AATGCCCTTC ACTTTCTCCT GGTGTTTTTC TCTCTGGACC CTTCTGAAGC AGAGACCGGA       1746

CAAGAGCCTG CAGCGGAAGG GACTCTGGGC TGTGCCTGAG GCTGGCTGGG GGCAGGACAA       1806

CACAGCTGCT TCCCCAGGCT GCCCACTCTG GGACCCGCT GGGGGCTGGC AGAGGGCATC       1866

GGTCAGCGGG GCAGCGGGGC TG                                                1888

(2) INFORMATION FOR SEQ ID NO:13:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO:13:

Met Ile Leu Ala Asn Val Phe Cys Leu Phe Phe Leu Asp Glu Thr
 1               5                  10                  15

Leu Arg Ser Leu Ala Ser Pro Ser Ser Leu Gln Gly Pro Glu Leu His
                20                  25                  30

Gly Trp Arg Pro Pro Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
    50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
                100                 105                 110

His Leu Gly Leu Thr Glu Gly Glu Glu Phe Tyr Glu Ala Ser Pro Tyr
```

```
                    115                 120                 125
Glu Pro Val Thr Ser Arg Leu Ser Asp Ile Phe Arg Leu Ala Ser Ile
130                 135                 140

Phe Ser Gly Thr Gly Ala Asp Pro Val Val Ser Ala Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
                180                 185                 190

Glu Arg Cys Asn Arg Arg Lys Cys His Lys Ala Leu Arg Gln Phe Phe
                195                 200                 205

Asp Arg Val Pro Ser Glu Tyr Thr Tyr Arg Met Leu Phe Cys Ser Cys
210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Gly
                245                 250                 255

Val Cys Arg Thr Asp His Leu Cys Arg Ser Arg Leu Ala Asp Phe His
                260                 265                 270

Ala Asn Cys Arg Ala Ser Tyr Gln Thr Val Thr Ser Cys Pro Ala Asp
                275                 280                 285

Asn Tyr Gln Ala Cys Leu Gly Ser Tyr Ala Gly Met Ile Gly Phe Asp
290                 295                 300

Met Thr Pro Asn Tyr Val Asp Ser Ser Pro Thr Gly Ile Val Val Ser
305                 310                 315                 320

Pro Trp Cys Ser Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
                340                 345                 350

Gln Ala Phe Gly Asn Gly Thr Asp Val Asn Val Ser Pro Lys Gly Pro
                355                 360                 365

Ser Phe Gln Ala Thr Gln Ala Pro Arg Val Glu Lys Thr Pro Ser Leu
                370                 375                 380

Pro Asp Asp Leu Ser Asp Ser Thr Ser Leu Gly Thr Ser Val Ile Thr
385                 390                 395                 400

Thr Cys Thr Ser Val Gln Glu Gln Gly Leu Lys Ala Asn Asn Ser Lys
                405                 410                 415

Glu Leu Ser Met Cys Phe Thr Glu Leu Thr Thr Asn Ile Ile Pro Gly
                420                 425                 430

Ser Asn Lys Val Ile Lys Pro Asn Ser Gly Pro Ser Arg Ala Arg Pro
                435                 440                 445

Ser Ala Ala Leu Thr Val Leu Ser Val Leu Met Leu Lys Leu Ala Leu
450                 455                 460
```

(2) INFORMATION FOR SEQ ID NO:14:

(i) SEQUENCE CHARACTERISTICS:
        (A) LENGTH: 1878 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 205..1242

(xi) SEQUENCE DESCRIPTION: SEQ ID NO:14:

```
CGCGGCGCCC AGCGCAGGCA GAGCGCTGTC GCATCCCGGG CGTCCACCCG CCATGGGGCT        60

CTCCTGGAGC CCGCGACCTC CACTGCTGAT GATCCTGCTA CTGGTGCTGT CGTTGTGGCT       120

GCCACTTGGA GCAGGAAACT CCCTTGCCAC AGAGAACAGG TTTGTGAACA GCTGTACCCA       180

GGCCAGAAAG AAATGCGAGG CTAA TCC CGC TTG CAA GGC TGC CTA CCA GCA         231
                          Ser Arg Leu Gln Gly Cys Leu Pro Ala
                          465                 470

CCT GGG CTC CTG CAC CTC CAG TTA AGC AGG CCG CTG CCC TTA GAG GAG         279
Pro Gly Leu Leu His Leu Gln Leu Ser Arg Pro Leu Pro Leu Glu Glu
    475                 480                 485

TCT GCC ATG TCT GCA GAC TGC CTA GAG GCA GCA GAA CAA CTC AGG AAC         327
Ser Ala Met Ser Ala Asp Cys Leu Glu Ala Ala Glu Gln Leu Arg Asn
490                 495                 500                 505

AGC TCT CTG ATA GAC TGC AGG TGC CAT CGG CGC ATG AAG CAC CAA GCT         375
Ser Ser Leu Ile Asp Cys Arg Cys His Arg Arg Met Lys His Gln Ala
                510                 515                 520

ACC TGT CTG GAC ATT TAT TGG ACC GTT CAC CCT GCC CGA AGC CTT GGT         423
Thr Cys Leu Asp Ile Tyr Trp Thr Val His Pro Ala Arg Ser Leu Gly
        525                 530                 535

GAC TAC GAG TTG GAT GTC TCA CCC TAT GAA GAC ACA GTG ACC AGC AAA         471
Asp Tyr Glu Leu Asp Val Ser Pro Tyr Glu Asp Thr Val Thr Ser Lys
    540                 545                 550

CCC TGG AAA ATG AAT CTT AGC AAG TTG AAC ATG CTC AAA CCA GAC TCG         519
Pro Trp Lys Met Asn Leu Ser Lys Leu Asn Met Leu Lys Pro Asp Ser
555                 560                 565

GAC CTC TGC CTC AAA TTT GCT ATG CTG TGT ACT CTT CAC GAC AAG TGT         567
Asp Leu Cys Leu Lys Phe Ala Met Leu Cys Thr Leu His Asp Lys Cys
570                 575                 580                 585

GAC CGC CTG CGC AAG GCC TAC GGG GAG GCA TGC TCA GGG ATC CGC TGC         615
Asp Arg Leu Arg Lys Ala Tyr Gly Glu Ala Cys Ser Gly Ile Arg Cys
                590                 595                 600

CAG CGC CAC CTC TGC CTA GCC CAG CTG CGC TCC TTC TTT GAG AAG GCA         663
Gln Arg His Leu Cys Leu Ala Gln Leu Arg Ser Phe Phe Glu Lys Ala
            605                 610                 615

GCA GAG TCC CAC GCT CAG GGT CTG CTG CTG TGT CCC TGT GCA CCA GAA         711
Ala Glu Ser His Ala Gln Gly Leu Leu Leu Cys Pro Cys Ala Pro Glu
            620                 625                 630

GAT GCG GGC TGT GGG GAG CGG CGG CGT AAC ACC ATC GCC CCC AGT TGC         759
Asp Ala Gly Cys Gly Glu Arg Arg Arg Asn Thr Ile Ala Pro Ser Cys
635                 640                 645

GCC CTG CCT TCT GTA ACC CCC AAT TGC CTG GAT CTG CGG AGC TTC TGC         807
Ala Leu Pro Ser Val Thr Pro Asn Cys Leu Asp Leu Arg Ser Phe Cys
650                 655                 660                 665

CGT GCG GAC CCT TTG TGC AGA TCA CGC CTG ATG GAC TTC CAG ACC CAC         855
Arg Ala Asp Pro Leu Cys Arg Ser Arg Leu Met Asp Phe Gln Thr His
                670                 675                 680

TGT CAT CCT ATG GAC ATC TTG GGA ACT TGT GCA ACT GAG CAG TCC AGA         903
Cys His Pro Met Asp Ile Leu Gly Thr Cys Ala Thr Glu Gln Ser Arg
            685                 690                 695

TGT CTG CGG GCA TAC CTG GGG CTG ATT GGG ACT GCC ATG ACC CCA AAC         951
Cys Leu Arg Ala Tyr Leu Gly Leu Ile Gly Thr Ala Met Thr Pro Asn
            700                 705                 710

TTC ATC AGC AAG GTC AAC ACT ACT GTT GCC TTA AGC TGC ACC TGC CGA         999
Phe Ile Ser Lys Val Asn Thr Thr Val Ala Leu Ser Cys Thr Cys Arg
        715                 720                 725

GGC AGC GGC AAC CTA CAG GAC GAG TGT GAA CAG CTG GAA AGG TCC TTC        1047
Gly Ser Gly Asn Leu Gln Asp Glu Cys Glu Gln Leu Glu Arg Ser Phe
```

```
730              735                 740                 745
TCC CAG AAC CCC TGC CTC GTG GAG GCC ATT GCA GCT AAG ATG CGT TTC   1095
Ser Gln Asn Pro Cys Leu Val Glu Ala Ile Ala Ala Lys Met Arg Phe
            750                 755                 760

CAC AGA CAG CTC TTC TCC CAG GAC TGG GCA GAC TCT ACT TTT TCA GTG   1143
His Arg Gln Leu Phe Ser Gln Asp Trp Ala Asp Ser Thr Phe Ser Val
        765                 770                 775

GTG CAG CAG CAG AAC AGC AAC CCT GCT CTG AGA CTG CAG CCC AGG CTA   1191
Val Gln Gln Gln Asn Ser Asn Pro Ala Leu Arg Leu Gln Pro Arg Leu
        780                 785                 790

CCC ATT CTT TCT TTC TCC ATC CTT CCC TTG ATT CTG CTG CAG ACC CTC   1239
Pro Ile Leu Ser Phe Ser Ile Leu Pro Leu Ile Leu Leu Gln Thr Leu
    795                 800                 805

TGG TAGCTGGGCT TCCTCAGGGT CCTTTGTCCT CTCCACCACA CCCAGACTGA         1292
Trp
810

TTTGCAGCCT GTGGTGGGAG AGAACTCGCC AGCCTGTGGA AGAAGACGCA GCGTGCTACA   1352

CAGCAACCCG GAACCAACCA GGCATTCCGC AGCACATCCC GTCTGCTCCA GAAGAGGTCT   1412

TAGAAGTGAG GGCTGTGACC CTTCCGATCC TGAGCGGCTA GTTTTCAAAC CTCCCTTGCC   1472

CCTGCTTCCT TCTGGCTCAG GCTGCTCCTC CTTAGGACTT TGTGGGTCCA GTTTTGCCTT   1532

CTGTTCTGAT GGTGATTAGC GGCTCACCTC CAGCGCTTCT TCCTGTTTCC CAGGACCACC   1592

CAGAGGCTAA GGAATCAGTC ATTCCCTGTT GCCTTCTCCA GGAAGGCAGG CTAAGGGTTC   1652

TGAGGTGACT GAGAAAAATG TTTCCTTTGT GTGGAAGGCT GGTGCTCCAG CCTCCACGTC   1712

CCTCTGAATG GAAGATAAAA ACCTGCTGGT GTCTTGACTG CTCTGCCAGG CAATCCTGAA   1772

CATTTGGGCA TGAAGAGCTA AAGTCTTTGG GTCTTGTTTA ACTCCTATTA CTGTCCCCAA   1832

ATTCCCCTAG TCCCTTGGGT CATGATTAAA CATTTTGACT TAAAAA                 1878

(2) INFORMATION FOR SEQ ID NO:15:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:15:

Ser Arg Leu Gln Gly Cys Leu Pro Ala Pro Gly Leu Leu His Leu Gln
1                   5                   10                  15

Leu Ser Arg Pro Leu Pro Leu Glu Glu Ser Ala Met Ser Ala Asp Cys
                20                  25                  30

Leu Glu Ala Ala Glu Gln Leu Arg Asn Ser Ser Leu Ile Asp Cys Arg
            35                  40                  45

Cys His Arg Arg Met Lys His Gln Ala Thr Cys Leu Asp Ile Tyr Trp
        50                  55                  60

Thr Val His Pro Ala Arg Ser Leu Gly Asp Tyr Glu Leu Asp Val Ser
65                  70                  75                  80

Pro Tyr Glu Asp Thr Val Thr Ser Lys Pro Trp Lys Met Asn Leu Ser
                85                  90                  95

Lys Leu Asn Met Leu Lys Pro Asp Ser Asp Leu Cys Leu Lys Phe Ala
                100                 105                 110

Met Leu Cys Thr Leu His Asp Lys Cys Asp Arg Leu Arg Lys Ala Tyr
            115                 120                 125

Gly Glu Ala Cys Ser Gly Ile Arg Cys Gln Arg His Leu Cys Leu Ala
```

```
              130                 135                 140
Gln Leu Arg Ser Phe Phe Glu Lys Ala Ala Glu Ser His Ala Gln Gly
145                 150                 155                 160

Leu Leu Leu Cys Pro Cys Ala Pro Glu Asp Ala Gly Cys Gly Glu Arg
                165                 170                 175

Arg Arg Asn Thr Ile Ala Pro Ser Cys Ala Leu Pro Ser Val Thr Pro
                180                 185                 190

Asn Cys Leu Asp Leu Arg Ser Phe Cys Arg Ala Asp Pro Leu Cys Arg
                195                 200                 205

Ser Arg Leu Met Asp Phe Gln Thr His Cys His Pro Met Asp Ile Leu
                210                 215                 220

Gly Thr Cys Ala Thr Glu Gln Ser Arg Cys Leu Arg Ala Tyr Leu Gly
225                 230                 235                 240

Leu Ile Gly Thr Ala Met Thr Pro Asn Phe Ile Ser Lys Val Asn Thr
                245                 250                 255

Thr Val Ala Leu Ser Cys Thr Cys Arg Gly Ser Gly Asn Leu Gln Asp
                260                 265                 270

Glu Cys Glu Gln Leu Glu Arg Ser Phe Ser Gln Asn Pro Cys Leu Val
                275                 280                 285

Glu Ala Ile Ala Ala Lys Met Arg Phe His Arg Gln Leu Phe Ser Gln
                290                 295                 300

Asp Trp Ala Asp Ser Thr Phe Ser Val Val Gln Gln Asn Ser Asn
305                 310                 315                 320

Pro Ala Leu Arg Leu Gln Pro Arg Leu Pro Ile Leu Ser Phe Ser Ile
                325                 330                 335

Leu Pro Leu Ile Leu Leu Gln Thr Leu Trp
                340                 345

(2) INFORMATION FOR SEQ ID NO:16:

(i) SEQUENCE CHARACTERISTICS:
        (A) LENGTH: 1889 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 41..1231

(xi) SEQUENCE DESCRIPTION: SEQ ID NO:16:

CGCAGGCAGA GCGCTGTCGC ATCCCGGGCG TCCACCCGCC ATG GGG CTC TCC TGG      55
                                            Met Gly Leu Ser Trp
                                                            350

AGC CCG CGA CCT CCA CTG CTG ATG ATC CTG CTA CTG GTG CTG TCG TTG     103
Ser Pro Arg Pro Pro Leu Leu Met Ile Leu Leu Leu Val Leu Ser Leu
                355                 360                 365

TGG CTG CCA CTT GGA GCA GGA AAC TCC CTT GCC ACA GAG AAC AGG TTT     151
Trp Leu Pro Leu Gly Ala Gly Asn Ser Leu Ala Thr Glu Asn Arg Phe
                370                 375                 380

GTG AAC AGC TGT ACC CAG GCC AGA AAG AAA TGC GAG GCT AAT CCC GCT     199
Val Asn Ser Cys Thr Gln Ala Arg Lys Lys Cys Glu Ala Asn Pro Ala
                385                 390                 395

TGC AAG GCT GCC TAC CAG CAC CTG GGC TCC TGC ACC TCC AGT TTA AGC     247
Cys Lys Ala Ala Tyr Gln His Leu Gly Ser Cys Thr Ser Ser Leu Ser
400                 405                 410                 415

AGG CCG CTG CCC TTA GAG GAG TCT GCC ATG TCT GCA GAC TGC CTA GAG     295
```

```
                        -continued

Arg Pro Leu Pro Leu Glu Glu Ser Ala Met Ser Ala Asp Cys Leu Glu
            420                 425                 430

GCA GCA GAA CAA CTC AGG AAC AGC TCT CTG ATA GAC TGC AGG TGC CAT        343
Ala Ala Glu Gln Leu Arg Asn Ser Ser Leu Ile Asp Cys Arg Cys His
            435                 440                 445

CGG CGC ATG AAG CAC CAA GCT ACC TGT CTG GAC ATT TAT TGG ACC GTT        391
Arg Arg Met Lys His Gln Ala Thr Cys Leu Asp Ile Tyr Trp Thr Val
            450                 455                 460

CAC CCT GCC CGA AGC CTT GGT GAC TAC GAG TTG GAT GTC TCA CCC TAT        439
His Pro Ala Arg Ser Leu Gly Asp Tyr Glu Leu Asp Val Ser Pro Tyr
            465                 470                 475

GAA GAC ACA GTG ACC AGC AAA CCC TGG AAA ATG AAT CTT AGC AAG TTG        487
Glu Asp Thr Val Thr Ser Lys Pro Trp Lys Met Asn Leu Ser Lys Leu
480                 485                 490                 495

AAC ATG CTC AAA CCA GAC TCG GAC CTC TGC CTC AAA TTT GCT ATG CTG        535
Asn Met Leu Lys Pro Asp Ser Asp Leu Cys Leu Lys Phe Ala Met Leu
                    500                 505                 510

TGT ACT CTT CAC GAC AAG TGT GAC CGC CTG CGC AAG GCC TAC GGG GAG        583
Cys Thr Leu His Asp Lys Cys Asp Arg Leu Arg Lys Ala Tyr Gly Glu
                515                 520                 525

GCA TGC TCA GGG ATC CGC TGC CAG CGC CAC CTC TGC CTA GCC CAG CTG        631
Ala Cys Ser Gly Ile Arg Cys Gln Arg His Leu Cys Leu Ala Gln Leu
            530                 535                 540

CGC TCC TTC TTT GAG AAG GCA GCA GAG TCC CAC GCT CAG GGT CTG CTG        679
Arg Ser Phe Phe Glu Lys Ala Ala Glu Ser His Ala Gln Gly Leu Leu
545                 550                 555

CTG TGT CCC TGT GCA CCA GAA GAT GCG GGC TGT GGG GAG CGG CGG CGT        727
Leu Cys Pro Cys Ala Pro Glu Asp Ala Gly Cys Gly Glu Arg Arg Arg
560                 565                 570                 575

AAC ACC ATC GCC CCC AGT TGC GCC CTG CCT TCT GTA ACC CCC AAT TGC        775
Asn Thr Ile Ala Pro Ser Cys Ala Leu Pro Ser Val Thr Pro Asn Cys
                580                 585                 590

CTG GAT CTG CGG AGC TTC TGC CGT GCG GAC CCT TTG TGC AGA TCA CGC        823
Leu Asp Leu Arg Ser Phe Cys Arg Ala Asp Pro Leu Cys Arg Ser Arg
                595                 600                 605

CTG ATG GAC TTC CAG ACC CAC TGT CAT CCT ATG GAC ATC CTT GGG ACT        871
Leu Met Asp Phe Gln Thr His Cys His Pro Met Asp Ile Leu Gly Thr
            610                 615                 620

TGT GCA ACT GAG CAG TCC AGA TGT CTG CGG GCA TAC CTG GGG CTG ATT        919
Cys Ala Thr Glu Gln Ser Arg Cys Leu Arg Ala Tyr Leu Gly Leu Ile
        625                 630                 635

GGG ACT GCC ATG ACC CCA AAC TTC ATC AGC AAG GTC AAC ACT ACT GTT        967
Gly Thr Ala Met Thr Pro Asn Phe Ile Ser Lys Val Asn Thr Thr Val
640                 645                 650                 655

GCC TTA AGC TGC ACC TGC CGA GGC AGC GGC AAC CTA CAG GAC GAG TGT       1015
Ala Leu Ser Cys Thr Cys Arg Gly Ser Gly Asn Leu Gln Asp Glu Cys
                660                 665                 670

GAA CAG CTG GAA AGG TCC TTC TCC CAG AAC CCC TGC CTC GTG GAG GCC       1063
Glu Gln Leu Glu Arg Ser Phe Ser Gln Asn Pro Cys Leu Val Glu Ala
            675                 680                 685

ATT GCA GCT AAG ATG CGT TTC CAC AGA CAG CTC TTC TCC CAG GAC TGG       1111
Ile Ala Ala Lys Met Arg Phe His Arg Gln Leu Phe Ser Gln Asp Trp
            690                 695                 700

GCA GAC TCT ACT TTT TCA GTG GTG CAG CAG CAG AAC AGC AAC CCT GCT       1159
Ala Asp Ser Thr Phe Ser Val Val Gln Gln Gln Asn Ser Asn Pro Ala
        705                 710                 715

CTG AGA CTG CAG CCC AGG CTA CCC ATT CTT TCT TTC TCC ATC CTT CCC       1207
Leu Arg Leu Gln Pro Arg Leu Pro Ile Leu Ser Phe Ser Ile Leu Pro
720                 725                 730                 735
```

-continued

```
TTG ATT CTG CTG CAG ACC CTC TGG TAGCTGGGCT TCCTCAGGGT CCTTTGTCCT    1261
Leu Ile Leu Leu Gln Thr Leu Trp
            740

CTCCACCACA CCCAGACTGA TTTGCAGCCT GTGGTGGGAG AGAACTCGCC AGCCTGTGGA    1321

AGAAGACGCA GCGTGCTACA CAGCAACCCG GAACCAACCA GGCATTCCGC AGCACATCCC    1381

GTCTGCTCCA GAAGAGGTCT TAGAAGTGAG GGCTGTGACC CTTCCGATCC TGAGCGGCTA    1441

GTTTTCAAAC CTCCCTTGCC CCTGCTTCCT TCTGGCTCAG GCTGCTCCTC CTTAGGACTT    1501

TGTGGGTCCA GTTTTGCCTT CTGTTCTGAT GGTGATTAGC GGCTCACCTC CAGCGCTTCT    1561

TCCTGTTTCC CAGGACCACC CAGAGGCTAA GGAATCAGTC ATTCCCTGTT GCCTTCTCCA    1621

GGAAGGCAGG CTAAGGGTTC TGAGGTGACT GAGAAAAATG TTTCCTTTGT GTGGAAGGCT    1681

GGTGCTCCAG CCTCCACGTC CCTCTGAATG GAAGATAAAA ACCTGCTGGT GTCTTGACTG    1741

CTCTGCCAGG CAATCCTGAA CATTTGGGCA TGAAGAGCTA AAGTCTTTGG GTCTTGTTTA    1801

ACTCCTATTA CTGTCCCCAA ATTCCCCTAG TCCCTTGGGT CATGATTAAA CATTTTGACT    1861

TAAAAAAAAA AAAAAAAAA AAAAAAA                                        1889
```

(2) INFORMATION FOR SEQ ID NO:17:

(i) SEQUENCE CHARACTERISTICS:
(A) LENGTH: 397 amino acids
(B) TYPE: amino acid
(D) TOPOLOGY: linear (ii) MOLECULE TYPE: protein (xi) SEQUENCE DESCRIPTION: SEQ ID NO:17:

```
Met Gly Leu Ser Trp Ser Pro Arg Pro Leu Leu Met Ile Leu Leu
  1               5                  10                  15

Leu Val Leu Ser Leu Trp Leu Pro Leu Gly Ala Gly Asn Ser Leu Ala
                 20                  25                  30

Thr Glu Asn Arg Phe Val Asn Ser Cys Thr Gln Ala Arg Lys Lys Cys
             35                  40                  45

Glu Ala Asn Pro Ala Cys Lys Ala Ala Tyr Gln His Leu Gly Ser Cys
 50                  55                  60

Thr Ser Ser Leu Ser Arg Pro Leu Pro Leu Glu Glu Ser Ala Met Ser
 65                  70                  75                  80

Ala Asp Cys Leu Glu Ala Ala Glu Gln Leu Arg Asn Ser Ser Leu Ile
                 85                  90                  95

Asp Cys Arg Cys His Arg Arg Met Lys His Gln Ala Thr Cys Leu Asp
             100                 105                 110

Ile Tyr Trp Thr Val His Pro Ala Arg Ser Leu Gly Asp Tyr Glu Leu
         115                 120                 125

Asp Val Ser Pro Tyr Glu Asp Thr Val Thr Ser Lys Pro Trp Lys Met
     130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
                 165                 170                 175

Lys Ala Tyr Gly Glu Ala Cys Ser Gly Ile Arg Cys Gln Arg His Leu
             180                 185                 190

Cys Leu Ala Gln Leu Arg Ser Phe Phe Glu Lys Ala Ala Glu Ser His
         195                 200                 205

Ala Gln Gly Leu Leu Leu Cys Pro Cys Ala Pro Glu Asp Ala Gly Cys
     210                 215                 220
```

```
Gly Glu Arg Arg Arg Asn Thr Ile Ala Pro Ser Cys Ala Leu Pro Ser
225                 230                 235                 240

Val Thr Pro Asn Cys Leu Asp Leu Arg Ser Phe Cys Arg Ala Asp Pro
            245                 250                 255

Leu Cys Arg Ser Arg Leu Met Asp Phe Gln Thr His Cys His Pro Met
        260                 265                 270

Asp Ile Leu Gly Thr Cys Ala Thr Glu Gln Ser Arg Cys Leu Arg Ala
    275                 280                 285

Tyr Leu Gly Leu Ile Gly Thr Ala Met Thr Pro Asn Phe Ile Ser Lys
290                 295                 300

Val Asn Thr Thr Val Ala Leu Ser Cys Thr Cys Arg Gly Ser Gly Asn
305                 310                 315                 320

Leu Gln Asp Glu Cys Glu Gln Leu Glu Arg Ser Phe Ser Gln Asn Pro
                325                 330                 335

Cys Leu Val Glu Ala Ile Ala Ala Lys Met Arg Phe His Arg Gln Leu
            340                 345                 350

Phe Ser Gln Asp Trp Ala Asp Ser Thr Phe Ser Val Val Gln Gln Gln
        355                 360                 365

Asn Ser Asn Pro Ala Leu Arg Leu Gln Pro Arg Leu Pro Ile Leu Ser
    370                 375                 380

Phe Ser Ile Leu Pro Leu Ile Leu Leu Gln Thr Leu Trp
385                 390                 395

(2) INFORMATION FOR SEQ ID NO:18:

(i) SEQUENCE CHARACTERISTICS:
        (A) LENGTH: 1271 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..946

(xi) SEQUENCE DESCRIPTION: SEQ ID NO:18:

C GGC TAC TGT GAA ACA CCT CAA CTC AGG AAC AGC TCT CTG ATA GGC         46
  Gly Tyr Cys Glu Thr Pro Gln Leu Arg Asn Ser Ser Leu Ile Gly
              400                 405                 410

TGC ATG TGC CAC CGG CGC ATG AAG AAC CAG GTT GCC TGC TTG GAC ATC       94
Cys Met Cys His Arg Arg Met Lys Asn Gln Val Ala Cys Leu Asp Ile
            415                 420                 425

TAT TGG ACC GTT CAC CGT GCC CGC AGC CTT GGT AAC TAT GAG CTG GAT      142
Tyr Trp Thr Val His Arg Ala Arg Ser Leu Gly Asn Tyr Glu Leu Asp
        430                 435                 440

GTC TCC CCC TAT GAA GAC ACA GTG ACC AGC AAA CCC TGG AAA ATG AAT      190
Val Ser Pro Tyr Glu Asp Thr Val Thr Ser Lys Pro Trp Lys Met Asn
445                 450                 455                 460

CTC AGC AAA CTG AAC ATG CTC AAA CCA GAC TCA GAC CTC TGC CTC AAG      238
Leu Ser Lys Leu Asn Met Leu Lys Pro Asp Ser Asp Leu Cys Leu Lys
                465                 470                 475

TTT GCC ATG CTG TGT ACT CTC AAT GAC AAG TGT GAC CGG CTG CGC AAG      286
Phe Ala Met Leu Cys Thr Leu Asn Asp Lys Cys Asp Arg Leu Arg Lys
            480                 485                 490

GCC TAC GGG GAG GCG TGC TCC GGG CCC CAC TGC CAG CGC CAC GTC TGC      334
Ala Tyr Gly Glu Ala Cys Ser Gly Pro His Cys Gln Arg His Val Cys
        495                 500                 505
```

```
CTC AGG CAG CTG CTC ACT TTC TTC GAG AAG GCC GCC GAG CCC CAC GCG      382
Leu Arg Gln Leu Leu Thr Phe Phe Glu Lys Ala Ala Glu Pro His Ala
    510                 515                 520

CAG GGC CTG CTA CTG TGC CCA TGT GCC CCC AAC GAC CGG GGC TGC GGG      430
Gln Gly Leu Leu Leu Cys Pro Cys Ala Pro Asn Asp Arg Gly Cys Gly
525                 530                 535                 540

GAG CGC CGG CGC AAC ACC ATC GCC CCC AAC TGC GCG CTG CCG CCT GTG      478
Glu Arg Arg Arg Asn Thr Ile Ala Pro Asn Cys Ala Leu Pro Pro Val
                545                 550                 555

GCC CCC AAC TGC CTG GAG CTG CGG CGC CTC TGC TTC TCC GAC CCG CTT      526
Ala Pro Asn Cys Leu Glu Leu Arg Arg Leu Cys Phe Ser Asp Pro Leu
            560                 565                 570

TGC AGA TCA CGC CTG GTG GAT TTC CAG ACC CAC TGC CAT CCC ATG GAC      574
Cys Arg Ser Arg Leu Val Asp Phe Gln Thr His Cys His Pro Met Asp
        575                 580                 585

ATC CTA GGA ACT TGT GCA ACA GAG CAG TCC AGA TGT CTA CGA GCA TAC      622
Ile Leu Gly Thr Cys Ala Thr Glu Gln Ser Arg Cys Leu Arg Ala Tyr
    590                 595                 600

CTG GGG CTG ATT GGG ACT GCC ATG ACC CCC AAC TTT GTC AGC AAT GTC      670
Leu Gly Leu Ile Gly Thr Ala Met Thr Pro Asn Phe Val Ser Asn Val
605                 610                 615                 620

AAC ACC AGT GTT GCC TTA AGC TGC ACC TGC CGA GGC AGT GGC AAC CTG      718
Asn Thr Ser Val Ala Leu Ser Cys Thr Cys Arg Gly Ser Gly Asn Leu
                625                 630                 635

CAG GAG GAG TGT GAA ATG CTG GAA GGG TTC TTC TCC CAC AAC CCC TGC      766
Gln Glu Glu Cys Glu Met Leu Glu Gly Phe Phe Ser His Asn Pro Cys
            640                 645                 650

CTC ACG GAG GCC ATT GCA GCT AAG ATG CGT TTT CAC AGC CAA CTC TTC      814
Leu Thr Glu Ala Ile Ala Ala Lys Met Arg Phe His Ser Gln Leu Phe
        655                 660                 665

TCC CAG GAC TGG CCA CAC CCT ACC TTT GCT GTG ATG GCA CAC CAG AAT      862
Ser Gln Asp Trp Pro His Pro Thr Phe Ala Val Met Ala His Gln Asn
    670                 675                 680

GAA AAC CCT GCT GTG AGG CCA CAG CCC TGG GTG CCC TCT CTT TTC TCC      910
Glu Asn Pro Ala Val Arg Pro Gln Pro Trp Val Pro Ser Leu Phe Ser
685                 690                 695                 700

TGC ACG CTT CCC TTG ATT CTG CTC CTG AGC CTA TGG TAGCTGGACT           956
Cys Thr Leu Pro Leu Ile Leu Leu Leu Ser Leu Trp
                705                 710

TCCCCAGGGC CCTCTTCCCC TCCACCACAC CCAGGTGGAC TTGCAGCCCA CAAGGGGTGA   1016

GGAAAGGACA GCAGCAGGAA GGAGGTGCAG TGCGCAGATG AGGGCACAGG AGAAGCTAAG   1076

GGTTATGACC TCCAGATCCT TACTGGTCCA GTCCTCATTC CCTCCACCCC ATCTCCACTT   1136

CTGATTCATG CTGCCCCTCC TTGGTGGCCA CAATTTAGCC ATGTCATCTG GTGCCTGTGG   1196

GCCTTGCTTT ATTCCTATTA TTGTCCTAAA GTCTCTCTGG GCTCTTGGAT CATGATTAAA   1256

CCTTTGACTT AAAAA                                                    1271

(2) INFORMATION FOR SEQ ID NO:19:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO:19:

Gly Tyr Cys Glu Thr Pro Gln Leu Arg Asn Ser Ser Leu Ile Gly Cys
 1               5                  10                  15
```

```
Met Cys His Arg Arg Met Lys Asn Gln Val Ala Cys Leu Asp Ile Tyr
             20                  25                  30

Trp Thr Val His Arg Ala Arg Ser Leu Gly Asn Tyr Glu Leu Asp Val
         35                  40                  45

Ser Pro Tyr Glu Asp Thr Val Thr Ser Lys Pro Trp Lys Met Asn Leu
     50                  55                  60

Ser Lys Leu Asn Met Leu Lys Pro Asp Ser Asp Leu Cys Leu Lys Phe
 65                  70                  75                  80

Ala Met Leu Cys Thr Leu Asn Asp Lys Cys Asp Arg Leu Arg Lys Ala
                 85                  90                  95

Tyr Gly Glu Ala Cys Ser Gly Pro His Cys Gln Arg His Val Cys Leu
            100                 105                 110

Arg Gln Leu Leu Thr Phe Phe Glu Lys Ala Ala Glu Pro His Ala Gln
        115                 120                 125

Gly Leu Leu Leu Cys Pro Cys Ala Pro Asn Asp Arg Gly Cys Gly Glu
    130                 135                 140

Arg Arg Arg Asn Thr Ile Ala Pro Asn Cys Ala Leu Pro Pro Val Ala
145                 150                 155                 160

Pro Asn Cys Leu Glu Leu Arg Arg Leu Cys Phe Ser Asp Pro Leu Cys
                165                 170                 175

Arg Ser Arg Leu Val Asp Phe Gln Thr His Cys His Pro Met Asp Ile
            180                 185                 190

Leu Gly Thr Cys Ala Thr Glu Gln Ser Arg Cys Leu Arg Ala Tyr Leu
        195                 200                 205

Gly Leu Ile Gly Thr Ala Met Thr Pro Asn Phe Val Ser Asn Val Asn
    210                 215                 220

Thr Ser Val Ala Leu Ser Cys Thr Cys Arg Gly Ser Gly Asn Leu Gln
225                 230                 235                 240

Glu Glu Cys Glu Met Leu Glu Gly Phe Phe Ser His Asn Pro Cys Leu
                245                 250                 255

Thr Glu Ala Ile Ala Ala Lys Met Arg Phe His Ser Gln Leu Phe Ser
            260                 265                 270

Gln Asp Trp Pro His Pro Thr Phe Ala Val Met Ala His Gln Asn Glu
        275                 280                 285

Asn Pro Ala Val Arg Pro Gln Pro Trp Val Pro Ser Leu Phe Ser Cys
    290                 295                 300

Thr Leu Pro Leu Ile Leu Leu Ser Leu Trp
305                 310                 315

(2) INFORMATION FOR SEQ ID NO:20:

(i) SEQUENCE CHARACTERISTICS:
        (A) LENGTH: 1699 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 175..1374

(xi) SEQUENCE DESCRIPTION: SEQ ID NO:20:

TGTGGACGCG CGCTTCGGAG TTGGAGGGCG GCGCCCAGGA CCCTGGTGGG AGAGTGTGTG      60

CGTCGCGCTG GAGGGCGGGA GGCGGGGGCG GGAGGTGCCG GTCGAGGGAG CCCCGCTCTC     120

AGAGCTCCAG GGGAGGAGCG AGGGGAGCGC GGAGCCCGGC GCCTACAGCT CGCC ATG       177
```

-continued

```
                                                    Met
GTG CGC CCC CTG AAC CCG CGA CCG CTG CCG CCC GTA GTC CTG ATG TTG      225
Val Arg Pro Leu Asn Pro Arg Pro Leu Pro Pro Val Val Leu Met Leu
            320                 325                 330

CTG CTG CTG CTG CCG CCG TCG CCG CTG CCT CTC GCA GCC GGA GAC CCC      273
Leu Leu Leu Leu Pro Pro Ser Pro Leu Pro Leu Ala Ala Gly Asp Pro
            335                 340                 345

CTT CCC ACA GAA AGC CGA CTC ATG AAC AGC TGT CTC CAG GCC AGG AGG      321
Leu Pro Thr Glu Ser Arg Leu Met Asn Ser Cys Leu Gln Ala Arg Arg
    350                 355                 360

AAG TGC CAG GCT GAT CCC ACC TGC AGT GCT GCC TAC CAC CAC CTG GAT      369
Lys Cys Gln Ala Asp Pro Thr Cys Ser Ala Ala Tyr His His Leu Asp
365                 370                 375                 380

TCC TGC ACC TCT AGC ATA AGC ACC CCA CTG CCC TCA GAG GAG CCT TCG      417
Ser Cys Thr Ser Ser Ile Ser Thr Pro Leu Pro Ser Glu Glu Pro Ser
                385                 390                 395

GTC CCT GCT GAC TGC CTG GAG GCA GCA CAG CAA CTC AGG AAC AGC TCT      465
Val Pro Ala Asp Cys Leu Glu Ala Ala Gln Gln Leu Arg Asn Ser Ser
                    400                 405                 410

CTG ATA GGC TGC ATG TGC CAC CGG CGC ATG AAG AAC CAG GTT GCC TGC      513
Leu Ile Gly Cys Met Cys His Arg Arg Met Lys Asn Gln Val Ala Cys
            415                 420                 425

TTG GAC ATC TAT TGG ACC GTT CAC CGT GCC CGC AGC CTT GGT AAC TAT      561
Leu Asp Ile Tyr Trp Thr Val His Arg Ala Arg Ser Leu Gly Asn Tyr
    430                 435                 440

GAG CTG GAT GTC TCC CCC TAT GAA GAC ACA GTG ACC AGC AAA CCC TGG      609
Glu Leu Asp Val Ser Pro Tyr Glu Asp Thr Val Thr Ser Lys Pro Trp
445                 450                 455                 460

AAA ATG AAT CTC AGC AAA CTG AAC ATG CTC AAA CCA GAC TCA GAC CTC      657
Lys Met Asn Leu Ser Lys Leu Asn Met Leu Lys Pro Asp Ser Asp Leu
                465                 470                 475

TGC CTC AAG TTT GCC ATG CTG TGT ACT CTC AAT GAC AAG TGT GAC CGG      705
Cys Leu Lys Phe Ala Met Leu Cys Thr Leu Asn Asp Lys Cys Asp Arg
                    480                 485                 490

CTG CGC AAG GCC TAC GGG GAG GCG TGC TCC GGG CCC CAC TGC CAG CGC      753
Leu Arg Lys Ala Tyr Gly Glu Ala Cys Ser Gly Pro His Cys Gln Arg
            495                 500                 505

CAC GTC TGC CTC AGG CAG CTG CTC ACT TTC TTC GAG AAG GCC GCC GAG      801
His Val Cys Leu Arg Gln Leu Leu Thr Phe Phe Glu Lys Ala Ala Glu
    510                 515                 520

CCC CAC GCG CAG GGC CTG CTA CTG TGC CCA TGT GCC CCC AAC GAC CGG      849
Pro His Ala Gln Gly Leu Leu Leu Cys Pro Cys Ala Pro Asn Asp Arg
525                 530                 535                 540

GGC TGC GGG GAG CGC CGG CGC AAC ACC ATC GCC CCC AAC TGC GCG CTG      897
Gly Cys Gly Glu Arg Arg Arg Asn Thr Ile Ala Pro Asn Cys Ala Leu
                545                 550                 555

CCG CCT GTG GCC CCC AAC TGC CTG GAG CTG CGG CGC CTC TGC TTC TCC      945
Pro Pro Val Ala Pro Asn Cys Leu Glu Leu Arg Arg Leu Cys Phe Ser
                    560                 565                 570

GAC CCG CTT TGC AGA TCA CGC CTG GTG GAT TTC CAG ACC CAC TGC CAT      993
Asp Pro Leu Cys Arg Ser Arg Leu Val Asp Phe Gln Thr His Cys His
            575                 580                 585

CCC ATG GAC ATC CTA GGA ACT TGT GCA ACA GAG CAG TCC AGA TGT CTA     1041
Pro Met Asp Ile Leu Gly Thr Cys Ala Thr Glu Gln Ser Arg Cys Leu
    590                 595                 600

CGA GCA TAC CTG GGG CTG ATT GGG ACT GCC ATG ACC CCC AAC TTT GTC     1089
Arg Ala Tyr Leu Gly Leu Ile Gly Thr Ala Met Thr Pro Asn Phe Val
605                 610                 615                 620

AGC AAT GTC AAC ACC AGT GTT GCC TTA AGC TGC ACC TGC CGA GGC AGT     1137
Ser Asn Val Asn Thr Ser Val Ala Leu Ser Cys Thr Cys Arg Gly Ser
```

-continued

```
Ser Asn Val Asn Thr Ser Val Ala Leu Ser Cys Thr Cys Arg Gly Ser
            625                 630                 635

GGC AAC CTG CAG GAG GAG TGT GAA ATG CTG GAA GGG TTC TTC TCC CAC      1185
Gly Asn Leu Gln Glu Glu Cys Glu Met Leu Glu Gly Phe Phe Ser His
            640                 645                 650

AAC CCC TGC CTC ACG GAG GCC ATT GCA GCT AAG ATG CGT TTT CAC AGC      1233
Asn Pro Cys Leu Thr Glu Ala Ile Ala Ala Lys Met Arg Phe His Ser
            655                 660                 665

CAA CTC TTC TCC CAG GAC TGG CCA CAC CCT ACC TTT GCT GTG ATG GCA      1281
Gln Leu Phe Ser Gln Asp Trp Pro His Pro Thr Phe Ala Val Met Ala
        670                 675                 680

CAC CAG AAT GAA AAC CCT GCT GTG AGG CCA CAG CCC TGG GTG CCC TCT      1329
His Gln Asn Glu Asn Pro Ala Val Arg Pro Gln Pro Trp Val Pro Ser
685                 690                 695                 700

CTT TTC TCC TGC ACG CTT CCC TTG ATT CTG CTC CTG AGC CTA TGG          1374
Leu Phe Ser Cys Thr Leu Pro Leu Ile Leu Leu Leu Ser Leu Trp
                    705                 710                 715

TAGCTGGACT TCCCCAGGGC CTCTTCCCC TCCACCACAC CCAGGTGGAC TTGCAGCCCA     1434

CAAGGGGTGA GGAAAGGACA GCAGCAGGAA GGAGGTGCAG TGCGCAGATG AGGGCACAGG    1494

AGAAGCTAAG GGTTATGACC TCCAGATCCT TACTGGTCCA GTCCTCATTC CCTCCACCCC    1554

ATCTCCACTT CTGATTCATG CTGCCCCTCC TTGGTGGCCA CAATTTAGCC ATGTCATCTG    1614

GTGCCTGTGG GCCTTGCTTT ATTCCTATTA TTGTCCTAAA GTCTCTCTGG GCTCTTGGAT    1674

CATGATTAAA CCTTTGACTT AAAAA                                         1699

(2) INFORMATION FOR SEQ ID NO:21:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:21:

Met Val Arg Pro Leu Asn Pro Arg Pro Leu Pro Pro Val Val Leu Met
 1               5                  10                  15

Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175
```

```
Arg Leu Arg Lys Ala Tyr Gly Glu Ala Cys Ser Gly Pro His Cys Gln
            180                 185                 190
Arg His Val Cys Leu Arg Gln Leu Leu Thr Phe Phe Glu Lys Ala Ala
        195                 200                 205
Glu Pro His Ala Gln Gly Leu Leu Leu Cys Pro Cys Ala Pro Asn Asp
    210                 215                 220
Arg Gly Cys Gly Glu Arg Arg Asn Thr Ile Ala Pro Asn Cys Ala
225                 230                 235                 240
Leu Pro Pro Val Ala Pro Asn Cys Leu Glu Leu Arg Arg Leu Cys Phe
                245                 250                 255
Ser Asp Pro Leu Cys Arg Ser Arg Leu Val Asp Phe Gln Thr His Cys
            260                 265                 270
His Pro Met Asp Ile Leu Gly Thr Cys Ala Thr Glu Gln Ser Arg Cys
        275                 280                 285
Leu Arg Ala Tyr Leu Gly Leu Ile Gly Thr Ala Met Thr Pro Asn Phe
    290                 295                 300
Val Ser Asn Val Asn Thr Ser Val Ala Leu Ser Cys Thr Cys Arg Gly
305                 310                 315                 320
Ser Gly Asn Leu Gln Glu Glu Cys Glu Met Leu Glu Gly Phe Phe Ser
                325                 330                 335
His Asn Pro Cys Leu Thr Glu Ala Ile Ala Ala Lys Met Arg Phe His
            340                 345                 350
Ser Gln Leu Phe Ser Gln Asp Trp Pro His Pro Thr Phe Ala Val Met
            355                 360                 365
Ala His Gln Asn Glu Asn Pro Ala Val Arg Pro Gln Pro Trp Val Pro
        370                 375                 380
Ser Leu Phe Ser Cys Thr Leu Pro Leu Ile Leu Leu Leu Ser Leu Trp
385                 390                 395                 400
```